US012675770B2

(12) United States Patent (10) Patent No.: US 12,675,770 B2
Carey et al. (45) Date of Patent: *Jul. 7, 2026

(54) SYSTEMS AND METHODS FOR GOVERNING ENERGY INFORMATION AND ANALYSIS

(71) Applicant: INTERTRUST TECHNOLOGIES CORPORATION, Berkeley, CA (US)

(72) Inventors: W. Knox Carey, Mountain View, CA (US); David P. Maher, Livermore, CA (US); Michael G. Manente, Sudbury, MA (US); Jarl Nilsson, Mountain View, CA (US); Talal G. Shamoon, Berkeley, CA (US)

(73) Assignee: Intertrust Technologies Corporation, Berkeley, CA (US)

( * ) Notice: Subject to any disclaimer, the term of this patent is extended or adjusted under 35 U.S.C. 154(b) by 396 days.

This patent is subject to a terminal disclaimer.

(21) Appl. No.: 18/049,145

(22) Filed: Oct. 24, 2022

(65) Prior Publication Data

US 2023/0074310 A1 Mar. 9, 2023

Related U.S. Application Data

(63) Continuation of application No. 16/845,650, filed on Apr. 10, 2020, now Pat. No. 11,481,729, which is a
(Continued)

(51) Int. Cl.
*G06Q 10/10* (2023.01)
*G06F 21/10* (2013.01)
(Continued)

(52) U.S. Cl.
CPC ............. *G06Q 10/10* (2013.01); *G06F 21/10* (2013.01); *G06F 21/6263* (2013.01);
(Continued)

(58) Field of Classification Search
CPC ........ G06Q 10/10; G06Q 50/22; G06F 21/10; G06F 21/6263; G06F 2221/2145;
(Continued)

(56) References Cited

U.S. PATENT DOCUMENTS 6,065,119 A 5/2000 Sandford et al.
6,944,767 B1 9/2005 Judson
(Continued)

FOREIGN PATENT DOCUMENTS

CN 1860424 11/2006
CN 101133418 2/2008
(Continued)

OTHER PUBLICATIONS

First Australian Examination Report dated Mar. 19, 2015 in Australian Patent Application No. 2012326132.
(Continued)

*Primary Examiner* — Charles R Kasenge
(74) *Attorney, Agent, or Firm* — John P. Davis; Thayne and Davis LLC

(57) ABSTRACT

Trusted, privacy-protected systems and methods are disclosed for processing, handling, and performing tests on human genomic and other information. According to some embodiments, a system is disclosed that is a cloud-based system for the trusted storage and analysis of genetic and other information. Some embodiments of the system may include or support some or all of authenticated and certified data sources; authenticated and certified diagnostic tests; and policy-based access to data.

20 Claims, 27 Drawing Sheets

Related U.S. Application Data continuation of application No. 13/654,349, filed on Oct. 17, 2012, now Pat. No. 10,621,550.

(60) Provisional application No. 61/617,593, filed on Mar. 29, 2012, provisional application No. 61/548,161, filed on Oct. 17, 2011.

(51) Int. Cl.

| | |
|---|---|
| *G06F 21/62* | (2013.01) |
| *G16B 50/00* | (2019.01) |
| *G16B 50/30* | (2019.01) |
| *G16B 50/40* | (2019.01) |
| *G16B 50/50* | (2019.01) |
| *G16H 10/40* | (2018.01) |
| *G16H 10/60* | (2018.01) |

(52) U.S. Cl.

CPC ............. *G16B 50/00* (2019.02); *G16B 50/30* (2019.02); *G16B 50/40* (2019.02); *G16H 10/40* (2018.01); *G06F 2221/2145* (2013.01); *G16H 10/60* (2018.01)

(58) Field of Classification Search

CPC ........ G16B 50/00; G16B 50/30; G16B 50/40; G16H 10/40; G16H 10/60

See application file for complete search history.

(56) References Cited

U.S. PATENT DOCUMENTS

| | | | | |
|---|---|---|---|---|
| 7,542,947 | B2 | 6/2009 | Guyon | |
| 8,571,881 | B2 | 10/2013 | Rousso | |
| 11,481,729 | B2 * | 10/2022 | Carey | G16H 10/40 |
| 2002/0052761 | A1 | 5/2002 | Fey et al. | |
| 2002/0174115 | A1 | 11/2002 | Shibuya et al. | |
| 2003/0055824 | A1 | 3/2003 | Califano | |
| 2003/0233250 | A1 | 12/2003 | Joffe | |
| 2004/0014097 | A1 | 1/2004 | McGlennen | |
| 2004/0073570 | A1 | 4/2004 | Janakiraman | |
| 2005/0026117 | A1 | 2/2005 | Judson et al. | |
| 2005/0065743 | A1 * | 3/2005 | Cumming | G01R 22/10 |
| | | | | 702/62 |
| 2005/0066169 | A1 | 3/2005 | Kiehtreiber et al. | |
| 2005/0144042 | A1 | 6/2005 | Joffe | |
| 2005/0188207 | A1 | 8/2005 | Fujimoto et al. | |
| 2005/0191731 | A1 | 9/2005 | Judson | |
| 2006/0085634 | A1 | 4/2006 | Jain | |
| 2006/0242075 | A1 | 10/2006 | Ginter | |
| 2006/0248349 | A1 | 11/2006 | Rathjen | |
| 2006/0248466 | A1 | 11/2006 | Fedorenko et al. | |
| 2006/0271406 | A1 | 11/2006 | Califano et al. | |
| 2007/0006322 | A1 | 1/2007 | Karimzadeh | |
| 2007/0124580 | A1 | 5/2007 | Brownell | |
| 2007/0180519 | A1 | 8/2007 | Boccon-Gibod | |
| 2007/0208869 | A1 | 9/2007 | Adelman | |
| 2007/0220009 | A1 | 9/2007 | Morris | |
| 2008/0155268 | A1 | 6/2008 | Jezayeri et al. | |
| 2008/0189047 | A1 | 8/2008 | Wong | |
| 2008/0271144 | A1 | 10/2008 | Bleumer | |
| 2009/0094059 | A1 | 4/2009 | Coleman | |
| 2009/0254753 | A1 | 10/2009 | De Atley | |
| 2009/0287837 | A1 | 11/2009 | Felsher | |
| 2009/0327079 | A1 | 12/2009 | Parker | |
| 2010/0023761 | A1 | 1/2010 | Shear | |
| 2010/0050253 | A1 | 2/2010 | Baughman | |
| 2010/0169107 | A1 | 7/2010 | Ahn | |
| 2010/0169651 | A1 | 7/2010 | Scheidt | |
| 2010/0273147 | A1 | 10/2010 | Valenti | |
| 2010/0333194 | A1 | 12/2010 | Ricordi | |
| 2011/0047189 | A1 | 2/2011 | Will | |
| 2011/0082704 | A1 | 4/2011 | Blum | |
| 2011/0111389 | A1 | 5/2011 | Tam | |
| 2011/0191821 | A1 | 8/2011 | Pinsky | |
| 2011/0288785 | A1 | 11/2011 | Tembe | |
| 2012/0011578 | A1 | 1/2012 | Hinton | |
| 2012/0054625 | A1 | 3/2012 | Pugh | |
| 2012/0260346 | A1 | 10/2012 | Carey | |
| 2013/0007845 | A1 | 1/2013 | Chang | |
| 2013/0023434 | A1 | 1/2013 | Van Laar | |
| 2013/0054552 | A1 * | 2/2013 | Hawkins | G06N 20/00 |
| | | | | 707/706 |
| 2013/0066940 | A1 | 3/2013 | Shao | |
| 2014/0032125 | A1 | 1/2014 | Hawkins | |

FOREIGN PATENT DOCUMENTS

| | | |
|---|---|---|
| CN | 101477602 | 7/2009 |
| CN | 101605909 | 12/2009 |
| JP | 1998011281 | 1/1998 |
| JP | 2004287847 | 10/2004 |
| JP | 2004290240 | 10/2004 |
| JP | 2007265404 | 10/2007 |
| JP | 2009076069 | 4/2009 |
| JP | 2010157231 | 7/2010 |
| WO | 2005088504 | 9/2005 |
| WO | 2010077336 | 7/2010 |
| WO | 2002044967 | 6/2022 |

OTHER PUBLICATIONS

Second Australian Examination Report dated Feb. 4, 2016 in Australian Patent Application No. 2012326132.

First Indian Examination Report dated Dec. 23, 2019 in Indian Patent Application No. 976/KOLNP/2014.

Examination Communication dated Oct. 10, 2018, in European Patent Application No. 12840934.9.

Callaway, E.; Global Genomic Data-Sharing Effort Kicks Off; Nature News; Mar. 6, 2014; pp. 1-2.

Extended European Search Report dated Feb. 3, 2015 in European Patent Application No. 12840934.9.

First Chinese Office Action dated Mar. 3, 2016 in Chinese Patent Application No. 201280062102.5.

Second Chinese Office Action dated Dec. 26, 2016 in Chinese Patent Application No. 201280062102.5.

Gyrnrek, M. et al.: "Identifying Personal Genomes by Surname Inference"; Science, vol. 339, No. 6117; Jan. 18, 2013; pp. 321-324.

Homer, N. et al.; "Resolving individuals contributing trace amounts of DNA to highly complex mixtures using high-density SNP genotyping microarrays"; PLoS Genetics; vol. 4,. No. 8; Aug. 2008; pp. 1-9.

International Search Report and the Written Opinion of the International Searching Authority dated Dec. 27, 2012 in International Patent Application No. PCT /US2012/060678. First Japanese Office Action dated Oct. 12, 2016 in Japanese Patent Application No. 2014-537190.

Kolata, G.; "Poking Holes in Genetic Privacy"; New York Times, Jun. 16, 2013; pp. 1-3.

Lemke, A.A. et al.; "Public and Biobank Participant Attitudes toward Genetic Research Participation and Data Sharing"; Public Health Genomics, vol. 13; Jan. 15, 2010; pp. 368-377.

Lunshof, J. et al.; "From Genetic Privacy to Open Consent"; Nature Reviews | Genetics; vol. 9; May 2008; pp. 406-411.

Nyholt, D. et al.; "On Jim Watson's APOE status: genetic information is hard to hide"; European Journal of Human Genetics; vol. 17, No. 2; Feb. 2009; pp. 147-149.

Sankararaman, S. et al.; "Genomic privacy and limits of individual detection in a pool"; Nature Genetics; vol. 41, No. 9; Sep. 2009; pp. 965-967.

First Chinese Office Action dated Apr. 2, 2020 in Chinese Patent Application No. 201710533339.1.

Second Chinese Office Action dated Dec. 28, 2020 in Chinese Patent Application No. 201710533339.1.

First Chinese Search Report dated Apr. 13, 2020 in Chinese Patent Application No. 201710533339.1.

(56)  References Cited

OTHER PUBLICATIONS

Gookin, Microsoft Office Word 2007 for Dummies, Wiley Publishing, 2007, pp. 128-130, 231, 317-318.
WO2002044967 WIPO English Machine Translation (6 pgs).

* cited by examiner

222
Trust
Authority

225
Transaction
Clearinghouse

221
VDT
Marketplace

224
Research
Service

220
Genetic
Database

223
VDT Execution
Environment

Certificates for each government entity that may have authority over medical device certification, lab certifications, etc.

Examples:
US Jurisdiction (e.g. certificates for FDA, NIH, CDC)
EU Jurisdiction
CN Jurisdiction

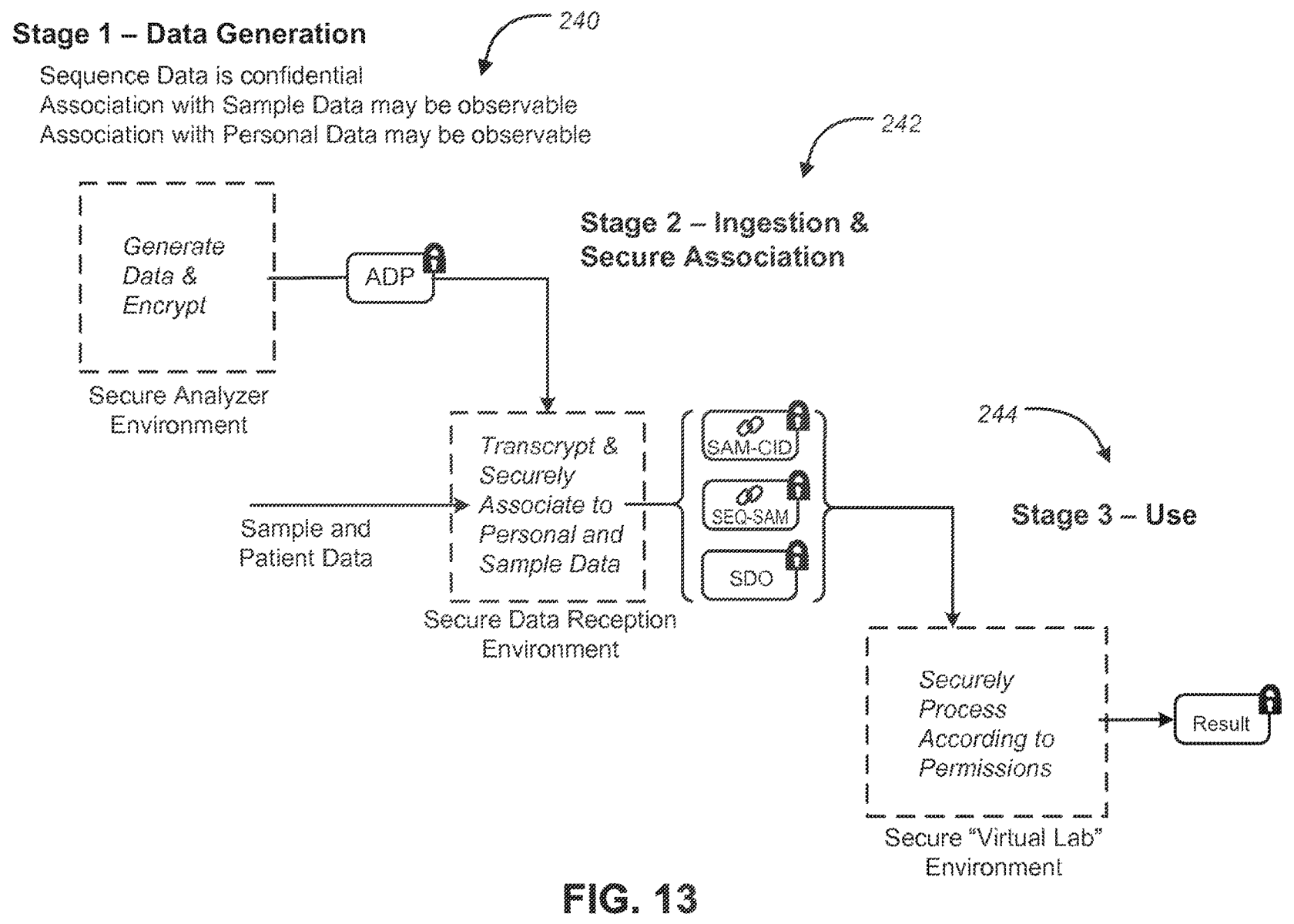

Stage 1 – Data Generation

Sequence Data is confidential
Association with Sample Data may be observable
Association with Personal Data may be observable

240

**Stage 2 – Ingestion &
Secure Association**

242

Stage 3 – Use

244

*Generate
Data &
Encrypt*

Secure Analyzer
Environment

ADP

*Transcript &
Securely
Associate to
Personal and
Sample Data*

Secure Data Reception
Environment

Sample and
Patient Data

SAM-CID

SEQ-SAM

SDO

*Securely
Process
According to
Permissions*

Secure "Virtual Lab"
Environment

Result

FIG. 13

<Username> has requested the following test on your genomic data. Your current privacy settings indicate you would like to approve tests of this type or tests from this category of user.

Test Request ID: nnnnnn
Testname: xxxxxxxx

Test Description:
y∼∼∼∼∼∼∼∼∼∼∼∼∼∼∼∼∼∼∼∼∼∼∼∼∼∼∼∼∼∼∼∼∼∼∼∼∼∼∼∼∼∼∼∼
∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼
∼∼∼∼∼∼∼∼∼∼∼∼∼∼∼∼∼∼∼∼∼∼∼∼∼∼∼∼∼∼∼∼∼∼∼∼∼

Click here for a more detailed description of this test

Privacy Considerations:
z∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼
∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼∼

☐ Check here if you would like to edit privacy settings that determine when you receive these notifications

[Approve]     [Reject]

Figure 18:
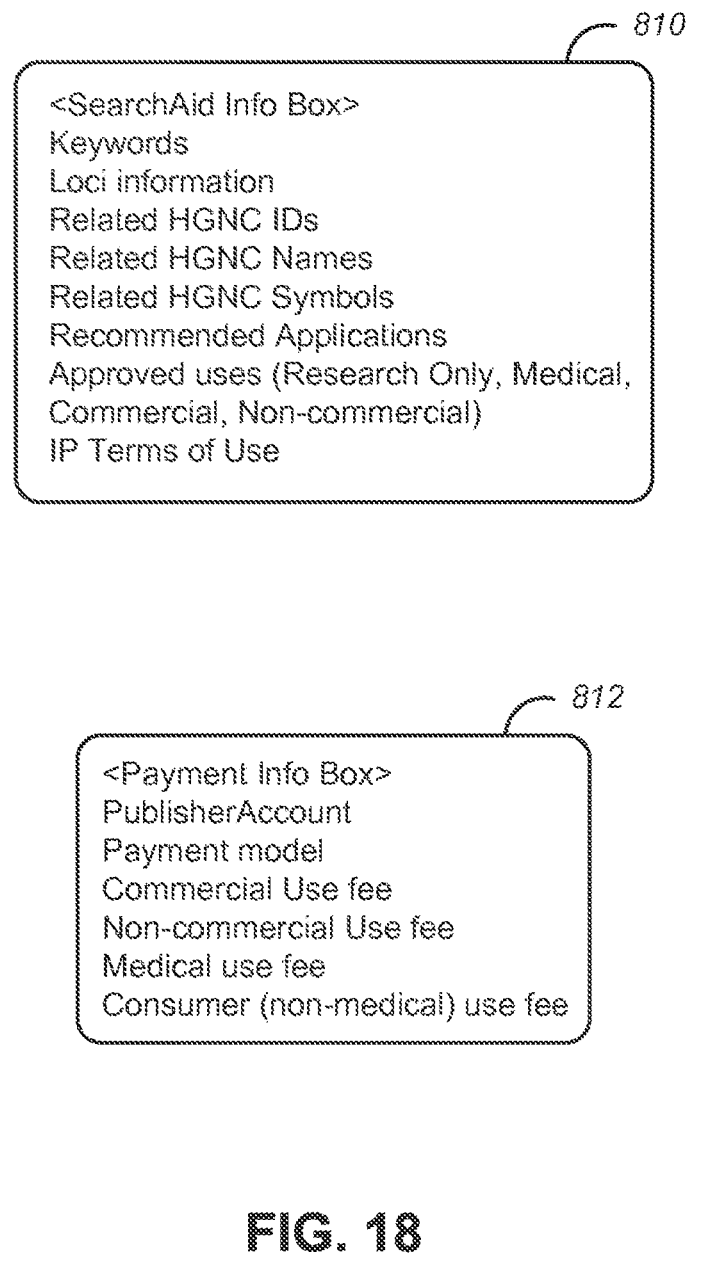

<SearchAid Info Box>
Keywords
Loci information
Related HGNC IDs
Related HGNC Names
Related HGNC Symbols
Recommended Applications
Approved uses (Research Only, Medical,
Commercial, Non-commercial)
IP Terms of Use

_812_

<Payment Info Box>
PublisherAccount
Payment model
Commercial Use fee
Non-commercial Use fee
Medical use fee
Consumer (non-medical) use fee

```
<Test Algorithm>
TestFormat and Version Information
<Test Logic>
Sample1=INPUT1
Locus1=xxxx
Locus2=yyyy
IF (Sample1,locus1,patternB) THEN
T1=TRUE
IF (Sample2,locus1,patternA) AND
(locus3,"C") THEN T2=TRUE
IF (T1=TRUE) OR (T2=TRUE) THEN
RESULT="POSITIVE"
ELSE RESULT="NEGATIVE"
<Report Output>
Print "Test for XXX"
Print "Result is:",RESULT
<Pattern Resources>
Pattern1:"ACCGTCCC"
Pattern2:"ACTC"
```

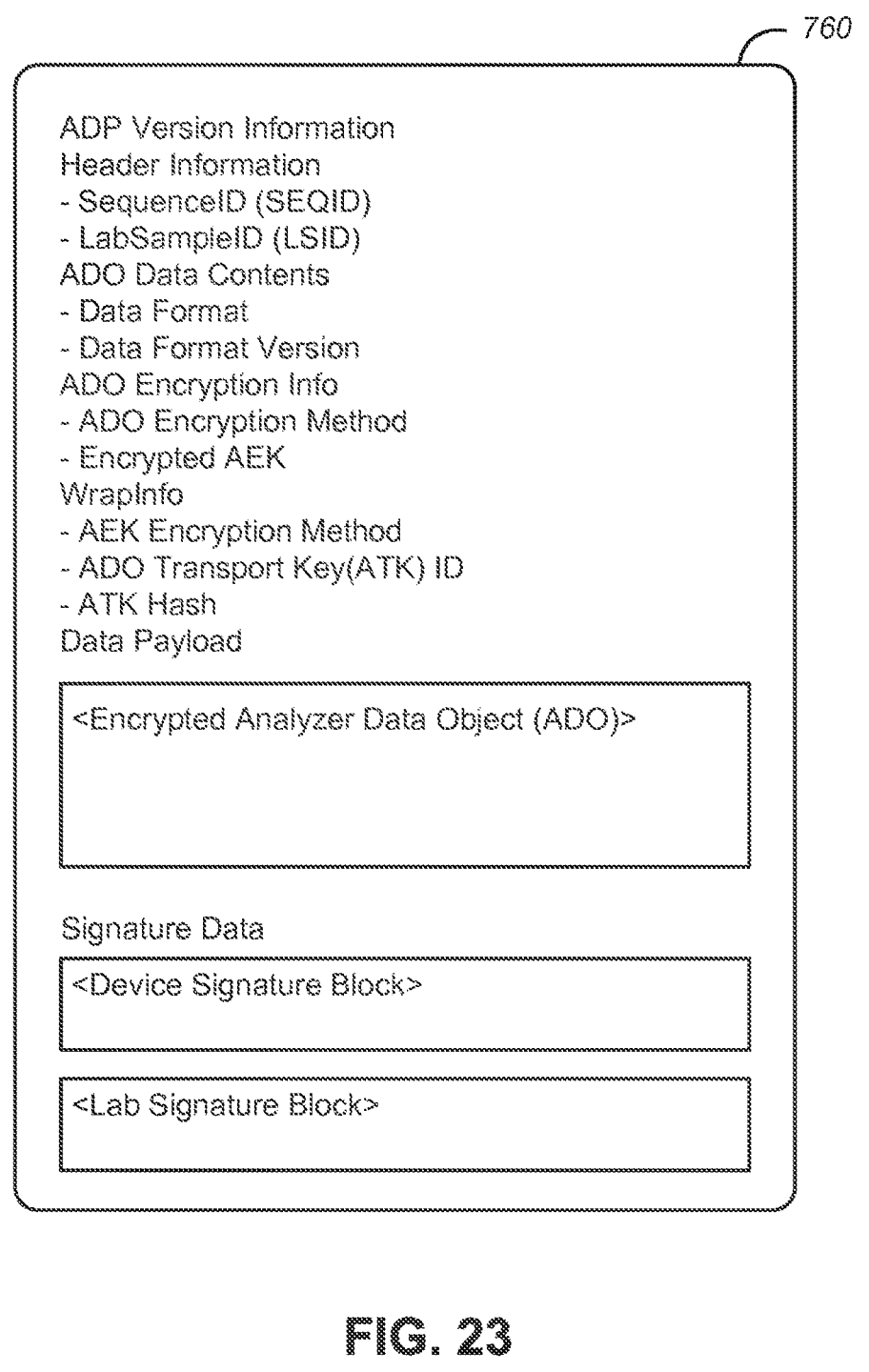

ADP Version Information
Header Information
- SequenceID (SEQID)
- LabSampleID (LSID)
ADO Data Contents
- Data Format
- Data Format Version
ADO Encryption Info
- ADO Encryption Method
- Encrypted AEK
WrapInfo
- AEK Encryption Method
- ADO Transport Key(ATK) ID
- ATK Hash
Data Payload <Encrypted Analyzer Data Object (ADO)>

Signature Data

<Device Signature Block>

<Lab Signature Block>

FIG. 23

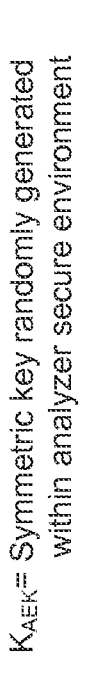
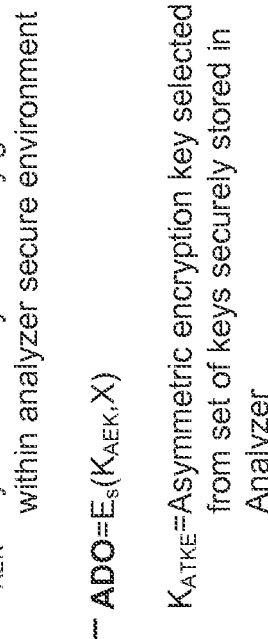
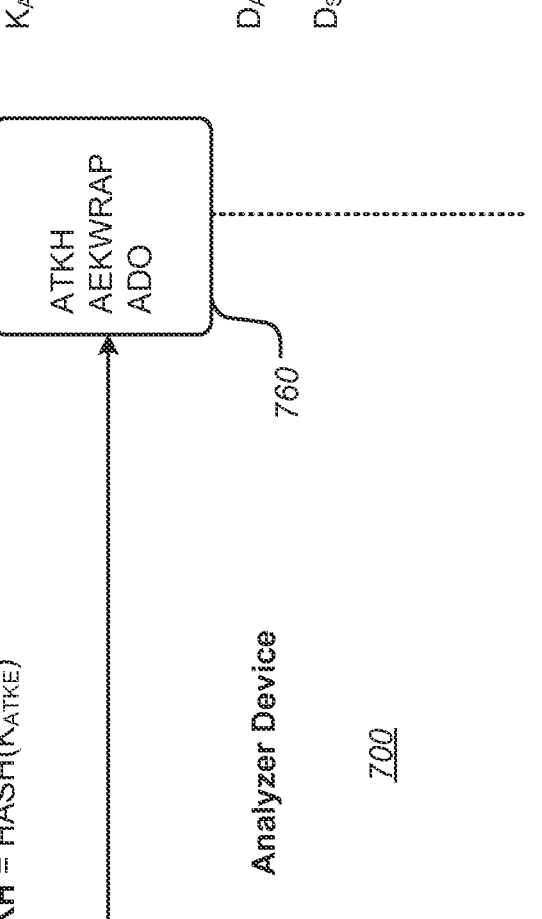

$X$ = Encoder Analyzer Output Data $K_{AEK}$ = Symmetric key randomly generated within analyzer secure environment

ADO = $E_S(K_{AEK}, X)$ $K_{ATKE}$ = Asymmetric encryption key selected from set of keys securely stored in Analyzer

AEKWRAP = $E_A(K_{ATKE}, K_{AEK})$

ATKH = $HASH(K_{ATKE})$

Analyzer Data Package (ADP)

ATKH
AEKWRAP
ADO

760

Analyzer Device

_700_

Gene Cloud Secure Data Reception Environment

ATKH = Lookup Value $K_{ATKD}$ = Asymmetric decryption key corresponding to $K_{ATKE}$, retrieved from set of keys securely stored in Secure Reception Environment. (Uniquely located using ATKH value)

$D_A(K_{ATKD}, $ AEKWRAP$) = K_{AEK}$ $D_S(K_{AEK}, $ ADO$) = $ Encoded Analyzer Output Data

FIG. 24

SYSTEMS AND METHODS FOR GOVERNING ENERGY INFORMATION AND ANALYSIS

CROSS REFERENCE TO RELATED APPLICATIONS

This application is a continuation of U.S. patent application Ser. No. 16/845,650, filed Apr. 10, 2020, which is a continuation of U.S. patent application Ser. No. 13/654,349, filed Oct. 17, 2012 (now U.S. Pat. No. 10,621,550), which claims the benefit of priority of Provisional Application Nos. 61/548,161, filed Oct. 17, 2011, and 61/617,593, filed Mar. 29, 2012, all of which are hereby incorporated by reference in their entireties.

COPYRIGHT AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND AND SUMMARY

Genetic testing is moving from detection of Single Nucleotide Polymorphisms (SNPs)—isolated individual chemical differences in the genetic code—to Whole Genome Sequencing (WGS), which records every base pair in a genetic sequence. Currently, companies are focusing on creating devices that can affordably produce whole genome sequences for individuals. It is expected that in the next three years, devices will be commercially available that can sequence an entire genome for less than $500 in less than one day. The primary industry focus today is on developing the sequencing technology, biochemistry, and first stage genomic data processing (raw data processing and base-calling statistical processing).

According to some embodiments, a method is described for performing trusted computations on human genomic or other data. The described method includes: receiving a set of genomic or other data and an executable diagnostic computer program designed to operate on genomic or other data; evaluating authenticity of the executable diagnostic computer program; evaluating authenticity of at least a portion of the set of data; and when the authenticity evaluations are satisfactory, executing the computer program upon at least a portion of the set of data. According to some embodiments, diagnostic results are generated that are useful in a medical diagnosis based on the execution of the computer program. The method can also include certifying the authenticity of the results. The evaluation of authenticity of the diagnostic computer program can include verifying a digital signature packaged with the received diagnostic computer program. Similarly, the evaluation of authenticity of the genomic or other data can include verifying a digital signature packaged with the data. According to some embodiments the method also includes maintaining privacy associated with the set of data based on one or more privacy policies.

According to some embodiments, a trusted computing system is described that includes: a secure storage system configured to store at least a portion of a set of data and a computer program for operating on the data; and a secure processing system programmed and configured to evaluate the authenticity of the computer program, to evaluate the authenticity of at least a portion of the set of data, and when the authenticity evaluations are satisfactory, to run the computer program on at least a portion of the set of data.

According to some embodiments, an executable diagnostic computer program is described that includes: a diagnostic algorithm configured to execute on at least a portion of a data set so as to generate therefrom diagnostic results (e.g., results that are useful in a medical diagnosis); and a digital signature configured to aid in demonstrating the authenticity of the executable program. According to some embodiments, the computer program can also be packaged with: metadata that describes the diagnostic algorithm, an intended use of the algorithm, and one or more precautions associated with the algorithm; technical description of inputs to the algorithm which are expected in order to generate the useful diagnostic results; and/or information describing aspects of expected output from the diagnostic algorithm.

According to some embodiments, a method of generating packaged genomic data is described that includes: receiving genomic data from a DNA-sequencing device; encrypting the received genomic data; generating a digital signature which will facilitate subsequent verification of the genomic data; and packaging the generated digital signature with the encrypted genomic data. The digital signature can be generated using a private key associated with the DNA-sequencing device and/or a private key associated with the sequencing facility.

According to some embodiments, a method of operating on one or more sets of genomic data is described that includes: securely receiving one or more sets of genomic data; associating permission information with each set of genomic data, the permission information having been specified by an owner of the genomic data; receiving an algorithm to operate on genomic data; receiving a request to run the algorithm on one or more sets of received genomic data; authenticating the request; checking permissions associated with a set of genomic data; and allowing the algorithm to access or use the set of genomic data if allowed by the permissions.

As used herein, the term "genomic data" generally refers to data expressing, representing, or derived from the entirety or a portion of a genome or genome sequence. This data may include, for example, information encoded in chemical structures such as DNA, mRNA, and proteins as well as related regulatory information such as methylation status.

As used herein the term "genome" refers to an organism's hereditary information. A genome is encoded in DNA or RNA, and may be represented as mRNA or as protein sequences derived from these nucleic acid sequences. The term "genome" can include both genes and non-coding sequences. When applied to a specific organism, the term "genome" can refer to genomic data from normal cells—including mitochondrial DNA—and also genomic data from related cells such as tumors and other organisms of the microbiome.

BRIEF DESCRIPTION OF THE DRAWINGS

The inventive body of work will be readily understood by referring to the following detailed description in conjunction with the accompanying drawings, in which:

FIG. 13 is an illustration showing a set of example stages in the lifecycle of genetic information in an illustrative embodiment of a Gene Cloud system;

FIG. 15 shows an example of a template for an automatically-generated authorization request, according to some embodiments;

FIG. 18 shows examples of extended metadata, according to some embodiments;

FIG. 19 shows an example of a Virtual Diagnostic Test (VDT) algorithm specification, according to some embodiments;

FIG. 23 shows an example of an analyzer data package (ADP) format, according to some embodiments;

FIG. 24 shows an illustrative relationship between keys in the environment of an analyzer and keys at the point of ingestion of a Gene Cloud system, according to some embodiments;

DETAILED DESCRIPTION

A detailed description of the inventive body of work is provided below. While several embodiments are described, it should be understood that the inventive body of work is not limited to any one embodiment, but instead encompasses numerous alternatives, modifications, and equivalents. In addition, while numerous specific details are set forth in the following description in order to provide a thorough understanding of the inventive body of work, some embodiments can be practiced without some or all of these details. Moreover, for the purpose of clarity, certain technical material that is known in the related art has not been described in detail in order to avoid unnecessarily obscuring the inventive body of work.

Systems and methods are presented for facilitating trusted handling of genomic and/or other information. It will be appreciated that these systems and methods are novel, as are many of the components, systems, and methods employed therein.

Genomic data is perhaps the most personally identifiable health data currently available. With many conventional medical tests, once a sample is taken and tested, the sample is discarded and no further tests can be performed. However, with Whole Genome Sequencing (WGS), your "data sample" can live on indefinitely. Tests can later be performed on the data as new genes are identified, without the need for additional laboratory work.

If data is not adequately protected, the patient is essentially agreeing to the tests that are known today—and also to any that may be discovered during the patient's lifetime. Revealing genetic information can have far-reaching consequences: such as spousal selection/desirability; employment screening/employability; and profiling/discrimination, to name just a few examples. Furthermore, revealing information about an individual's genome may inadvertently reveal information about genetically related family members, such as siblings, children, and twins.

Figure 1A:
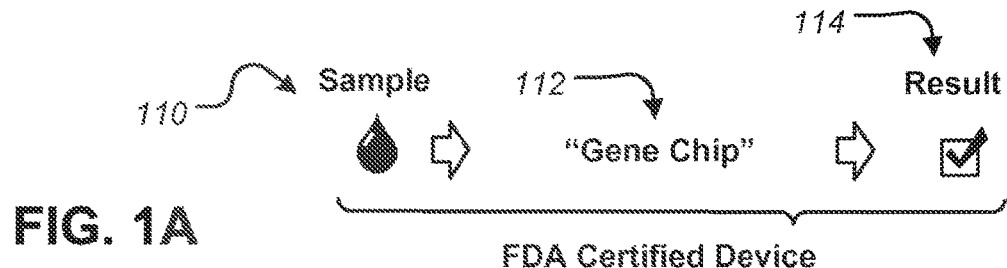
FIGS. 1A, 1B, and 1C illustrate a transition from tightly coupled genetic tests using a physical medical device to decoupled sequencing and testing steps, where the testing steps include a series of software analyses performed on the original sequence.
Figure 1B:
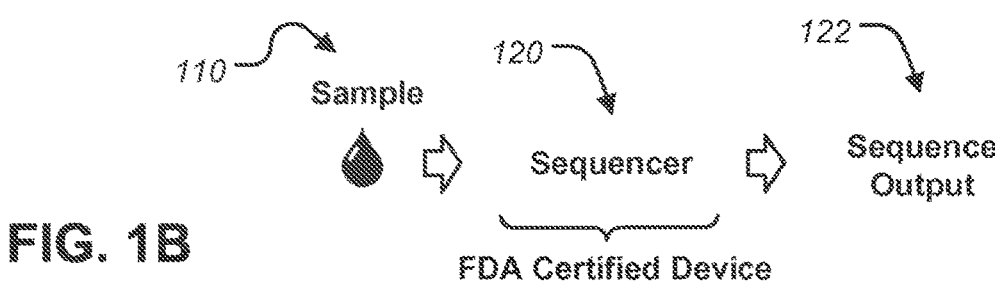
Figure 1C:
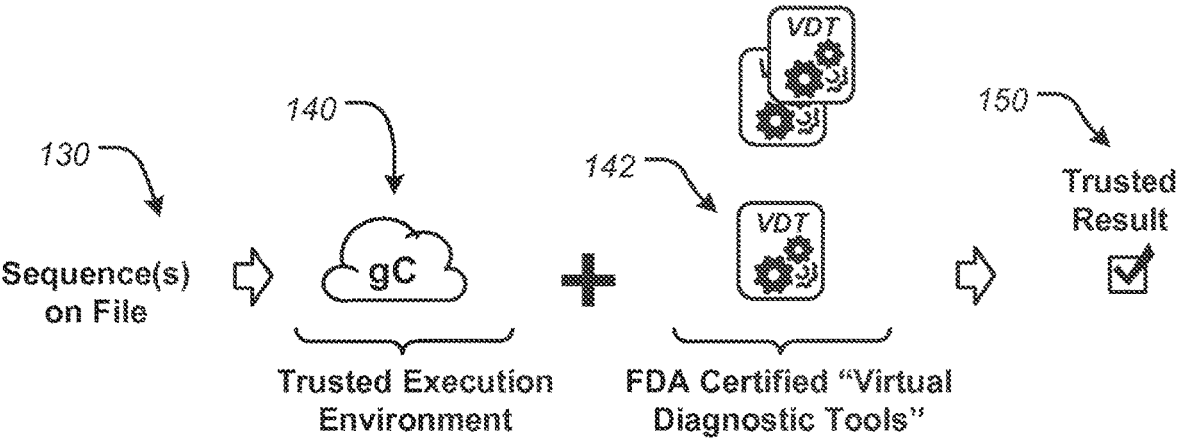

FIGS. 1A-1C illustrate a transition from tightly coupled genetic tests using a physical medical device to decoupled sequencing and testing steps, where the testing steps consist of a series of software analyses performed on the original sequence. Here, we refer to these analytical modules as Virtual Diagnostic Tests, or VDTs.

FIG. 1A illustrates how testing is currently carried out, in which testing and analysis are tightly coupled. A patient's sample 110 is directly analyzed using a genomic analysis tool such as a microarray or a "gene chip" 112, which then yields a result 114.

FIG. 1B illustrates a patient's sample 110 being analyzed by a sequencer 120 which yields a sequence output 122. The sequence 122 then can be used for analysis right away. However, the sequence output 122 can also be stored in a computer-readable format. As shown in FIG. 1C, according to some embodiments, a stored sequence on file 130 is processed in a trusted execution environment 140 with one or more VDTs 142 to yield a diagnostic result 150. Note that in the processes shown in FIGS. 1B and 1C, at the time the sequencing is performed (using sequencer 120), the diagnostic tests (such as VDTs 142) may not even be in existence. Therefore, according to some embodiments, both the testing and diagnostic apparatuses should preferably be independently certified to perform their respective tasks securely and accurately, and to ensure that the interface between the two is known and trusted a priori. As new tests are created, these should be properly certified so that they can be authenticated by other users of the system.

Illustrative Design

According to some example embodiments, a system is designed to address trust, privacy, and/or security issues associated with handling sensitive information like genetic data. In some embodiments, some or all of the following features can be included:

(1) Privacy-protected Collection of Genomic Data—In preferred embodiments, even from the genesis of the data—at point of collection—the individual's privacy is protected. Devices output their data directly to the service in encrypted form. The service securely and privately associates the patient information in a way that cannot readily be inferred by lab personnel, or observers of the process;

(2) Data is Anonymous and Protected at Rest—In preferred embodiments, within the system, genomic data is stored in encrypted form, and is de-coupled from information that would reveal the identity of the individual to which it belongs. Access to linking information is closely guarded in accordance with permissions, and the linking information is preferably only used in secure environments for authorized purposes;

(3) Distributed Trust Model—It is desirable ensure that the end-to-end system that produces a diagnostic result can be trusted. Using a distributed trust model, each independent party can be responsible for the part of the process they control, and doctors and end users can trust that the end result is assembled and executed from independently created, but trusted components;

(4) Certifications for Healthcare Use—In a rapidly evolving field such as genomics, it is not reasonable to expect doctors to be able to follow every new discovery and translate research into easily ordered diagnostic tests. By codifying tests and securely associating descriptions and recommendations for use, this gives doctors a simple method for specifying tests. Furthermore, allowing industry and regulatory organizations to certify and co-sign tests gives doctors confidence that the tests that they order have been peer-reviewed and will produce medically-relevant results;

(5) Virtual Lab Programming Tools—Standardized functions within a genomic programming language make it easy for researchers to codify their discoveries in easy to use, standardized tests. Standard operations such as DIFF (returns the difference between two genome segments), IF/THEN statements, Boolean logic, pattern recognition, insertion/deletion detection, simplify the programming needed to commercialize discoveries;

(6) Marketplace for IP— Significant amounts of capital, resources, and time are involved with identifying a particular gene sequence and its relation to phenotypes and disease. Some embodiments of the systems and methods described herein provide a mechanism by which those that make such discoveries can be compensated if they so choose;

(7) Trusted System for Collaboration—In some embodiments, a standard means to create and distribute codified search algorithms is provided, thereby enabling discoveries to be easily shared among researchers. Tests of various types can be easily chained together to form re-usable building-blocks that are shared between organizations—for free or for exchange of value; and/or (8) Privacy by Design—In some embodiments, the system is architected in advance to protect the privacy of its clients. By designing privacy protections at the onset, both private and anonymous analyses can be firewalled from one another—thereby enabling both types of uses without compromising either.

Illustrative Gene Cloud Ecosystem

According to some embodiments, a system for the trusted storage and analysis of genetic and/or other information is provided. Embodiments of this system will sometimes be referred to herein as a "Gene Cloud". In preferred embodiments, the Gene Cloud is a system that provides for the trusted long-term storage and processing of genomic (and/or other) data in a manner consistent with privacy and usage policies specified by the stakeholders in those data. It will be appreciated that any suitable configuration of servers and storage media could be used, including without limitation, a single server or cluster of servers, or a distributed collection of heterogeneous computer systems connected by a variety of networks (e.g., such as the Internet, public and/or private networks, and/or the like).

Some embodiments of the Gene Cloud may include or support some or all of the following: (1) Virtual Diagnostic Tests; (2) protected personal genomic data; (3) authenticated and certified data sources; (4) authenticated and certified diagnostic tests; (5) access to genomic data governed by rules; (6) patient-owned data that can be used for medical diagnoses; (7) ability for a patient to authorize access to data for research and the level of privacy required; and (8) ability for a patient to authorize specific tests on his/her genome and specify who may have access to the results.

Figure 2:
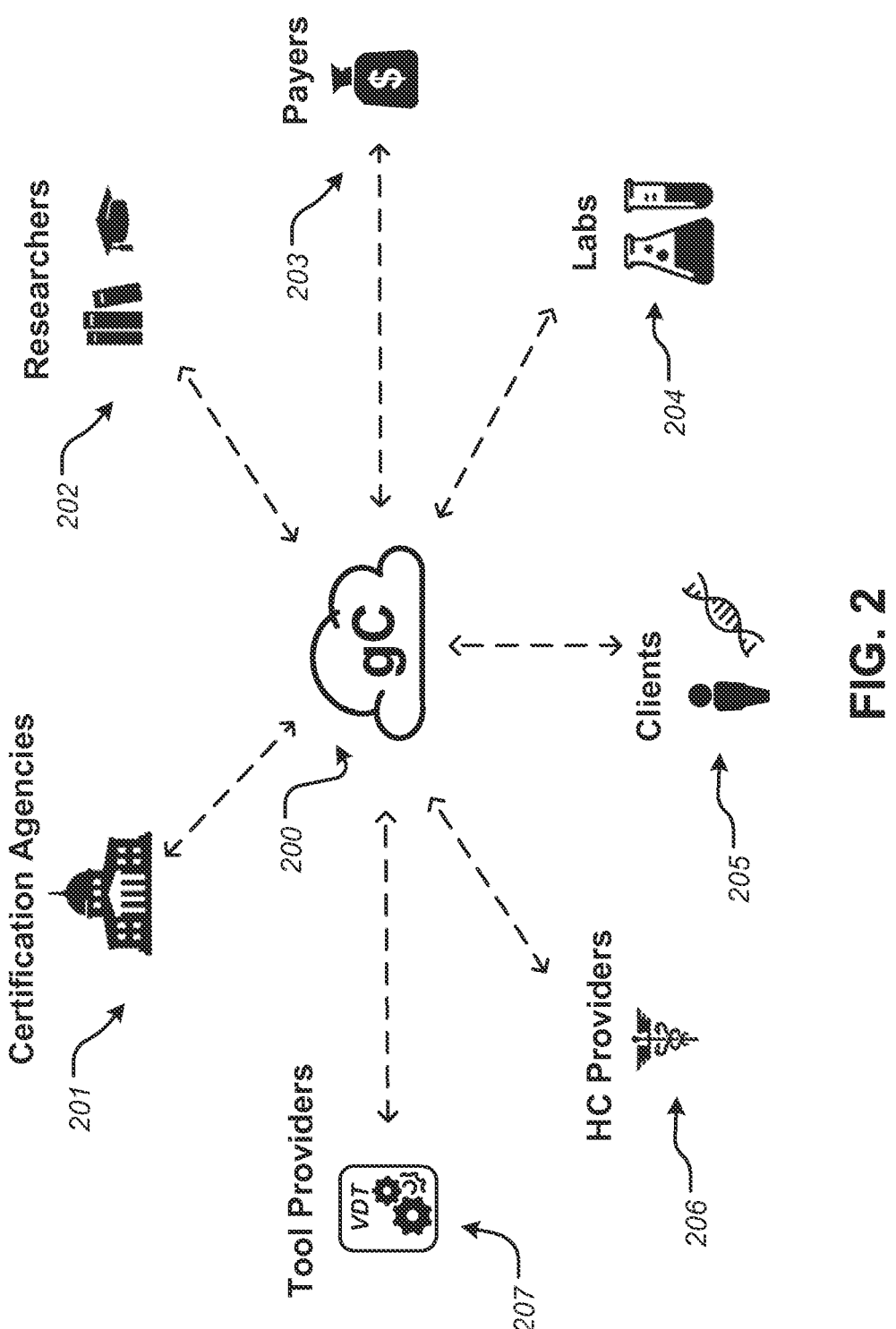
FIG. 2 is a diagram illustrating the potentially large number of stakeholders involved in an illustrative Gene Cloud ecosystem, according to some embodiments.

FIG. 2 is a diagram illustrating the potentially large number of stakeholders involved in a Gene Cloud ecosystem 200, according to some embodiments. Shown as potential stakeholders in Gene Cloud system 200 are certification agencies 201, researchers 202, payers 203, labs 204, clients 205, healthcare providers 206, and tool providers 207. Each of these stakeholders may have a particular set of proprietary interests and concerns in either the genetic data itself or the management and use of those data. Note that the term "client" is used in FIG. 2. However, the terms "client" and "consumer" are generally used interchangeably within this description. Many of the potential stakeholders shown in FIG. 2 play a role in ensuring the security of the data and the integrity of the chain of handling, as shown in FIG. 3.

Figure 3:
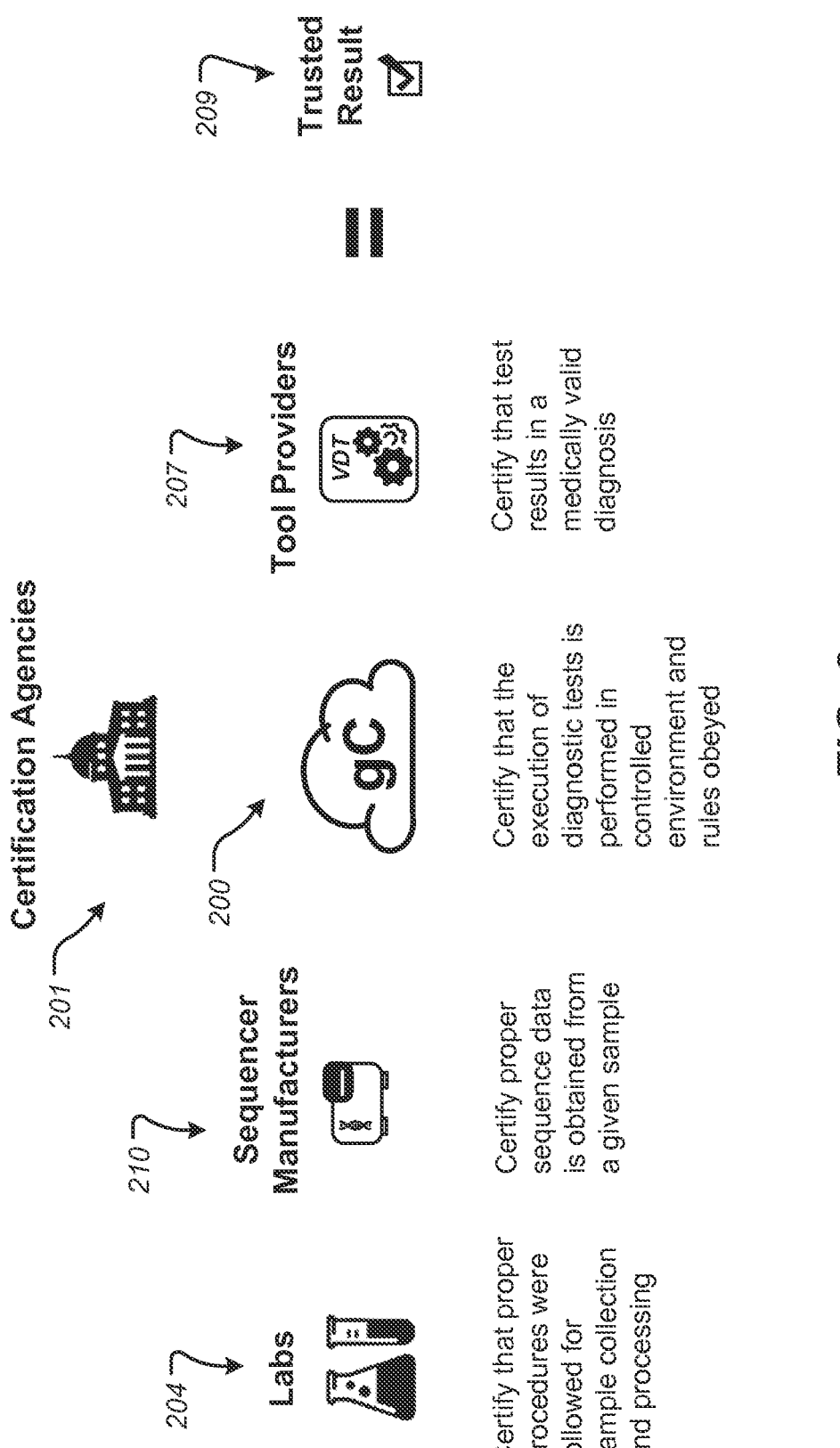
FIG. 3 is a diagram illustrating aspects of ensuring integrity of the chain of handling in a Gene Cloud ecosystem, according to some embodiments.

FIG. 3 is a diagram illustrating aspects of ensuring integrity of the chain of handling in a Gene Cloud ecosystem, according to some embodiments. As shown, a trusted result 209 is ensured by labs 204, by certifying that proper procedures were followed for sample collection and processing; by sequencer manufacturers 210, by certifying that proper sequence data is obtained from a given sample; by trusted gene cloud environment 200 by certifying that that the execution of diagnostic tests is performed in controlled environment and rules obeyed, and by tool providers 207, by certifying that a test results in a medically valid diagnosis. Table 1 describes in further illustrative detail how each of the stakeholders may be involved in the operation of embodiments of a Gene Cloud ecosystem.

TABLE 1

Stakeholder Involvement in Operation of an Illustrative Gene Cloud Ecosystem

| Actor | Role | Examples |
|---|---|---|
| Certification Agencies: | | |
| Medical Trust Authority | Confirms that medical research supports medical claims associated with gene identification and fitness of a virtual diagnostic test for a particular use or diagnosis. Healthcare providers may regard this assurance as a minimal criterion for use in their daily practice. | FDA American Medical Association Society of Genetic Counselors World Health Organization (WHO) Center for Disease Control (CDC) National Cancer Institute National Institute of Health (NIH/NHGRI) |
| Private Trust Authorities | Confirms that tests that have been published by their researchers have been peer-reviewed, are indeed authentic, and have not been recalled. | American Journal of Medical Genetics The Lancet Nature Genomics Whitehead Institute New England Journal of Medicine JAMA |
| Tool Providers: | | |
| Tool Providers | Tool providers create Virtual Diagnostic Tests (VDTs) and other bioinformatics tools for use within the Gene Cloud. The VDTs may, for example, be tests that help doctors determine dosing for a particular drug, or they may be components that are used in a research tool chain. The tool provider will often be required to digitally sign each tool to indicate its source and protect its integrity; these facts will be validated when the tools are executed in the Gene Cloud's VDT execution environment. | Pharmaceutical researchers Academic researchers Bioinformatics tools providers |
| Clients/Consumers: | | |
| Clients/Consumers | Ultimate owner of their genetic information. Sets privacy permissions associated with their data. Approves tests to be performed on their data Periodically reviews the record of accesses to their personal data. | Any person Parents, on behalf of their newborn babies (tested at birth) and while they are legal minors Guardians assigned to manage the privacy of others' genomic information, including fetal genomic information acquired before birth |
| Labs: | | |
| Certified labs | Labs are responsible for ensuring that sample collection, handling and sequencing are performed according to certified procedures. E.g., a university may have a research lab that provides genome sequences for research study; the university's hospital may have an approved medical testing lab. Both may sign and upload data to the cloud for later testing. However, in some embodiments only the latter may be used by doctors seeking to make a diagnosis. | Private research labs Academic labs CLIA-certified labs Other medically-certified labs |
| Sequencing Devices: | | |
| Sequencer Device | The sequencing device is the actual lab equipment that tests the sample and identifies the genomic sequence. In one embodiment, each device that is certified to operate in the ecosystem is given a digital certificate. | Any sequencing device manufacturer |

TABLE 1-continued

| Stakeholder Involvement in Operation of an Illustrative Gene Cloud Ecosystem | | |
|---|---|---|
| Actor | Role | Examples |
|  | Data signed with this certificate authenticates that it came from a device that will properly format the data for use in latter parts of the system.<br>Researchers & Pharmaceuticals: | |
| Pharmaceutical Company (Customer Role) | In a customer role, a pharmaceutical company may pay for access to the consumer data that is retained and managed in the Gene Cloud. For example, researchers may want to:<br>a) Identify portions of the population with certain conditions<br>b) Execute "research bots" within the cloud, with willing participants to map patient history to genetic factors<br>c) Advertise to researchers or doctors who are treating certain diseases<br>d) Locate and invite specific individuals to participate in controlled studies of new treatments | Any pharmaceutical company |
| Pharmaceutical Company (Supplier Role) | In a supplier role, a pharmaceutical company may submit "virtual diagnostic tools" to the system. These virtual diagnostic tools can be, e.g.:<br>Tools to help doctors prescribe drugs which already exist for the general population, but dosing varies by genetic characteristics.<br>Tools to help doctors identify the best possible treatment among a variety of drugs that can all be used to treat a condition.<br>Tools that were mandated (e.g., by the FDA) as a condition for granting approval for a drug. E.g. may only be prescribed for individuals with certain characteristics because it is ineffective or has adverse side-effects for other characteristics | Any pharmaceutical company |
| Academic and Research Institutions | In a supplier role, research institutions may submit "virtual diagnostic tools" to the system. These virtual diagnostic tools can be tools to diagnose genetic sequences that have been identified to be indicators of particular diseases.<br>In one embodiment, if there is a cost associated with performing a test, the gene cloud can process the payment, possibly retain a portion as compensation, and remit the remainder to the submitting institution to help compensate/reward them for their research. | Universities<br>Research Hospitals<br>National Cancer Institute (NCI) |

Gene Cloud Use Cases

Table 2 presents some use cases describing some of the capabilities of certain embodiments of a Gene Cloud system, particularly emphasizing the trust and security aspects of each case. This set of use cases is intended to provide illustrative, but not exhaustive, examples of various Gene Cloud functions in some embodiments of the inventive body of work.

TABLE 2

| Example Use Cases | | |
|---|---|---|
| Use Case | Description | Trust and security aspects |
| Prescription Assistant | A doctor is prescribing a medication for a patient. The pharmaceutical company offers a free tool that helps to prescribe and/or recommend the correct dosage | Doctor needs to trust that the patient's genome record is accurate and was produced by an accredited lab. Doctor needs to trust that the prescribing tool is indeed the most current available (has not been |

TABLE 2-continued

Example Use Cases

| Use Case | Description | Trust and security aspects |
|---|---|---|
| | based on genetic criteria. The doctor selects the appropriate test and applies it to the patient's genome of record. The test result is returned immediately. | revoked), and that it can be authenticated to the pharmaceutical manufacturer and/or a reputable certifying authority (e.g. a private medical association or governmental health authority). Pharmaceutical company may request some anonymous feedback data to help improve dosing guidelines. Regulatory agencies may require use of the tool as a condition for approving the drug. (E.g., tool must be used to prescribe and/or select appropriate dosage) |
| Cancer Treatment Regimen | A doctor is treating a patient recently diagnosed with cancer. Doctor orders a biopsy taken of the tumor and orders a sequencing of its DNA. Doctor orders a "virtual lab test" that a) compares the tumor DNA to the patient's normal DNA and b) compares to other tumors the patient has had in the past. | Since the test the doctor wants to perform compares against previous tests in the patient record that were performed years ago, by different institutions, he wants to determine whether those tests were performed using trusted procedures, and that the integrity of the data can be validated. Since there are several samples, tumor and non-tumor, he must be able to identify specifically what samples he wants to test (e.g., determine the inputs to the tool). The diagnostic tool he runs may actually be a collection of tools that runs other tools to arrive at a recommendation. For instance, the National Cancer Institute may have assembled a "meta test" that runs three tools provided by three different cancer drug manufacturers to determine the treatment with the best chance of success. |
| Pre-natal Assessment vs. "Designer Babies" | A woman is pregnant and the child is at risk for a particular genetic condition. She has an amniocentesis performed and a sample of the baby's DNA is sent to the lab for processing. In society at large, new DNA tests have been discovered for non-life threatening conditions and desirable traits (athleticism, intellect, body size), some of which have doubtful medical support. Despite this, the practice of "genomic pre-birth screening" has begun to emerge. As a result, many governments have enacted controls on what tests and data may be performed and/or disclosed on behalf of the unborn. | Although whole genome sequencing can be performed on fetuses, limits can be placed on what tests can be performed on the sequence data, and there can be restrictions on what information can be provided to those that are acting as a guardians for genetic information associated with a fetus. Although it is not the responsibility of the Gene Cloud to determine what these controls should be, the system is ideally placed to provide a technical solution to enforce whatever societal norms (and laws) dictate. Trust/Privacy controls: Individuals that have a guardian or custodian role may be restricted access to the raw genetic code of the subject, and may be restricted as to which conditions may be tested. E.g. a default may be "no testing," and only signed, approved tests for "pre-borns" may be executed. |
| Newborn Assessment | A woman enters the hospital and delivers an apparently healthy baby boy. As part of the routine health assessment (and as a record for future use throughout the baby's lifetime), the pediatrician swabs the baby's cheek for a DNA sample and sends to the lab for processing. The doctor orders the standard battery of genetic tests that is currently recommended | The pediatrician does not have the time or resources to investigate every possible genomic theory under research. She does not want to be negligent by failing to test, and does not want to overprescribe tests, particularly those that are not well supported. The doctor wants to feel assured that: (a) The tests she requests have been approved by the medical community; and (b) The set of tests that she |

TABLE 2-continued

Example Use Cases

| Use Case | Description | Trust and security aspects |
| --- | --- | --- |
| | by the AMA and the American Board of Pediatric Medicine. | requests are the complete set that is currently deemed to be the standard of medical care. In this example, the AMA does not actually produce any tests itself. Rather, it approves certain tests that have been supported by research and that it believes are medically relevant for the vast majority of births that do not present specific conditions. To assist doctors, in this example, it has created and certified a meta-test bundle that performs a variety of tests (provided by various third parties) that it deems as the minimum standard of care. |
| Research Request | A researcher has developed a tool that looks for specific correlations between sequences and aspects of patient's health. | In this example, the researcher may only be allowed to access the DNA records of those who have granted access. The system only accesses the information within those records that the consumer has authorized (e.g., enforcing a degree of anonymity even when permission is granted for such uses). The test results do not reveal personal data about the "participants" - only the aggregate results. If allowed, the researcher can reach out to interesting individuals in a "blind" manner that preserves the candidate's privacy, but allows them to "opt in" if they desire. |
| Couples Genetic Counselor | A couple is dating and thinking of possibly getting married. Out of curiosity, they want to run a "what if" test for any genetic conditions that could result if they had children together. Since they don't know if they will get married, they don't want to know about the other's genome, just the risk factors that might be presented to their children. They want to run a test that they can believe in, but don't want to pay. They choose a "free" test that was co-signed by the peer-reviewed journal GeneticsToday, rather than the AMA-signed version that doctors use. | Since the test they wish to perform operates on both of their genomes, permission is granted by each person. The test should clearly state who should be able to see the results, and what level of detail should be presented (e.g. only the risk factors, not the source of the risk) |
| Familial/ Ancestry Request | A consumer runs an "ancestry request" to determine the identities of lost relatives, unknown biological parents, or siblings. The test operates on the population that is willing to participate in such queries. In this example, the test results in three sequences that are close biological matches. The originator of the test is given the option to reach out in "double-blind" fashion to determine if there is willingness from both sides to reveal their identity. | Access to identity information is tightly controlled. Identification of the existence of such individuals may be considered a privacy violation in itself, thus, in some embodiments individuals may be given the ability to opt out of the search itself. Request to exchange information should be anonymous to both sides. (The individual receiving the request may not want to know the identity of the requester while deciding whether to answer). Similar to a request to participate in a research study - but both sides may need to remain anonymous. |

Some additional, more detailed examples of implementations of systems and methods embodying various aspects of the inventive body of work are provided below.

Example: Prescription Assistant

A pharmaceutical company has produced a new anti-cancer treatment that has been shown to work on a subset of patients with Alzheimer's disease. The subset for which the treatment is effective share certain genotypical properties—that is, they are genetically similar in certain ways that have been experimentally shown to be related to effectiveness. Furthermore, the appropriate dosing of this drug depends upon the precise genotype. For patients of a particular genotype, overdosing leads to dangerous long-term side effects.

The FDA has approved the drug, but because it is only shown to be effective in a particular class of patients, and because it is dangerous when administered at the incorrect dosage, the agency requires a genetic screening test to determine both likely effectiveness, as well as recommended dosage.

The pharmaceutical company produces a program that assesses these factors and packages it as a Gene Cloud VDT. After the company tests the VDT in the Gene Cloud to verify its proper functioning, the company digitally signs the VDT to assert their authorship. The signature was made using a certified key that was issued by or on behalf of the Gene Cloud for this particular use.

Upon signing the VDT, the pharmaceutical company submits the VDT to an FDA review process. The FDA examines the program, tests it in the Gene Cloud on their own data, and then indicates their approval by digitally signing the VDT with their own certified key, which derives from another root certificate authority (CA) phcontrolled by the FDA. The certificate chain required to validate the signature is packaged with the VDT; the root CA from which the FDA certificate derives is recorded in the Gene Cloud as a "trusted root" that may be relied upon by users.

Once the VDT is approved and has all of its signatures attached, it is uploaded into the Gene Cloud and announced to potential prescribing doctors as being available. The Gene Cloud provides a mechanism by which a clinician can search for the VDT by name and apply it to a particular person's genome.

A patient presents to a cancer specialist for evaluation, and the doctor informs her that he would like to run a genetic test to determine the best course of treatment. The doctor does the following things:

Asks the patient to sign up for an account in the Gene Cloud; through this account the patient will be able to directly control and approve uses of her genome data.

Using his own Gene Cloud account, the doctor requests a unique sequence ID that is to be associated with the patient's sample and prints a barcode label with this sample ID on it. The Gene Cloud notifies the patient, who may approve this transaction.

Takes a blood sample so that the DNA can be sequenced in the lab, packages and labels the sample with the barcode, and sends the sample to the lab.

The lab extracts the DNA from the sample, then sequences and uploads it. The sequencing machine has incorporated a secure module that enables upload of the sample data into the Gene Cloud, and that module provides an interface to the lab technician responsible for uploading the sample.

Upon preparing the sample for sequencing, the lab technician presents a badge to a sensor next to the machine and enters a PIN code. This authenticates the technician and records his identity.

The technician scans the barcode containing the temporary sequence ID, which associates this sequencing run with the sample.

When the sequencing has completed, the technician enters any important metadata associated with the sequencing run. In this case, that the sequencing run proceeded normally and without any machine errors.

The lab technician indicates his approval of the sample upload.

The secure module embedded in the sequencing machine encrypts the data with an ephemeral key that was specially generated for this purpose.

The secure module appends important metadata, such as the lab technician's identity number, the sample ID number, the technician's notes, environmental parameters, etc. and signs the completed package with a certified key that was issued specifically for this device by its manufacturer. The manufacturer's certificate was in turn issued by a trust authority managed by the Gene Cloud.

The ephemeral encryption key is encrypted using the public key of a Gene Cloud ingestion point, which is known to the secure module in the sequencer.

The sequence package is uploaded into the Gene Cloud along with the encrypted ephemeral key.

The Gene Cloud receives the package and immediately verifies its integrity and source. The signatures of the package are checked, and the integrity status and list of signers is recorded for future use.

The private key of the Gene Cloud ingestion point is used to decrypt the ephemeral encryption key, which is then used to decrypt the data. The ephemeral key is archived for later auditing and the data are pre-processed to ensure proper formatting and then re-encrypted with a new key generated by the Gene Cloud.

The Gene Cloud determines the patient to whom the sample corresponds by determining to whom the temporary sample ID was assigned.

The entire sample is assigned a new ID generated by the Gene Cloud; the old sample ID is archived for forensic purposes.

The Gene Cloud sends a notification to both the prescribing doctor and to the patient that the sample has been received. Upon receiving this notification, the doctor uses a Gene Cloud search tool to locate the desired VDT and requests that it be applied to his patient's genome. He may or may not request that the results be visible to the patient.

The Gene Cloud generates a request to the patient (or the patient's designated caregiver) asking for approval to run the test. The approval request lists, in layman's terms approved by the FDA, the purpose of the test and the identity of the person who requested the test. Alternatively, the patient may have indicated her relationship with the doctor and given him prior permission to run such tests.

Once the patient approval is cleared, the VDT is executed. This involves verifying that the VDT was approved by the appropriate authorities, verifying the authenticity of the data to be operated upon, decrypting the data, and running the VDT program.

The results of the VDT are returned to the requesting doctor, and an audit record is generated and stored. The patient receives a notification that a test has been performed, along with an indication of what the test was, who ordered it, and so forth. It may or may not include the test results, depending on how the doctor configured the VDT request.

The doctor evaluates the VDT result and makes the appropriate prescription.

Example: Tumor Classification and Treatment

This example has two parts. In the first part, a research group is attempting to classify breast cancer tumors into classes that respond differently to various pharmaceuticals. Their goal in this research is to identify the classes based on genotype and information about the response to various treatments.

In the second part, a doctor is treating a patient recently diagnosed with cancer. The doctor orders a biopsy taken of the tumor and orders a sequencing of its DNA. The doctor orders a "virtual lab test" that compares the tumor DNA to the patient's normal DNA, and compares the tumor to other tumors the patient has had in the past. Based on these comparisons, the doctor prescribes a treatment regimen appropriately adapted to the patient's genotype.

Turning now to the first part of the example, in which a research group is attempting to classify breast cancer tumors, the researchers have a hypothesis that identifies a set of seventy-five genes as possibly being involved in the biological mechanism of the cancer. Their goal is to evaluate as many patients as possible for information that will help them learn to classify these tumors into groups that are responsive to various therapies.

The researchers create a series of bioinformatics programs to run in the Gene Cloud:

The first helps to identify the cohort under study, which in this case is defined as the set of patients who are: (a) female, (b) have been diagnosed with breast cancer, (c) have been treated for breast cancer with one or more of the drugs under investigation, and (d) have data indicating how well they responded to those treatments. This program is based on information about the patients' phenotypes, which are assumed to be stored in (or accessible to) the Gene Cloud in this example. This first program is referred to in this example as the Selector because it helps to select the cohort that will be used in the experiment. The Selector may, for example, choose half of the eligible cohort as a learning group, and reserve the other half for testing purposes.

The second program is designed to operate on a set of genomes (e.g. normal cells, tumor cells) from a single cohort participant in isolation—i.e. no particular instance of this program accesses the genomes of all of the participants. This program evaluates the normal genome and the tumor genome for the seventy-five target genes, noting the variants for each. The variants include information such as SNPs, early stop codons, copy number variations, etc. This program is referred to in this example as the Gene Profiler.

A third program takes as input the results of all of the individual Gene Profiler runs and derives data to be used in the classification. Although any of a wide variety of different classification algorithms could be used in this program, the general idea in this embodiment is that the algorithm attempts to group patients that respond well to a specific treatment into clusters. In evaluating a novel genome that was not used in learning the classification, then, one would determine which cluster that novel genome fell into, thus predicting which course of treatment might be most appropriate. This program is called the Classification Learner in this example.

A fourth program, the Workflow, is more of a declarative document that describes how the Selector, Gene Profilers, and Classification Learner fit together. For example, it may specify that the Selector will determine the cohort; and that the genomes associated with that cohort are to be input (on an individual basis) to a set of Gene Profiler instances, the output of which is directed to the Classification Learner.

The researchers upload these programs into the Gene Cloud as a Secure Research Request (SRR), a form of VDT request. The research experiment begins to execute, starting with the Selector, as specified in the Workflow.

The Selector runs in a trusted execution environment that ensures that it has access only to the relevant phenotypical data, but no genome data. The Selector identifies a set of 1200 patients that meet the criteria specified in the Selector.

As each potential cohort member is identified and added to the study, the Gene Cloud uses the user ID (or medical record ID) of the member to look up the unique genome sequence identifiers of the genomes (normal and tumor) associated with the patient. In this example, the user ID to genome ID mapping is performed by the Gene Cloud and is not visible to the Selector or to the Gene Profilers, thus preventing the entire workflow from associating personal identifiers with genomes.

The Gene Cloud verifies that the policies of the potential cohort member are consistent with the uses that the researcher wishes to make of their genome data. For example, the Gene Cloud checks that the patient has granted permission for their genome data to be mined for research uses. Some patients may wish to allow any research use, but others may require that the researcher be affiliated with an academic or public health institution and not a commercial entity. Still other patients may wish to be invited to explicitly approve each research use, and may in fact expect to be compensated when their data participates in a research study.

For each cohort member whose policy allows participation, the Gene Cloud creates one instance of the Gene Profiler and makes the normal and tumor genomes available as input to that instance.

Each instance of a Gene Profiler is assigned a newly-generated random ID by the Gene Cloud. This random ID is used to identify the cohort member without revealing any information about the cohort member.

As with the Selector, each Gene Profiler runs in a trusted execution environment that limits access to resources, including databases, storage, and network. For example, a Gene Profiler may be prevented, for example, from making an HTTP request and posting genome data to a third party site. It may also, for example, be prevented from accessing phenotypical data, as well as genome data that were not explicitly assigned to it by the Gene Cloud.

There are several ways in which the input may be made available to the Gene Profiler program. In this example, the Gene Profiler is told that it has two genomes as arguments, one for the normal cells and one for the tumor cells. Using reference identifiers provided by the Gene Cloud, the Gene Profiler requests sequence data for the seventy-five genes in question. These are provided to the Gene Profiler without revealing the genome ID, thus preventing the Gene Profiler from leaking genome ID information that might later be combined with other information to identify a specific cohort member.

As the data are provided to the Genome Profiler program, they are audited and subjected to any relevant user policies that may govern that information. For example, a particular user may have specified that the status of her BRCA2 gene is not to be revealed to anyone, for any purpose. A Gene Profiler requesting this datum, then, would be denied and must then decide how to react, by, for example terminating or by producing a best-effort result without the requested information.

These data are validated in the same manner as inputs to a typical VDT; this validation may include constraints on the quality or source of the input data, the data format, and so forth.

The Gene Profiler runs on the data it was assigned and produces an answer, which is returned to the Gene Cloud along with the randomly-produced identifier, and passed on to the Classification Learner.

The Classification Learner, which also operates in a trusted execution environment, begins to receive results from various Gene Profiler instances.

The Classification Learner does not necessarily know how many results it should expect to receive. Even in cases where the number of cohort members can be identified, errors in Genome Profiler instances (or policy violations) may mean that fewer than the expected number are actually received. At some point, the Classification Learner must decide to run its algorithm, but in the meantime, it simply collects inputs. In this example, the Workflow specification created by the researcher determines that if the sample size is over 1000, and if one hour has elapsed with no new incoming data, the Classification Learner should be run.

In order to compute its classification data structures, the Classification Learner needs not only the results from the various Genome Profiler instances (which it has now collected)—it also needs information about the cohort member and how the member responded to specific treatments. The Gene Cloud provides APIs to the Classification Learner that allow it to query non-personally-identifiable phenotypical properties using the random identifier assigned to the Genome Profiler as a proxy for the cohort members' IDs. Using this indirect mechanism, the Classification Learner can correlate genotypical and phenotypical information without having access to personally identifying information such as names, medical record numbers, addresses, etc.— only to those properties that are relevant for learning the classification.

The Classification Learner produces an output result for the researcher, containing data structures that can be used to classify new instances of the disease on genomes outside the training set.

Application of the classifier is similar to application of the "Prescription Assistant" described in an earlier example. To test and apply the classifier learned above, the researchers create a new VDT program that incorporates the learned classification information derived above. This Classifier program operates on the genomes from a single patient (and her tumor), extracting the necessary seventy-five gene profile and applying the classification that was learned above.

As in the "Prescription Assistant" case, the VDT (the Classifier program) may be certified by third party authorities. In this case, once the Classifier is tested and its results deemed acceptable, an entity such as the FDA or National Cancer Institute may digitally sign the VDT indicating its compliance with its policies.

Example: Blind Pharmaceutical Screening

Many experts believe that the era of blockbuster drugs is over, and that the future of pharmaceuticals will rely on more precise targeting of therapies to patients rather than on universally applicable drugs. In many cases, a patient's genotype will be used to determine whether a given therapy will be effective. It is of great interest to pharmaceutical companies to locate potential candidates for direct marketing or participation in clinical trials. However, this should be done in a manner that preserves patient privacy.

In this example, a pharmaceutical company has created a genome screening program that determines whether the owner of the genome is a potential candidate for a new anti-psychotic drug. In preliminary research the pharmaceutical company has found that people with a specific genotype respond particularly well.

The pharmaceutical company creates a set of bioinformatics programs:

The first, a Selector program—analogous to that in the "Tumor Classification and Treatment" example—selects a cohort of "all people in the Gene Cloud," since they want as many participants as they can get.

A Screener program actually examines the genomes of people selected for the cohort and emits a number from 0 to 100 indicating the probability that they would respond to the treatment. Like the Gene Profiler in the previous example, the Screener operates on one genome at a time.

A Contact program takes the results of the Screener instances and anonymously contacts any patient whose probability is above 70%, using the patient's preferred contact method (e.g. email, SMS, notification in the site, etc.).

A Workflow program that specifies how all of these programs run together.

The pharmaceutical company creates a research request, and signs and uploads these programs into the Gene Cloud, where they begin to run. The Selector continues to run, and will identify cohort members for further study as they come online.

Initially, the Selector has no matches, because nobody knows about this trial, or has opted to let all of their genome data be mined freely by pharmaceutical companies. In other words, the policies set by the owners of genome information in the Gene Cloud—or more precisely, the lack of policies that would permit the use—prevents the matches from occurring.

The pharmaceutical company posts a notification to a patient community—hosted within the Gene Cloud system or otherwise—that provides a link that will allow interested participants to sign up for this free screening.

The invitation to participate in this screening explains what the test does, and how it may be beneficial to the person tested. It also clearly explains that the pharmaceutical company will not be able to learn the identity of any participants, and that the participants themselves must proactively follow up if they are deemed to be a match to the therapy.

As participants begin to opt in, their user IDs are matched by the Selector. As in the "Tumor Classification and Treatment" use case, these IDs are turned into genome IDs behind the scenes, assigned random identifiers, and then provided as input to individual instances of the Screener.

As the Screeners finish running, they provide their results to the Contact program, which uses the randomly-assigned identifier to request that a notification be sent to each cohort member who is more than 70% likely to respond to the treatment. The Gene Cloud uses the random IDs to look up user IDs, find their preferred contact mechanisms and addresses, and dispatches a generic message indicating how they should follow up if they are interested.

Through this procedure, the pharmaceutical company has identified a suitable group of people for whom its therapy is likely to be helpful, and the patients have received a free screening service without compromising their identities.

Example: Newborn and First Year of Life Assessment

A woman enters the hospital and delivers an apparently healthy baby boy. As part of the routine health assessment (and as a record for future use throughout the baby's lifetime), the pediatrician swabs the baby's cheek for a DNA sample and sends it to the lab for processing. The doctor orders the standard battery of genetic tests that is currently recommended by the AMA and the American Board of Pediatric Medicine. As an added benefit, the pediatrician subscribes the baby to the "First Year of Life" medical alert system.

The pediatrician does not have a lab of her own, neither does she want to repeatedly collect samples from the newborn unless a close examination warrants collecting new samples. She knows that there is a risk associated with some test procedures. Other tests are expensive and esoteric, and the cost associated with them is not warranted in most cases. The doctor wants to be sure that she follows the current best practices as recommended by the AMA. The doctor also want to be assured that she gets notified if any advances in genetic diagnosis find potential problems for her young patient.

The doctor takes a DNA sample from the newborn baby, labels it with a unique ID, and sends it off to the Gene Cloud facility. The doctor defines an experiment for the patient as follows:

Run a high priority scan for the most common problems for newborn babies. This scan will be queued at a higher, more costly priority. The pediatrician accepts the extra cost as a precaution. She wants to know about serious problems as early as possible. She uses the AMA certified program package published under the name "Serious Infant Pathology A." She has used this package before and is quite happy with the performance.

Run a scan for problems that are either less severe or manifest themselves later in life at a lower, less costly priority. She wants to cut cost for things that can wait. No need upsetting the parents adjusting to the new baby with the fact that the baby has a male pattern baldness problem. The programs the pediatrician wants to run are two publicly available third party programs, and one program package of her own making.

Continue a periodic scan on the newborn's DNA sample for newly published programs that fit the description "Infant AND Pathology AND Medium OR High Risk". The life cycle of this program covers the first year of the infant's life. Additional parameters to the experiment specify that if the cost of the scan goes over a certain amount, the program first needs to provide documentation regarding the procedure and disease to the doctor, from whom it then needs to receive permission to run.

The pediatrician takes a DNA sample from the infant patient. The sample is taken by swabbing the cheek of the patient. The swab is tagged with an ID. The ID gives anonymity to the patient. The ID is constructed so that the ID can't easily be traced back to the patient. The pediatrician connects to the Gene Cloud console. Via a series of user interfaces she specifies the experiment she intends to perform on the patient. The certified AMA program is loaded into the context of the experiment, and the signatures of the package are checked. The price options for this package are presented to the pediatrician. She selects the priority option. She calculates that the higher cost is well offset by the benefit to the family.

The swab is sent off to the local Gene Cloud center where the sample is sequenced. The sequence is stored in the Gene Cloud. Later, after the initial commotion has settled down, the pediatrician sits down to define the rest of the experiment. She connects to the experiment defined earlier using the Gene Cloud console. She first selects a package made available in one of the major Gene Cloud software marketplaces. The package was created by a retired pediatrician, and signed by his credentials, as well as the credentials of his review group. She knows and trusts the author. Second, she selects a package by one of the older midwives in a different third party Gene Cloud software marketplace. This marketplace is known for having more of a research flavor. The signature of the package is checked as the package is loaded into the context of the experiment. Third, she picks out one of the programs she has created herself. The program is the encoding of her past experiences in practice. In order to upload the experiment she has to provide her credentials to the Gene Cloud along with the credentials of the peer group that reviewed the program.

The sequence undergoes initial processing, including compression and metadata tagging. High priority jobs are run over the sequence as soon as the initial processing is done. The jobs usually have a higher cost associated with them. The high priority job that the pediatrician has specified is now running, even if the experiment is only partially defined. Lower priority jobs now start to run in the Gene Cloud.

The pediatrician now defines the third part of her experiment on the patient, the long running "First Year of Life" experiment. The parameters for this part of the experiment are set. First, only new programs that have the profile "Infant AND Pathology AND Medium OR High Risk" are allowed to run. All programs that have a profile that include "Advertising" in the profile are explicitly rejected with the exception of programs that advertise infant formula, this since the first part of the experiment has uncovered a slight lactose intolerance in the infant patient. This program also helps with the cost of the Gene Cloud analysis since it injects resources into the account for the experiment for every time an advertisement is accepted.

Programs with the profile "Infant AND Pathology AND Medium OR High Risk" are allowed to run provided the cost of running is not prohibitive. Programs with the profile "Infant AND Pathology" are allowed to run provided the following conditions are met:

The cost of running the program is less than 5 cents for the patient's genome.

The cost of running the program is greater than 5 cents for the patient's genome and the program can display relevant research to the pediatrician, and the program obtains the signed permission to run on the patient's genome.

This part of the experiment is set to complete and expire after the baby's first birthday.

Example: Anonymous Offspring Trait Prediction

Alice has had her genetic material sequenced and uploaded into the Gene Cloud. She subscribes to a dating service that is provided on top of the Gene Cloud by a third party vendor. Using the dating service's interface, she selects some traits she would like her offspring to have. One of the traits she would like her offspring to have is the ability to learn from mistakes.

Alice then submits a list of desired non-genetic properties of her ideal mate. High on this list is education, income, and proximity to Alice.

Her genetic traits are already known to the Gene Cloud. Unbeknownst to her she has DRD2 TaqIA polymorphism with genotype AG. Recent studies have indicated that this means that she is much less efficient at learning to avoid errors.

The dating service has encoded these results in regards to the TaqIA polymorphism in a VDT that runs in the Gene Cloud. The program compares two potential candidates and calculates the chances for the TaqIA traits to affect the offspring and to what degree. The program is only allowed to operate on samples from people who have subscribed to the dating service, and whose policy settings allow this use.

A second trusted program in the dating service suite now takes the list of the potential mates and evaluates the non-genetic properties of the individuals. This program is constructed so that the identities and the genetic information of the individuals are kept secret. The program shortens the list of potentials to fit the secondary criteria, and presents the list in a web interface where Alice can access it. Only the degree of matching and information that the potential mate wants to reveal is published.

Alice logs in to the dating site and is presented with a list of anonymous potential mates and the chances that the offspring would possess the traits she desires.

An anonymous negotiation session ensues and Alice narrows down the list of potential mates. Messages between Alice and the members of the list are handled via an anonymous message exchange.

After the negotiation session the parties agree to meet.

Alice repeats the process until a suitable mate has been found.

It will be appreciated that the foregoing examples have been chosen to facilitate an understanding of various embodiments of the inventive body of work, and that the specific details in these examples have been chosen for purposes of illustration and not limitation of the general principles which they demonstrate.

Illustrative Gene Cloud Components and Processes

Figure 4:
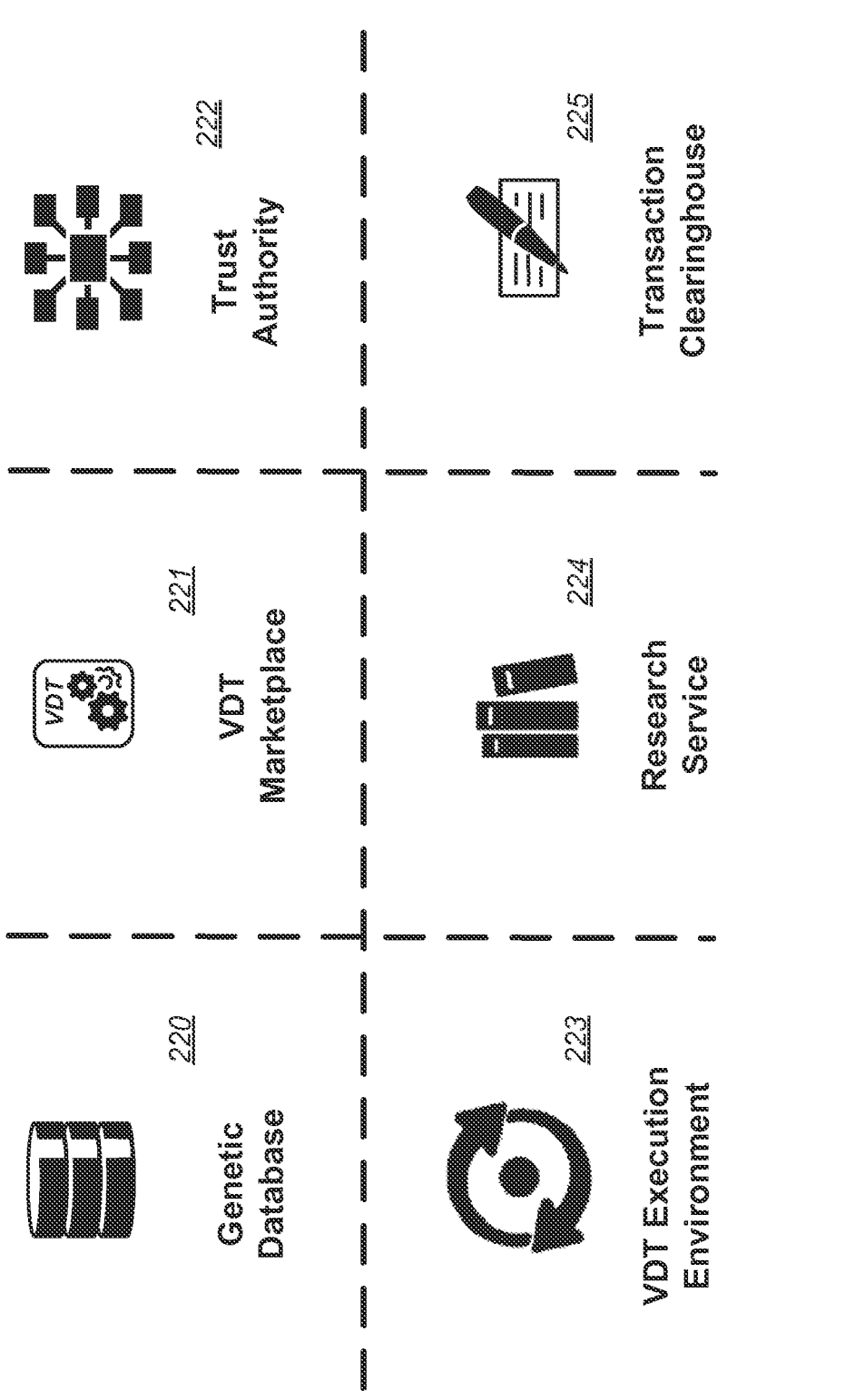
FIG. 4 is a diagram illustrating several subsystems included in a Gene Cloud system, according to some embodiments.

FIG. 4 is a diagram illustrating several subsystems included in an example gene cloud system, according to some embodiments. As shown in FIG. 4, these subsystems may include some or all of the following:

A secure genetic database 220 that stores genomes and other genetic material, as well as other health information that may be relevant to the operation of the system.

A VDT marketplace 221 that allows providers of diagnostic and other bioinformatics tools to sell or otherwise provide access to and/or use of their tools to other participants in the gene cloud ecosystem, such as a hospital that wishes to perform a specialized genetic test on a tumor.

A trust authority 222 that manages the certification of entities that are involved in building the system, providing certified digital identities and keys to participants, potentially including the sequencing machines themselves, doctors, and researchers that wish to access the resources of the system, VDT providers (who would use their certificates to sign their VDTs), and/or the like. This trust authority 222 may, for example, comprise a fully centralized trust authority, a delegated trust authority with decentralized intermediate authorities, or a decentralized web of trust model similar to that which operates in the World Wide Web.

A VDT execution environment 223 that is a secure computing environment where VDTs and other bioinformatics tools are executed. This execution environment 223 can ensure that only trusted, authenticated VDTs are executed and can manage aspects of the computation such as trusted, policy-governed access to the genetics database.

A set of research services 224 that, e.g., allow researchers to inject studies into the system, the components of which will be executed in the VDT execution environment.

A transaction clearinghouse 225 that, e.g., manages payments and/or other exchanges of value within the system.

Gene Cloud Subprocesses. Table 3 describes examples of sub-processes that are involved in the operation of some embodiments the inventive body of work. Operational details relating to these illustrative processes are described in further detail herein below.

TABLE 3

| Examples of Possible Gene Cloud Sub-processes | |
| --- | --- |
| Process | Description |
| Secure Ingestion | The process of securely (and, in some embodiments, anonymously) receiving data into the Gene Cloud |
| Secure Association | The process by which the Gene Cloud associates personal information with genetic data, and discards/obfuscates information that was used during collection that could be used to associate the data with a lab collection sample |
| VDT creation | The process (and resulting format) for a test developer to codify a genetic test, protect it, sign it, determine who may use it, and/or specify a price to use the test |
| VDT Request | The process for a doctor to request a VDT on a patient's genetic data (e.g., may be on one or more samples from one patient or may be on samples from one or more familial related patients) |
| Client Permission Setting | The process by which individual clients set permissions associated with their data. This may, for example, include: a) Setting default permissions for use of their data b) Approving/rejecting ad-hoc permission requests to use their data |

TABLE 3-continued

Examples of Possible Gene Cloud Sub-processes

| Process | Description |
| --- | --- |
| VDT Execution | The process by which the Gene Cloud checks for permissions, checks integrity of data sources, checks certification requirements of VDTs, performs tests that yield diagnostic results, and possibly bills the appropriate party |
| VDT Certification | The process used by certification organizations to append digital signatures or certificates to VDTs, thereby certifying the particular test as having been approved for certain uses |
| VDT Result | The process by which VDT results are returned to healthcare providers to be entered into their patient electronic health record systems. Or, more generally, the process of returning results associated with executed VDT requests or Secure Research Requests. |
| VDT Billing | The process of billing external parties for performing Virtual Diagnostic Tests, and of compensating test providers |
| VDT Marketplace | (Related to the VDT creation process, billing process, and VDT request process) This is the process used by Gene Cloud to display, e.g., the catalog of various VDT tests available within the system, their medical purpose, current certifications, and/or price. |
| GRT Plug-in | The process by which a genomic research tool provider adds functionality of a Genomic Research Tool to the platform |
| SRR creation | The process used by researchers to create a Secure Research Request (SRR). In one embodiment, a SRR by default protects the integrity of the researcher's search criteria and respects the privacy rights of the data that is used. Optionally, the SRR can also protect the confidentiality of the search criteria, and/or can specify that the results must also be confidentiality-protected. |
| SRR execution | The process used by Gene Cloud to execute a SRR. This may include processes for validating permissions to access personal EHR data, permissions to access personal genetic data, collecting and passing the data to the VDT and/or GRT, receiving results and securely storing/passing the results to the researcher. |
| SRR billing | In one embodiment, the process used to bill clients for each SRR (e.g., as part of a subscription, on a compute-cycle basis, and/or the like); may also include the process for paying GRT providers for each use of their tool. |
| GRT Marketplace | The process through which researchers or VDT authors can select various Genomic Research Tools available through the platform. |
| SRR builder | An automated, online "workbench" where researchers can do "what-if" analyses to determine the potential available size of a cohort with specific criteria, and specify what data items they would like to retrieve and pass to a particular tool they have selected. |

Figure 5:
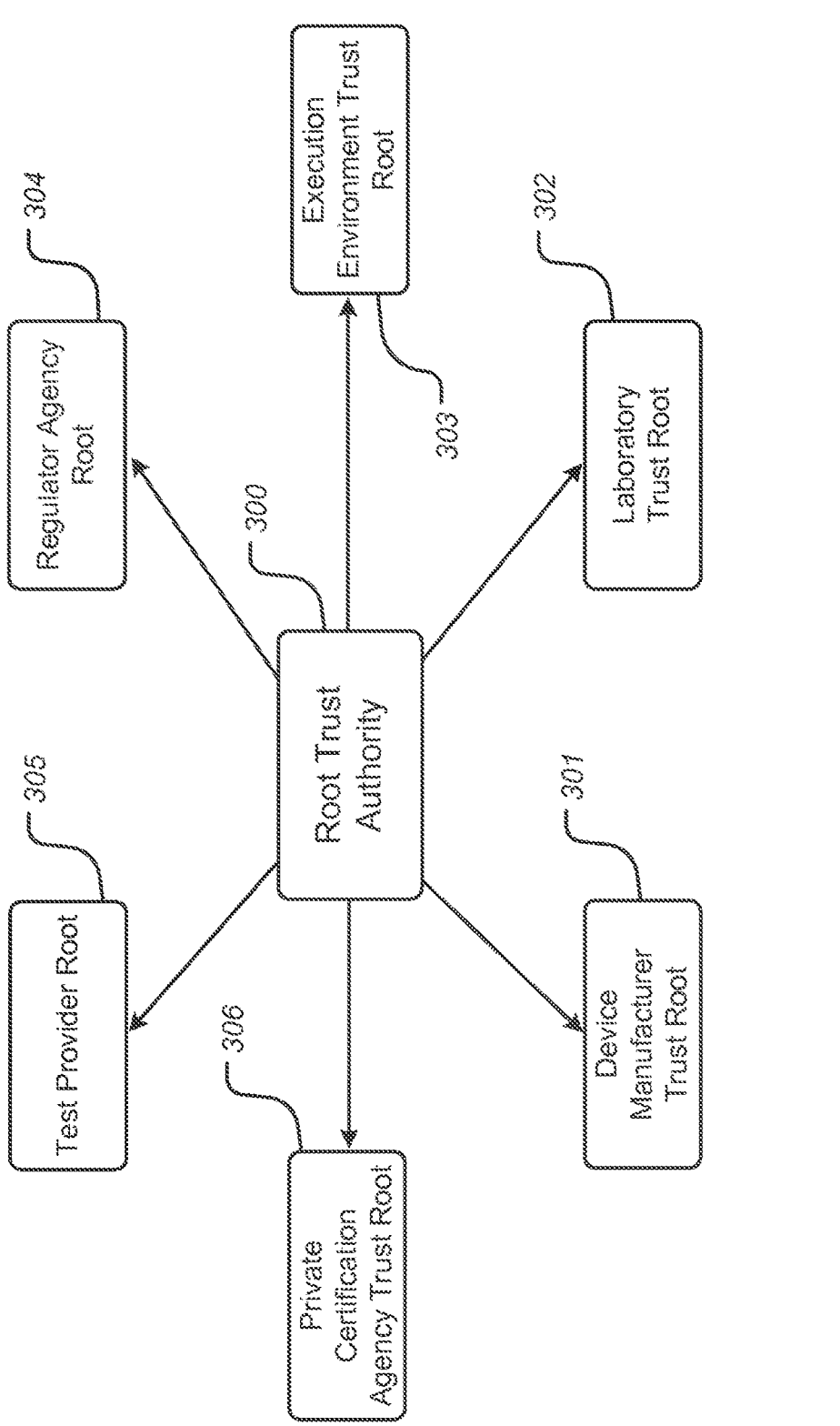
FIG. 5 is a diagram illustrating a delegated trust management approach, in which a root authority delegates operational responsibility for the trust hierarchy to multiple, function-specific intermediate roots, according to some embodiments.

Trust Management. The trust management system described herein is an illustration of one of many possible trust management schemes that may be used in a Gene Cloud system. FIG. 5 is a diagram illustrating a delegated trust management approach, in which a single root authority delegates operational responsibility for the trust hierarchy to multiple, function-specific intermediate roots.

In the example hierarchy shown in FIG. 5, the Root Trust Authority 300 delegates responsibility to six sub-authorities. A Device Manufacturer Trust Root 301 is used to authenticate devices as they communicate information within the Gene Cloud ecosystem. A Laboratory Trust Root 302 is used for authentication of laboratories' human principals involved in handling genetic and other material. An Execution Environment Trust Root 303 is used for signaling the integrity of, for example, VDT execution environments. A Regulatory Agency Trust Root 304 allows government regulatory agencies to sign digital objects within the Gene Cloud system, indicating their approval/review of the object in question. A Test Provider Trust Root 305 is used by providers of diagnostic tools (e.g., VDTs) and other bioinformatics tools that execute within the trusted environment certified under root 303. A Private Certification Agency Trust Root 306 is somewhat similar to the Regulatory Agency Trust Root 304, but is operated by private entities that may wish to signal their approval or review of certain tests, tools, or data.

Figure 6:
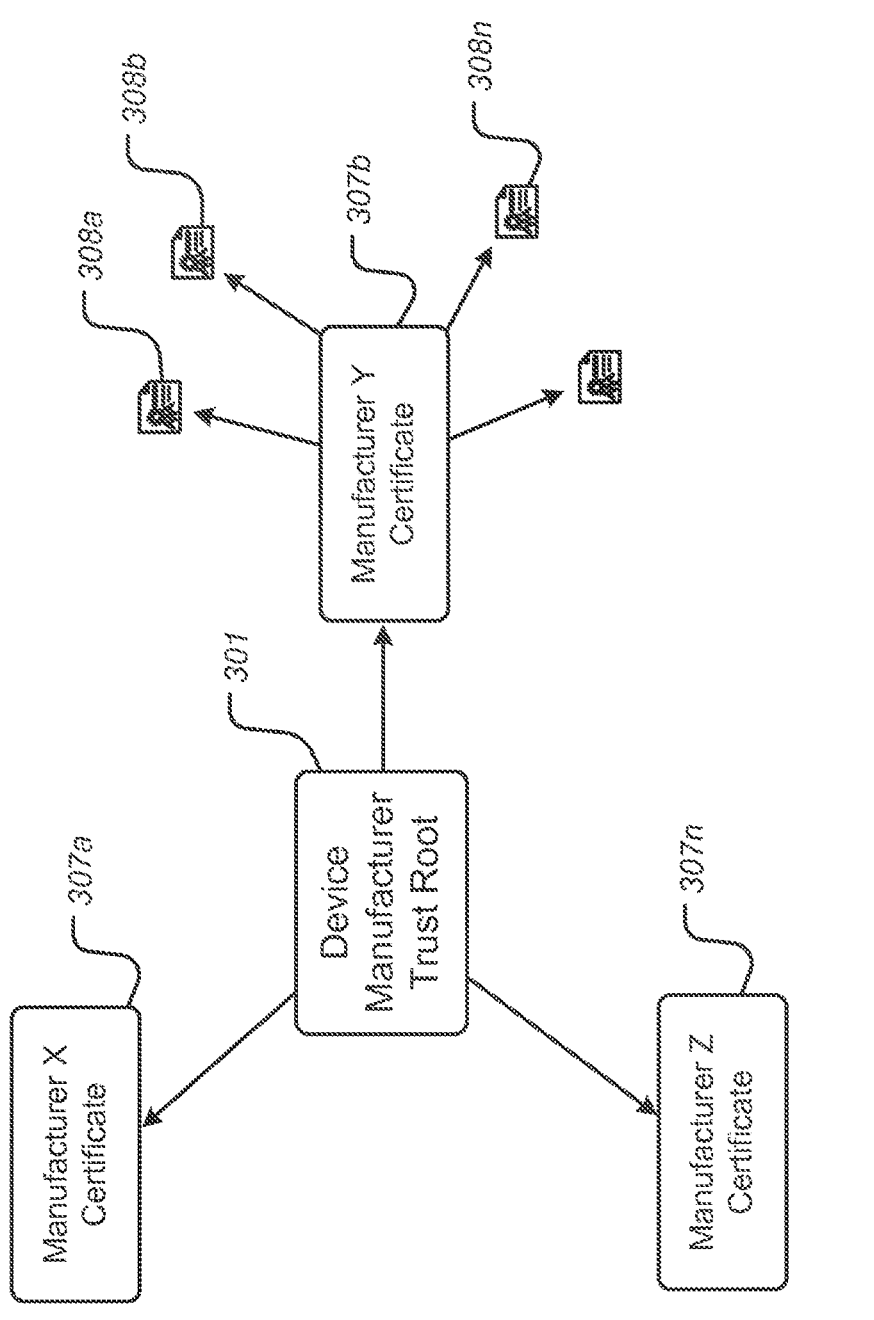
FIG. 6 is a diagram illustrating aspects of an example Device Manufacturer Trust Root, according to some embodiments.

FIG. 6 is a diagram illustrating aspects of a Device Manufacturer Trust Root, according to some embodiments. In some embodiments, the Device Manufacturer Trust Root is a delegated trust authority for certifying devices involved in the Gene Cloud ecosystem, including, for example, devices such as sequencing machines. As shown in FIG. 6, the Device Manufacturer Trust Root 301 may further delegate authority to one or more manufacturer-specific trust roots 307a, 307b . . . 307n, each of which may in turn be used to certify individual devices (e.g. the certificates 308a, 308b, . . . 308n).

Figure 7:
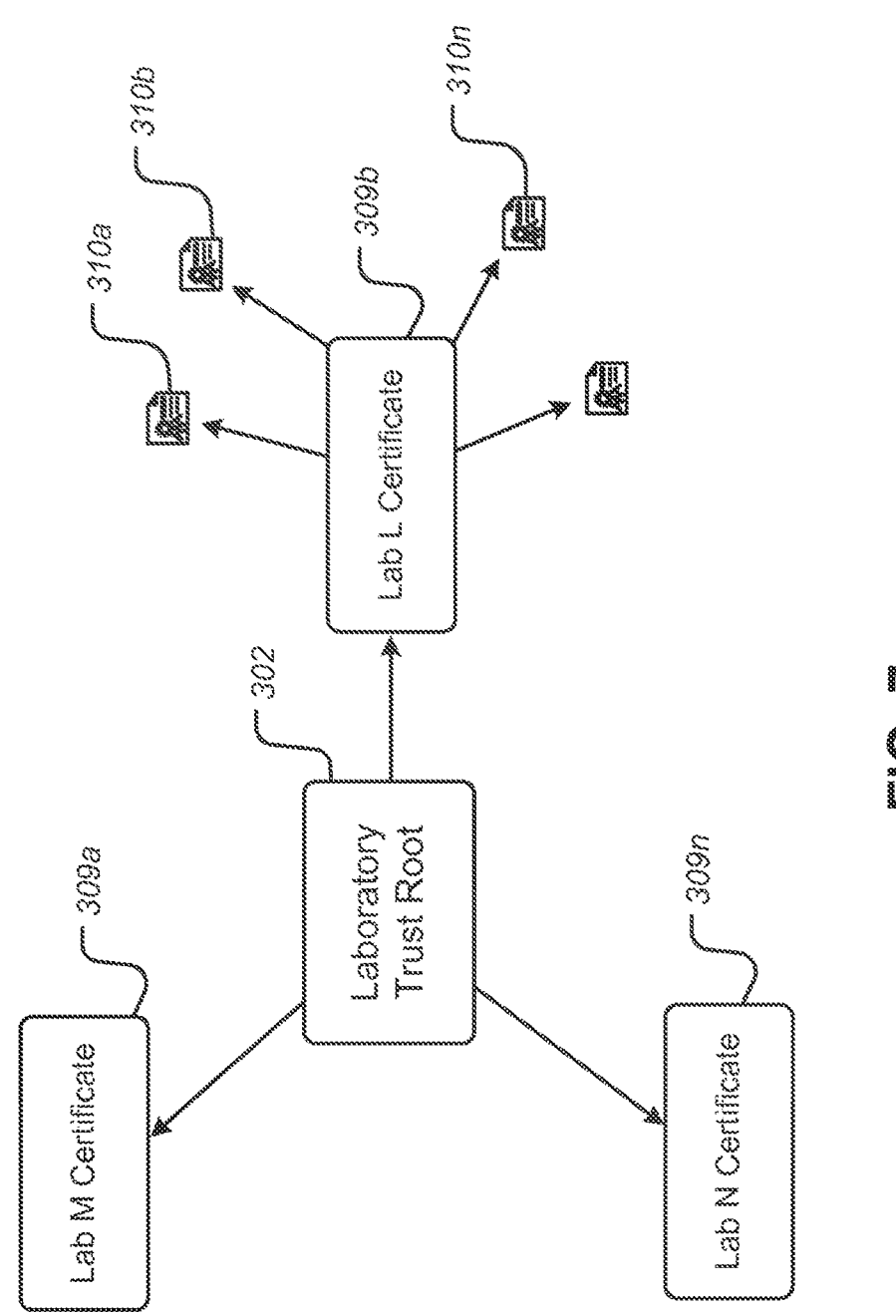
FIG. 7 is a diagram illustrating aspects of an example Laboratory Trust Root, according to some embodiments.

FIG. 7 is a diagram illustrating aspects of a Laboratory Trust Root, according to some embodiments. The Laboratory Trust Root 302 can be used to certify human principals and facilities that are involved in handling secure information within the Gene Cloud ecosystem. As with the Device Manufacturer Trust Root 301, the Laboratory Trust Root 302 can be a delegated root that itself may delegate authority to individual labs 309a, 309b, . . . 309n. Two cases are shown in FIG. 7, one in which the Laboratory Trust Root 302 directly issues end-entity certificates to certify individual laboratories (309a, 309n), and another in which the laboratory itself issues end-entity certificates to technicians and others involved in the operation of the laboratory (310a, 310b, . . . 310n).

Figure 8:
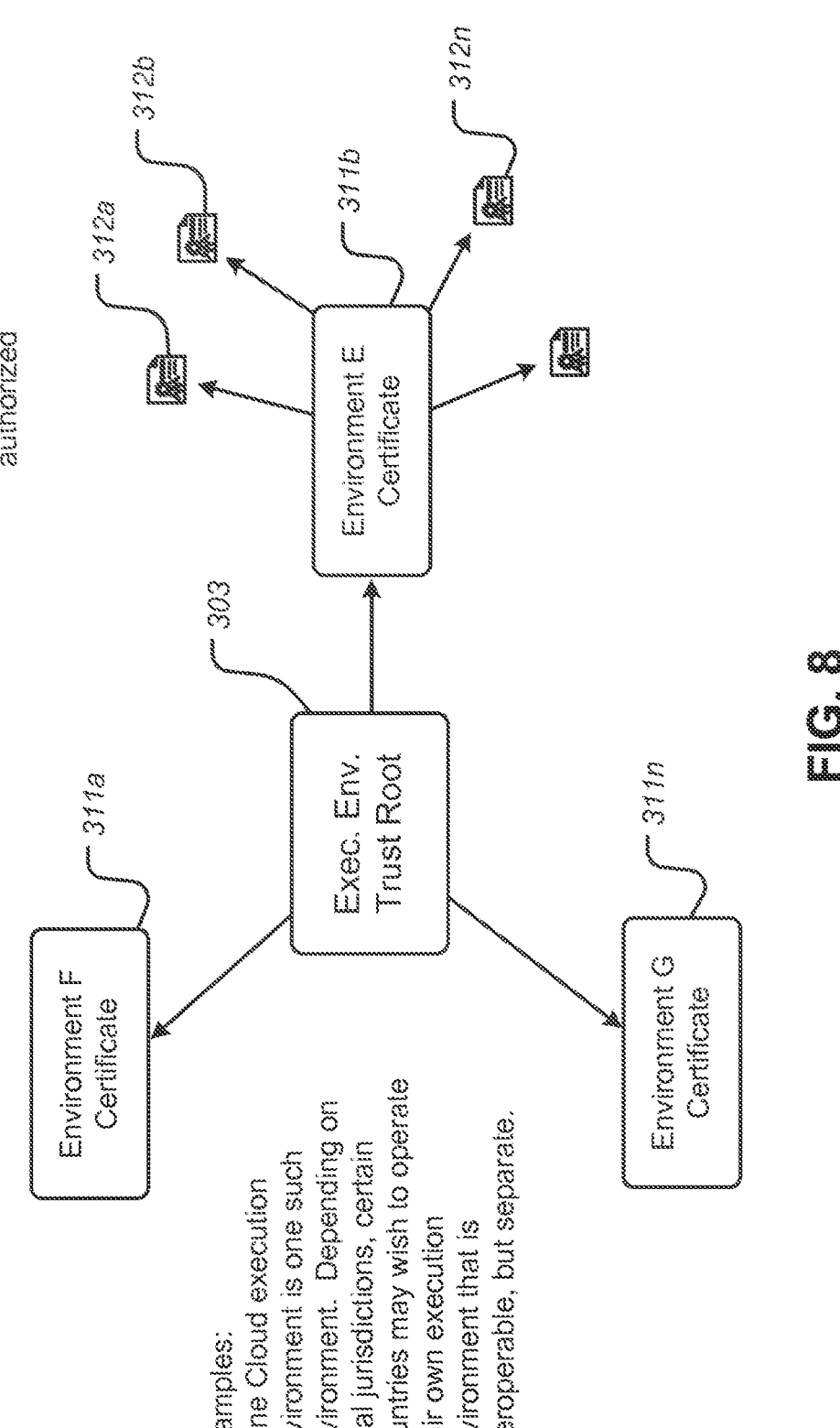
FIG. 8 is a diagram illustrating aspects of an example Execution Environment Trust Root, according to some embodiments.

FIG. 8 is a diagram illustrating aspects of an Execution Environment Trust Root, according to some embodiments. The Execution Environment Trust Root 303 can be used to certify and prove the integrity of the systems that execute tools such as VDTs. In some embodiments, this root may, e.g., authorize different execution environments (311*a*, 311*b*, . . . 311*n*) in different jurisdictions based on local laws, and help ensure that each of the environments so authorized would be able in turn to authorize local "virtual labs" (e.g., actual individual execution environments operating within their jurisdictions). Certificates 312*a*, 312*b*, . . . 312*n* are shown for each "virtual lab" execution environment.

Figure 9:
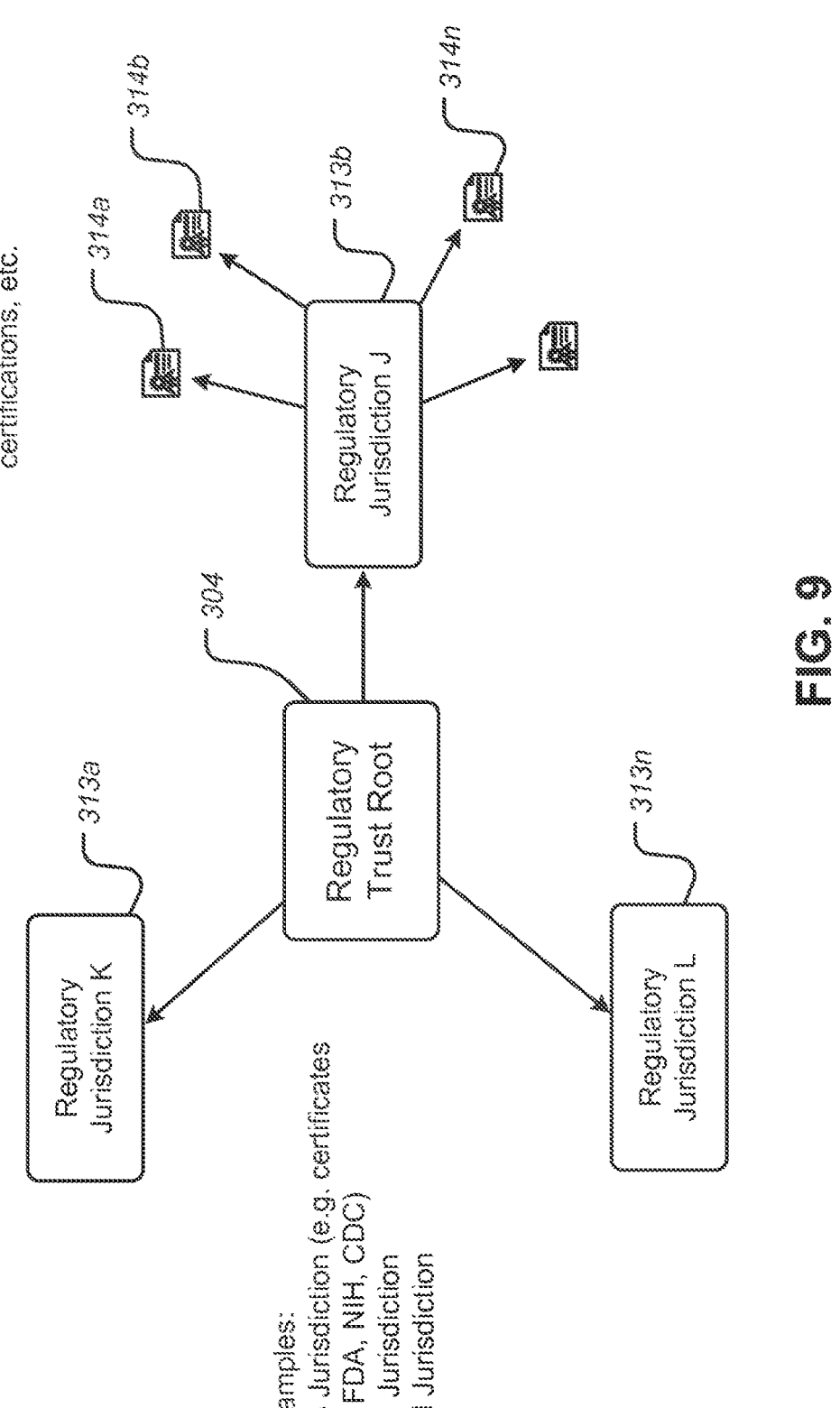
FIG. 9 is a diagram illustrating aspects of an example Regulatory Trust Root, according to some embodiments.

FIG. 9 is a diagram illustrating aspects of a Regulatory Trust Root, according to some embodiments. A Regulatory Trust Root 304 can be used to delegate local regulatory authority to particular legal jurisdictions (313*a*, 313*b*, . . . 313*n*), each of which may independently operate according to local regulations. In some embodiments, these jurisdictions would have the ability to further delegate authority (314*a*, 314*b*, . . . 314*n*) as required in their specific jurisdictions.

This delegated model need not impose any requirements on the several regulatory authorities involved, but rather, can help ensure that systems for the various regulatory jurisdictions are capable of technical interoperability, should such interoperability be desired. Alternative trust models do not involve a single Regulatory Trust Root, but rather allow each system to maintain a list of regulatory certificates that are trusted. This model would more closely resemble the many-to-many trust architecture that is predominant on the World Wide Web.

Figure 10:
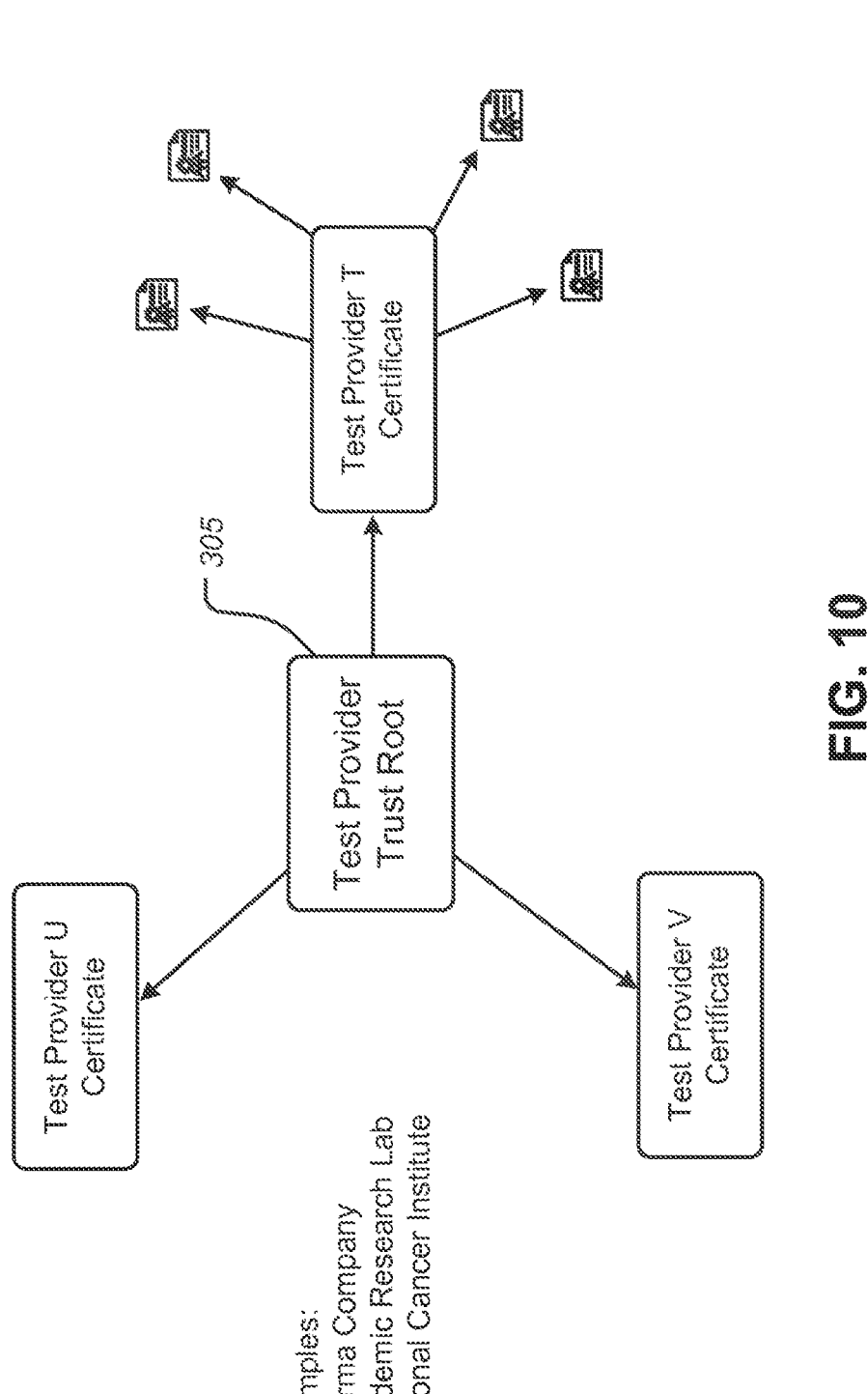
FIG. 10 is a diagram illustrating aspects of an example Test Provider Trust Root, according to some embodiments.

FIG. 10 is a diagram illustrating aspects of a Test Provider Trust Root, according to some embodiments. Test Providers can use certificates derived from the Test Provider Trust Root 305 to assign identities to various actors within their sub-domain, including, e.g., groups within organizations and/or the digital objects that encode the tests (e.g. VDTs) themselves. These various identities can be checked and validated as part of the secure execution of VDTs.

Figure 11:
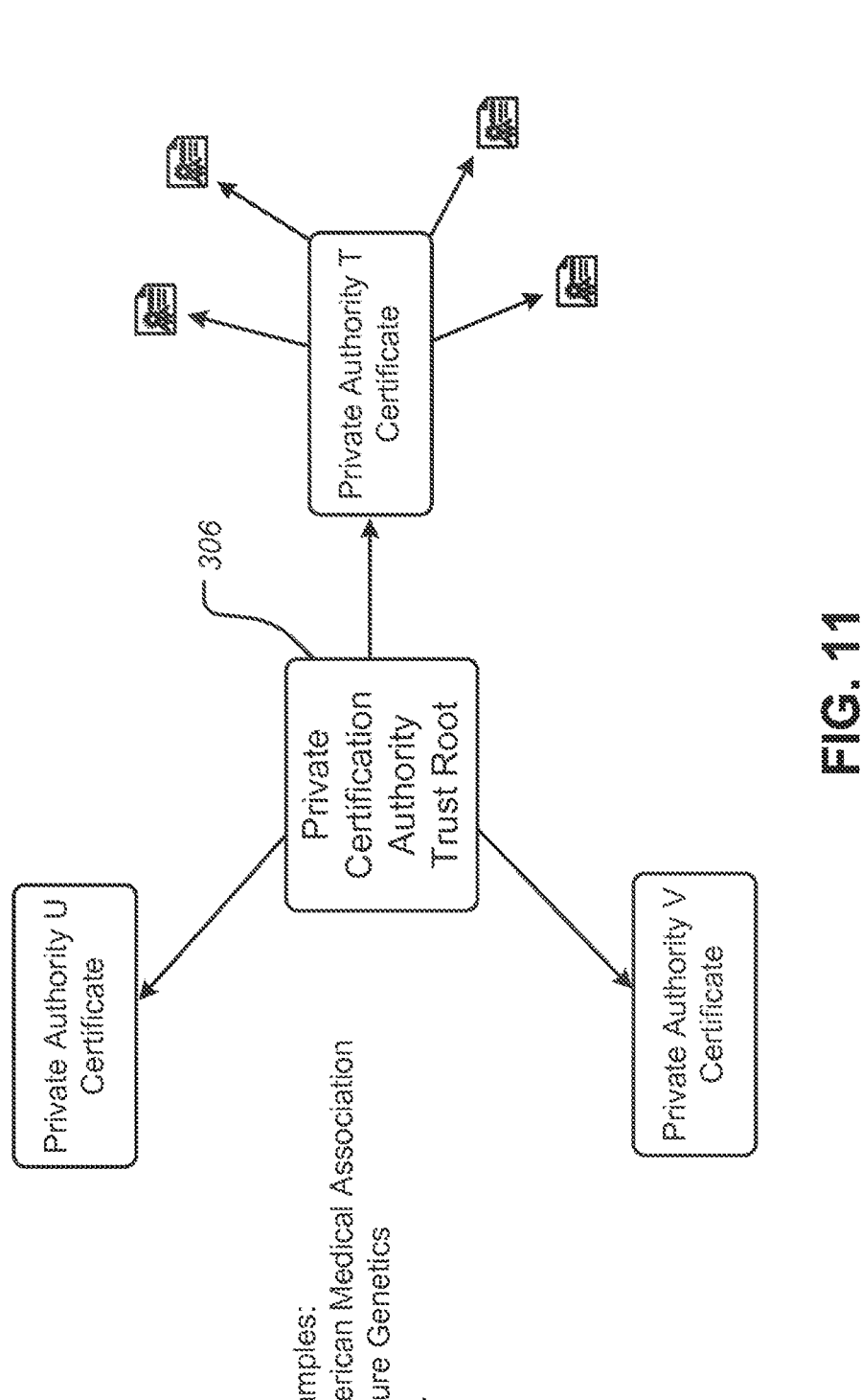
FIG. 11 is a diagram illustrating aspects of an example Private Certification Authority Trust Root, according to some embodiments.

FIG. 11 is a diagram illustrating aspects of a Private Certification Authority Trust Root, according to some embodiments. Much like the Regulatory Trust Root 304, Private Certification Authority Trust Root 306 can be used to provide various entities with the ability to indicate that they have reviewed or approved particular objects such as VDTs, sequences, equipment, etc. For example, the CLIA may have a sub-root derived from the Private Certification Authority Trust Root that allows them to vouch for particular laboratory equipment and/or lab procedures that have been certified. A professional association such as the American Medical Association may wish to add their own digital attestation to a particular VDT, indicating that it has been reviewed by the organization, etc. Each private authority would be issued its own certificate signed by the Private Certification Authority Trust Root, which would in turn empower it to issue further certificates as appropriate for its own purposes.

Figure 12:
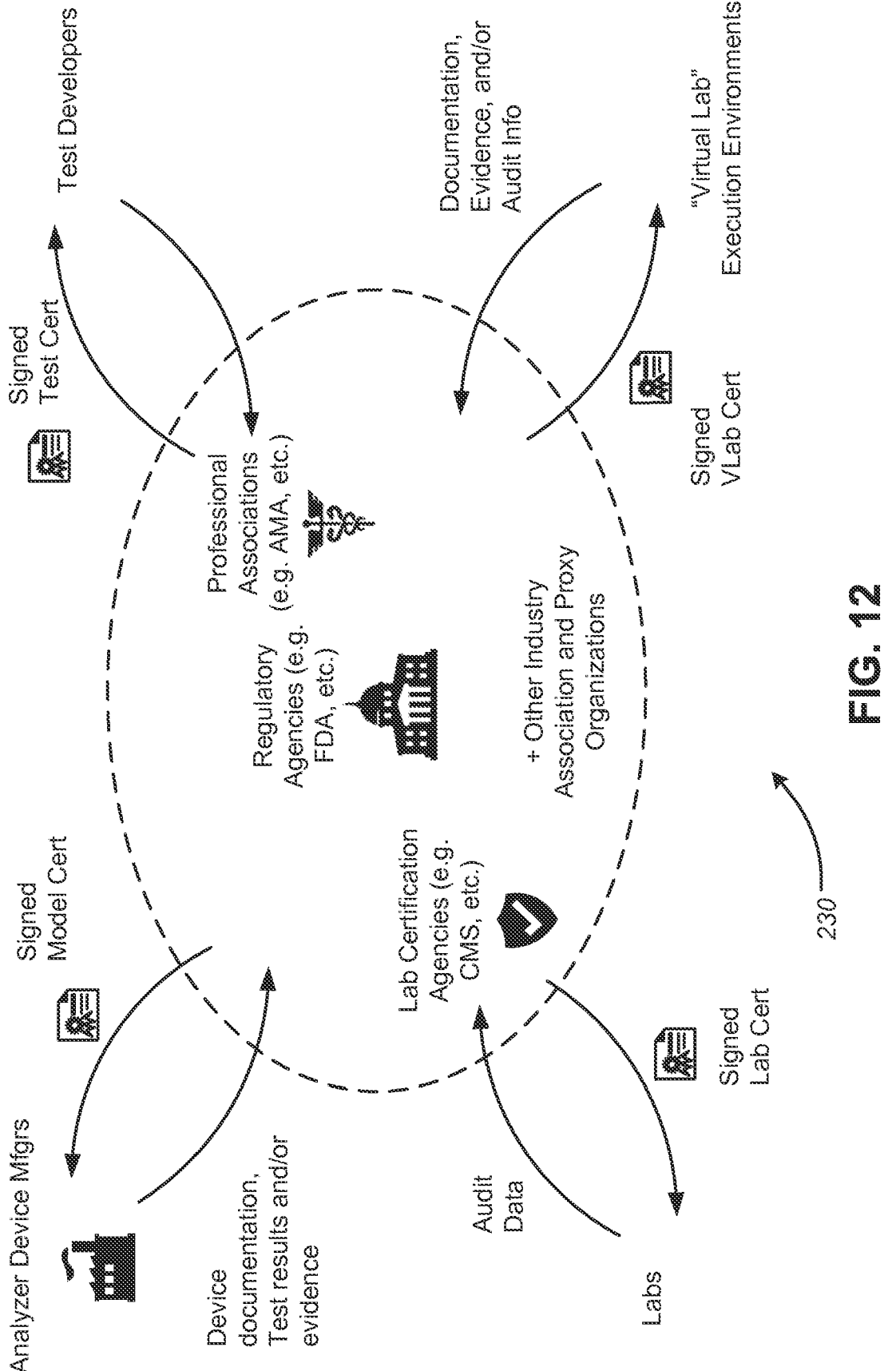
FIG. 12 is a diagram illustrating aspects of example certifications in a delegated trust model, according to some embodiments.

FIG. 12 is a diagram illustrating aspects of certification in the delegated trust model, according to some embodiments. A delegated trust model 230 is shown in which, as described above, each sub-root may impose various requirements for certification within its particular domain. FIG. 12 illustrates some examples of possible certification processes, requirements, and artifacts, according to some embodiments.
Confidentiality and Permissions According to some embodiments, the Gene Cloud system allows researchers and medical personnel to operate on genetic sequences while ensuring confidentiality and privacy for consumers whose data is managed by the Gene Cloud. This section describes some examples of policy mechanisms that can be used in some embodiments.

FIG. 13 is an illustration showing a set of example stages in the lifecycle of genetic information in the Gene Cloud, according to some embodiments. FIG. 13 also indicates some of the objects that are used to maintain security and confidentiality in these embodiments.

Referring to FIG. 13, in Stage 1 (240) genetic information is generated by a sample collection system (e.g., a sequencing machine) in a secure analyzer environment. In this example, the secure analyzer environment—which may, e.g., be a part of the sequencing equipment or in an external unit collocated with the sequencing equipment—possesses a unique device identifier and a cryptographic module to be used to protect sequencing data.

In the example shown in FIG. 13, the sequence data is protected at the source with an ephemeral encryption key (the Analyzer Encryption Key, or AEK), generated locally within the secure analyzer environment. In an alternative embodiment, the ephemeral encryption key is obtained from the Gene Cloud over a secure channel. This key is encrypted with a public key associated with the secure data reception environment of stage 2 (242) and sent to the secure data reception environment along with the encrypted sequence data. A secure analyzer environment may obtain the public encryption keys associated with a given secure data reception environment from a registry that may, for example, associate these keys with other attributes of the secure data reception environments, such as their public IP addresses within the Internet, and/or the like.

During the data generation phase (240), the sample is identified by an ID number (e.g., a SEQID or "sequence identifier") that in one embodiment is a random identifier generated by the Gene Cloud at the point the patient wishes to be sequenced. This random identifier may also be generated in advance of sequencing and delivered to a sequencing center along with the sample to be sequenced. This identifier preferably has no connection to any other patient information, but, in one embodiment, the Gene Cloud maintains the linkage to the patient as a pair of protected link objects (shown as 'SEQ-SAM' and 'SAM-CID' in FIG. 13).

In one embodiment, the first of these link objects associates the ephemeral SEQID with a longer-term identifier for the sequence; the initial SEQ identifier is no longer used once the sample has been ingested into the Gene Cloud—except for strictly controlled internal auditing processes. The second link object associates the particular sample with a Consumer ID (CID). In the course of later processing, this link object is protected from VDTs and other informatics tools in order to maintain consumer privacy.

In one embodiment, the subsystem that maintains the links between various identifiers in the Gene Cloud is referred to as a Secure Association Management System. The Secure Association Management System makes possible fine-grained control over access to anonymized patient information.

Referring once again to FIG. 13, in the ingestion and secure association stage 242, the sequence data is ingested by the secure data reception environment. These data may be transmitted to the Gene Cloud via any of a variety of network protocols, including, but not limited to HTTP (including HTTPS), FTP, UDP-based protocols, and/or the like. In some embodiments, data could be delivered to an ingestion point by physical means (e.g., on a disk drive). There may be a plurality of secure data reception environments available for uploading the sequence data. In general, the secure data reception environments should preferably be located within a highly secure facility (HSF) to prevent unauthorized access and tampering.

In one embodiment, the sequence data is decrypted and the ephemeral key used to protect it in transit is archived for future forensic and auditing uses, but not otherwise used. The SEQID is used to determine the consumer to whom the sequence belongs, and the sequence is stored under the consumer's ID, protected by a new key. The SEQID is maintained as part of the SEQ-SAM link object for historical and auditing purposes, but the SEQID is not used again.

In one embodiment, the use stage (244) for a genetic sequence relies on permissions associated with the consumer account. In most cases, the link objects that bind the sequence identifiers with the consumer ID are not exposed, e.g. to diagnostic tools. Thus, in a preferred embodiment, even if a tool has access to low-level sequence data, it cannot use that information to obtain further information about the identity of the sequenced consumer, including medical or other phenotypic information that may be stored in the Gene Cloud. An embodiment of an illustrative permissions framework is described below.

In one embodiment, a gene cloud system includes a policy management system that is responsible for secure storage and interpretation of rules governing access to genetic, phenotypical, and/or other data. This management system may be provisioned with root policies that are automatically associated with data generated from particular sources, such as specific secure analyzer environments.

The following is an example of how one embodiment of the system might be used: (a) a doctor logs into the system; (b) the doctor queries a patient's record; (c) the patient's CID is looked up and general information is displayed; (d) the doctor browses samples on record for the patient; (e) the CID is used to locate all SAM-CID objects; (f) permissions within the SAM-CID objects are checked for access to sample data, and, since the doctor is part of the medical staff, access is permitted; (g) the doctor selects two samples and selects a test to perform; (h) the secure environment validates the test, unlocks all of the data, retrieves and decrypts the sequence data, validates all of the input data required by the test, and performs the test; and (i) if fees are associated with the test, billing systems are updated with the appropriate charges.

FIG. 13 illustrates an exemplary flow of data through the various secure environments where sequence data is generated, associated with personal and sample related data, and securely processed according to permissions. In the first stage 240, the secure analyzer environment is used to generate, encrypt, and digitally sign the sequence data. The secured data and associated identifiers are packaged within an analyzer data package (ADP) and sent to a secure data reception environment. Information about an additional exemplary embodiment of stage 240 is further described in connection with FIG. 21. Within the secure data reception environment, the ADP data is authenticated, decrypted, and securely ingested into the Gene Cloud system. In this stage (242), the identifiers within the ADP are used to associate the data with a specific Gene Cloud Sample ID and Consumer ID, and the sequence data is transcrypted and stored as a sequence data object (SDO) within the Gene Cloud. Information about an additional exemplary embodiment of stage 242 is further described in connection with FIGS. 24 and 25. In stage 3 (244), sequence data is retrieved, decrypted, and processed in response to search requests and Virtual Diagnostic Test Requests (VDTrx). Accesses to the sequence data and subsequent tests are performed in a secure environment (e.g., a "Virtual Lab") and in accordance with permissions that have been assigned by the owner of the data. An exemplary process for stage 3 (244) is described in further detail in FIG. 16.

Figure 14:
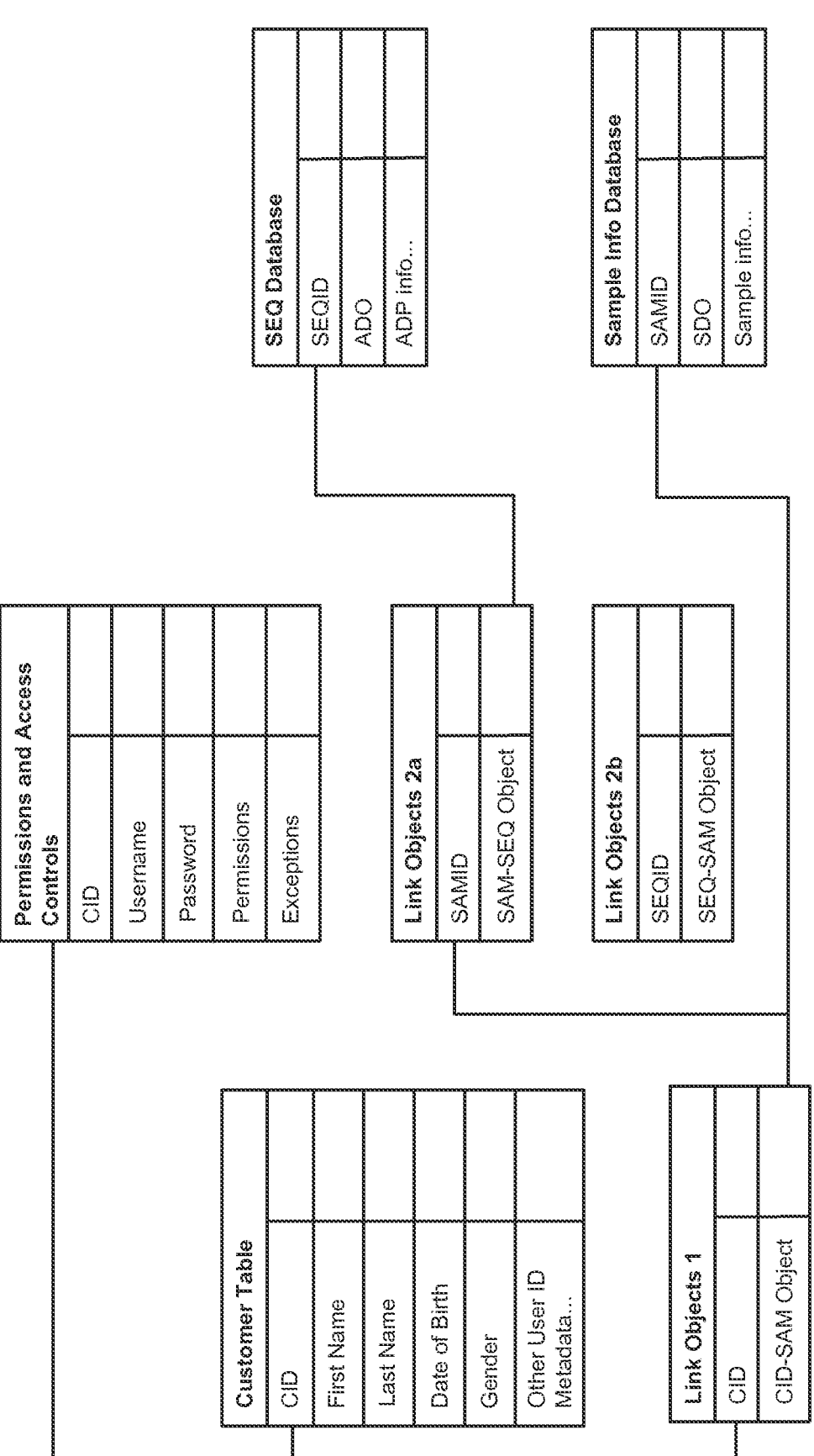
FIG. 14 is an entity-relation diagram showing links between data objects, according to some embodiments.

FIG. 14 is an entity-relation diagram showing links between data objects, according to some embodiments. FIG. 14 provides a more detailed view of the relationships between the various data objects used in one embodiment of the Gene Cloud in order to preserve privacy.

Permissions Framework

This section describes an example of a permissions framework illustrating one way in which patient information can be kept secure in the Gene Cloud. This section is intended as an example; many other types of permissions frameworks are possible. In particular, policy schemes can be used in which permissions are expressed using an executable language such as that described in commonly-assigned U.S. patent application Ser. No. 11/583,693 (Publication No. 2007/0180519) ("the '693 application"), and/or U.S. patent application Ser. No. 10/863,551 (Publication No. 2005/0027871) ("the '551 application")(the contents of the '693 application and the '551 application are hereby incorporated by reference in their entirety). The permissions may also be encoded in a declarative language defined by, e.g. an XML, schema.

According to some embodiments, the Gene Cloud is designed to balance access to genetic information with consumer privacy. In some preferred embodiments, all data are anonymous until they are explicitly associated with a consumer identity and policies are explicitly changed to allow access. This is one type of default policy setting, but others are possible according to other embodiments.

The permissions policies maintained by the Gene Cloud may originate from multiple sources, including, for example: (1) the originator of the data (e.g., an entity that performed the sequencing); (2) laws and regulations in force in the geography in which the sequence is collected, processed, or stored; (3) care providers; and/or (4) patients. In order to apply the appropriate protections to different types of private information maintained within the Gene Cloud, different pieces of information can be classified as one of several possible types according to their sensitivity. A representative set of classes is shown in Table 4, below. The first two columns (marked with a single *) typically represent the least sensitive information, while the last two columns (marked with a triple *) are typically highly private and sensitive and have the most stringent protection requirements. The information in the two center columns (marked with a double ) is typically somewhere in between.

TABLE 4

| | Anonymous Sequence Data * | Specimen Data * | Collection Data ** | Generic Health Data ** | Detailed Health Record Data *** | Personal Profile Information *** |
|---|---|---|---|---|---|---|
| Description | Genetic sequence and attributes | Specimen harvest location; type of specimen | Information about collection process | Generic information maintained by system about client. | Detailed health record information (typically a reference to external systems) | Personal account information |
| Examples | Encoded base calls with quality score; methylation data; other 'raw' genomic information | Organ location, tumor | Date, time, method of collection; sample size, preservation method, lab source | Diabetic, Color Blindness, Blood Pressure, Weight, Approximate Age, Medications taken | Test results, doctor medical records | Name, address, DOB, |
| Privacy Considerations | Although it is unique to an individual, in its anonymous form, it is no different from a computer-generated sequence of a fictitious human being. | Unless the specimen collection location or process is very rare, the risk to privacy is low | Unless an insider reveals exact time of collection and sample volume is low, the risk to privacy is low | Unless there is a very rare condition revealed in the data, the risk to privacy is low | Medical records often contain detailed information such as x-rays, lab results, etc., that may contain personally identifiable information | By definition, revealing the association of this information to genetic sequence information will remove privacy |

*Privacy data classes for information in a gene cloud system*

In one embodiment, for each type of data element, the consumer that owns the data may specify the principals that may have access to that class of data. Table 5, below, shows examples of some of the user permissions that may be defined within a system, according to some embodiments.

TABLE 5

| User | Anonymous Sequence Data | Specimen Data | Collection Data | Generic Health Data | Detailed Health Record Data | Personal Profile Information |
|---|---|---|---|---|---|---|
| Self | Allow | Allow | Allow | Allow | Allow | Allow |
| Guardian | Allow | Allow | Allow | Allow | Allow | Allow |
| Healthcare Providers | Allow | Allow | Allow | Allow | Allow | Allow |
| Researchers | Allow | Allow | Allow | Request | Request | Request |
| Others | Never | Never | Never | Never | Never | Never |

*User permissions matrix*

In one embodiment, once the ability of various users to access the data is established, the consumer (or a proxy acting on the consumer's behalf) may further restrict the specific uses that are allowed with a datum. Table 6, below, provides examples of some of the permitted uses that may be allowed for data in an illustrative gene cloud system.

TABLE 6

| USE type | USES | Description | Examples |
|---|---|---|---|
| U000 | Clinical Diagnosis | Testing of genomic data for diagnostic purposes | Testing as performed in the practice of healthcare for a patient (e.g., a consumer) |
| U001 | Familial Searches | Searches that are intended to reveal familial relationship between the client and others | Parental-child relationships; Paternity Searches; Maternity Searches; Sibling Searches |
| U002 | Donor Compatibility Searches | Searches intended to reveal a list of potential tissue donor candidates that are compatible with a particular recipient. | Eligible bone marrow donors, kidney donors, other organ donors, etc. |
| U003 | Drug or Treatment Marketing | Searches intended to reveal a list of potential candidates to receive a drug or treatment that is commercially available. | Targeted advertising for a drug. |

*Examples of usage permissions in a gene cloud system*

TABLE 6-continued

| Examples of usage permissions in a gene cloud system | | | |
|---|---|---|---|
| USE type | USES | Description | Examples |
| U004 | Research trials | Searches intended to reveal a list of potential candidates to participate in a research trial based on their genomic profile or health profile. | Invitation to participate in a test of a new treatment for a particular type of cancer. |
| U005 | Pre-born approved | Genetic tests that have been approved as medically relevant and/or legally acceptable for use on samples taken from fetuses before birth | Future laws may require that samples from "pre-borns" be categorized as such and restrictions be placed on what types of tests can be performed (e.g., no tests for cosmetic traits that are not deemed to be medically relevant) |

In one embodiment, the consumer permissions are maintained in another permissions table or other suitable data structure, an example of which is shown in Table 7. This permissions table may apply at multiple data granularities in the Gene Cloud. For example, this permissions matrix may be associated with a consumer's entire data set, a particular data privacy class, and/or a particular data element.

TABLE 7

| Example permissions settings | |
|---|---|
| USE type | Permission Setting |
| U000 | Never |
| U001 | Never |
| U002 | Never |

TABLE 7-continued

| Example permissions settings | |
|---|---|
| USE type | Permission Setting |
| U003 | Never |
| U004 | Never |
| U005 | Allow |

In one embodiment, the permissions system of the Gene Cloud allows for the expression of exceptions to the permissions grid to capture variances from a more coarse-grained set of permissions. For example, if a consumer decided to disallow usage U004 for all data by default, he may want to insert an exception to this policy that allows U004 for a particular class of less-sensitive information. An example of an exceptions table is shown in Table 8.

TABLE 8

| Permissions exceptions | | | | | | | |
|---|---|---|---|---|---|---|---|
| UserID | Anonymous Sequence Data * | Specimen Data * | Collection Data ** | Generic Health Data ** | Detailed Health Record Data *** | Personal Profile Information *** | Usage Types Permitted |
| IDXXXXXX | Allow | Allow | Allow | Allow | Allow | Request | U003, U004 |
| IDYYYYYY | Allow | Allow | Allow | Allow | Allow | Request | U003 |

A permissions system with privacy data classes, permitted uses, exceptions, etc. may present a rather daunting level of complexity to average consumers. Therefore, according to some embodiments, the Gene Cloud may contain a set of reasonable default policy templates that allow users to select best practices-based policies via a simple interface. After selecting a particular template, the privacy-related settings described above are automatically assigned by the system as appropriate for the level selected. Examples of policy templates are shown in Table 9.

TABLE 9

| Permissions templates | | |
|---|---|---|
| Template Class Name | Description | Template ID |
| Level 1 - Highly Permissive | This template is for those who are not concerned about privacy, and will allow complete open access to their genomic information and personal information. Note that choosing this level of openness may require formal agreement to waive legal rights to privacy. | T001 |

TABLE 9-continued

Permissions templates

| Template Class Name | Description | Template ID |
|---|---|---|
| Level 2 - Anonymously Permissive | This template is for those who wish to allow access to genomic and personal information to their healthcare providers, but only anonymous access to their genomic information to researchers and other parties. | T002 |
| Level 3 - Cautious | This template is for those who wish to allow access to their genomic and personal information to their healthcare providers, but want to keep their genomic and personal information private from all other parties. | T003 |
| Level 4 - Highly Restrictive | This template is for those who want to restrict access to their genomic information and personal information to everyone, except for healthcare providers that can request access on a case-by-case basis. | T004 |
| Level 9 - Special Restrictions | This is a template that could be used to comply with legal restrictions, such as for fetal genomic testing. This level restricts access to the raw genome data and severely restricts what tests can be performed. For example, to enforce laws related to fetal genomic testing, this template could enforce that only U005 "Pre-born approved" uses are authorized. Unlike other templates that may be freely selected by users, this template may, for example, be enforced as the only option that is available to users of accounts that are populated exclusively with fetal samples (depending on current laws and jurisdictions) or accounts that have been designated as a guardian relationship for samples associated with a "pre-born". | T009 |
| Custom | This is an option for users to select the fine-grained access permissions by themselves, without use of a template. | N/A |

In addition, according some embodiments specific actions within the Gene Cloud, such as running a VDT on a consumer's genome, may trigger an explicit permissions request, an example of which is shown below. In this way, specific uses (as opposed to broad categories of uses) may be authorized by the consumer. FIG. 15 shows an example of a template 252 for an automatically generated authorization request, according to some embodiments.

Design and Execution of Virtual Diagnostic Tests

Executing VDTs. According to some embodiments, executing a Virtual Diagnostic Test (VDT) is a process that comprises four stages: (1) checking permissions—verifying that the VDT is authorized to run against the specific data being requested; (2) authenticating and validating—determining that the VDT itself, and the data objects on which it operates, have been duly validated. For example, in some embodiments, the VDT may be required to be digitally signed to operate in a particular execution environment, and the VDT itself may run only against data with a well-defined, validated chain of handling; (3) executing—running the VDT in the secure execution environment; and (4) output—generating the output of the VDT, which may be, for example, dosing information, copy number variation for a particular gene, etc.

Figure 16:
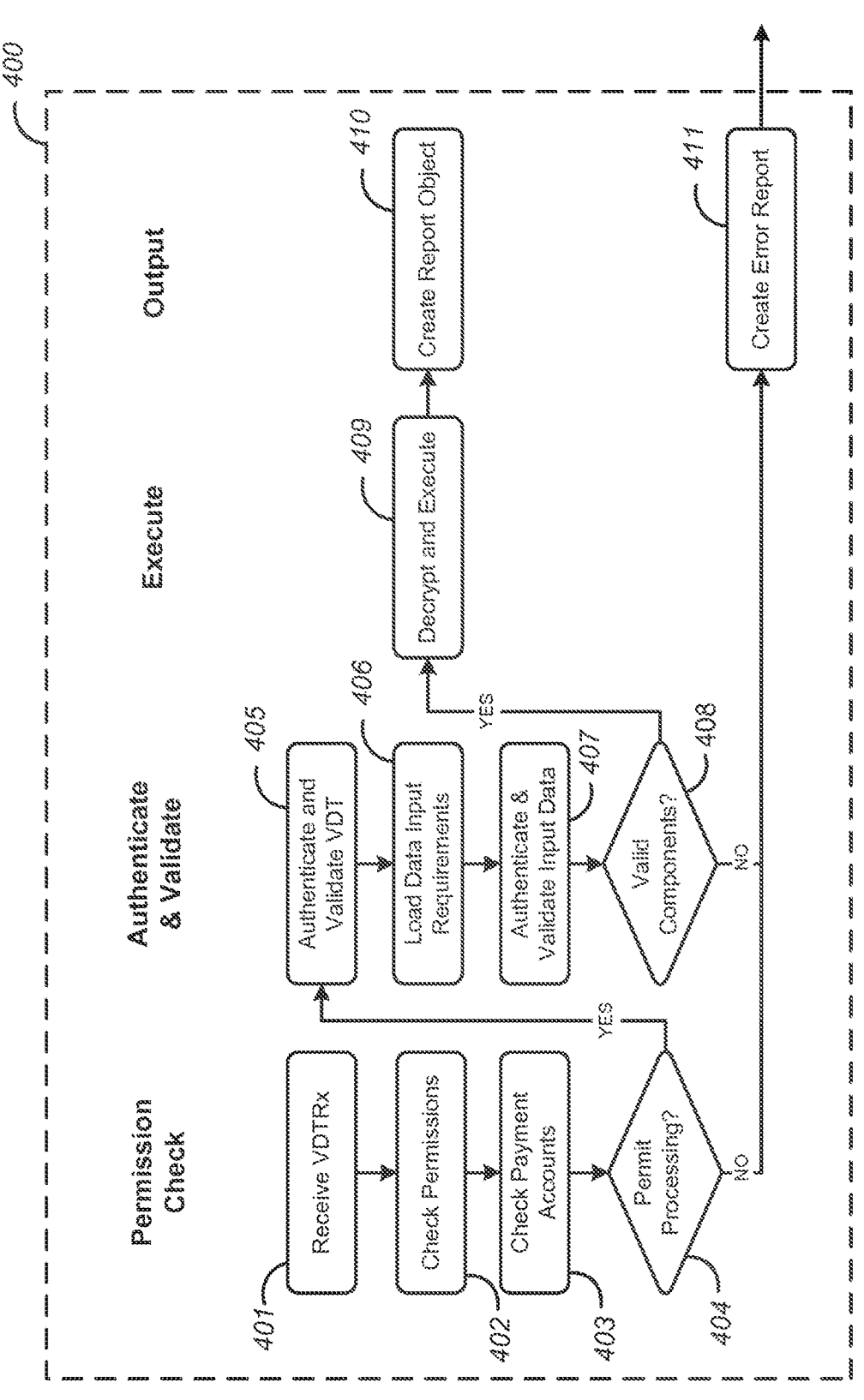
FIG. 16 is a flowchart illustrating actions in a process for executing a Virtual Diagnostic Test (VDT), according to some embodiments.

FIG. 16 is a flowchart illustrating actions in a process 400 for executing a Virtual Diagnostic Test (VDT), according to some embodiments. A person skilled in the art will appreciate that the VDT executed in process 400 is not necessarily a single, monolithic program; it may in fact consist of multiple subcomponents whose activities are coordinated. The term "VDT" used herein should be understood to encompass embodiments in which the VDT consists of multiple components. In such embodiments, the flowchart shown in FIG. 16 may apply to each of the subcomponents of the VDT. At block 401, the VDT request (VDTRx) is received by the Gene Cloud system, indicating that a particular user has expressed a wish to run the VDT against a particular data set.

According to some embodiments, the data set to be used by the VDT is defined by a predicate that depends upon evaluation of phenotypical or genotypical data. For example, without limitation: (1) the input set may be formed by collecting the genomes for all persons of Japanese ancestry that are over the age of 85 and have no family history of breast cancer; or (2) the input set may be formed by collecting the genomes of all people with a given variant of a given gene, and yet who have not manifested a particular symptom; and/or (3) any other selection methodology or criteria.

At block 402, the permissions are checked, using a permissions system. Illustrative examples of such a permissions system are described elsewhere in this document, and include, without limitation, the control and governance mechanisms described in the '693 application and/or the '551 application. According to some embodiments, verifying that the VDT has permission to run may involve the determination of several factors, including, for example: (1) whether the creator of the VDT is a trusted entity, or holds a trusted role. For example, the VDT was created by a particular group of bioinformaticians, or it was created by an academic lab engaged in publicly-funded research; (2) whether the person requesting execution of the VDT is a particular trusted entity, or in a trusted role. For example, the requester is a particular clinician, or is the sequence owner's personal doctor, or is an epidemiologist with a public health agency; (3) optionally, the system may solicit direct permission from the owner of the sequence by contacting the owner through email, SMS, a message posted to a Gene Cloud account, telephone, certified or other mail, or other means. The VDT execution can be blocked until such conditions are satisfied; (4) the VDT may indicate which portions of the genome are to be accessed, and specific permissions for accessing those loci may be checked. For example, a genome owner may opt to completely limit access to the APOE4 gene, which is strongly correlated with the risk of Alzheimer's disease. A VDT requesting permission to this part of the genome would be declined; and/or (5) permission to access a particular genome or subset thereof may depend on the history of earlier accesses to the genome, the amount of personal information revealed, and so forth. For example, the Gene Cloud may refuse permission to access a specific piece of information if that information, in combination with previously-released information, can be used to personally identify the subject. Note that the execution of the VDT may depend upon the consent of multiple parties if it, for example, operates on a collection of genomes owned by different people. The permissions may be collected here at block 402, halting the execution of the VDT until the required permissions are obtained, or the VDT execution may proceed with a subset of inputs reflecting those genome owners whose permission was obtained.

At block 403, if use of the VDT requires payments, a verification can be performed to confirm that the relevant accounts can be billed. At block 404, a decision is made whether to continue based on the foregoing checks. At block 405, a verification is made that the VDT was signed by an appropriate authority under the trust model described above. Although, in this example, this validation is performed explicitly, it will be appreciated that it may be performed implicitly instead or at a different time. For example, the validation may occur when the VDT is uploaded into the Gene Cloud system. Information about that validation—e.g. a record of the entity that created the VDT, a list of trusted entities that have signed the VDT, etc.—may be stored in a persistent cache, which is consulted at block 405. This cached data may be refreshed from time to time to account for expiration of cached credentials and so forth. These types of optimizations do not affect the logical behavior of the system.

The signature of the VDT may be attached in several possible ways, including, without limitation: (1) the VDT may be developed using a client-side tool and digitally signed before it is uploaded into the Gene Cloud; and/or (2) the VDT may be uploaded to the Gene Cloud by an authenticated user, developed and assembled using online tools, and then explicitly digitally signed upon request by the author to tag the official release of the tool. In these cases, the digital signature helps to ensure that the VDT that executes on any given genome was the specified VDT, running without modification.

At block 406, a determination is made of the data requirements as specified by the VDT or by the Gene Cloud environment itself. In some embodiments, the Gene Cloud may impose minimal data authenticity, quality, or other conditions on the source data to be accessed by a VDT. In such embodiments, a VDT author may add additional restrictions that go beyond the environmental defaults.

For example, a VDT may indicate that it will only operate on data that was collected by a particular laboratory. This type of policy is enforced by verifying that the original data package was digitally signed by the requisite laboratory. Similarly, a VDT (or the Gene Cloud environment) may allow data from any lab, so long as the lab was CLIA-certified. Technically, this might be implemented by verifying that the certificate used to digitally sign the original data package was itself signed by an authority such as the CLIA. A more permissive policy might allow any input so long as it is in the correct format, and was generated by a sequencer with a valid certificate.

A VDT may place specific restrictions on the input format, the source and quality of the data, etc. For example, a VDT may require that a genome was sequenced by a machine from one of four major manufacturers, that the models and firmware versions of those machines were the most recent, that the genome has been assembled by a particular algorithm with a given set of parameters, that the sequence was generated based on at least 40× sampling of the raw genetic material, and so forth. In preparing the data for input into the VDT, some embodiments of the Gene Cloud may automatically transform the data into an appropriate input format and log such conversion activities for the output report generated at block 410.

At block 407, a verification is made that any applicable requirements are met, for example, by validating the chain of handling and format(s) for the data to be processed. At block 408, a decision is made whether to proceed based on the results of the preceding blocks. At block 409, if the VDT is encrypted, it is decrypted, and then executed in the secure execution environment. As with VDT signatures, the decryption of an encrypted VDT may happen when the VDT is uploaded into the Gene Cloud, but this is an optimization that may not always be appropriate. For example, if the VDT is sent from one Gene Cloud server to another, encryption may be preserved to (a) protect the VDT in transit and/or (b) authenticate the remote server by limiting access to the VDT encryption key.

During the execution of the VDT, additional permissions may be checked, as at block 402. In cases where the VDT is not specific about which portions of a genome it will access, specific requests for access to the genome may be monitored by the Gene Cloud during VDT execution. This monitoring process may cause the VDT to fail to acquire information it needs to proceed, which may trigger an exceptional case (and, e.g., create an error report at block 411).

Referring once again to FIG. 16, at block 410, the output is prepared for the requester in the form of a report object. Additional reports and audit records may be created for various purposes, including forensic auditing when questions arise as to how a particular genome was accessed. These reports may include, for example, a signed hash of a timestamp, the VDT, the input data, and/or the result. This mechanism allows the Gene Cloud to maintain a trusted chain of handling for the data.

At block 411, in cases where the decisions in blocks 404 or 408 are negative, an error report is created indicating a permissions failure or an exceptional case.

VDT Data Structures

Figure 17:
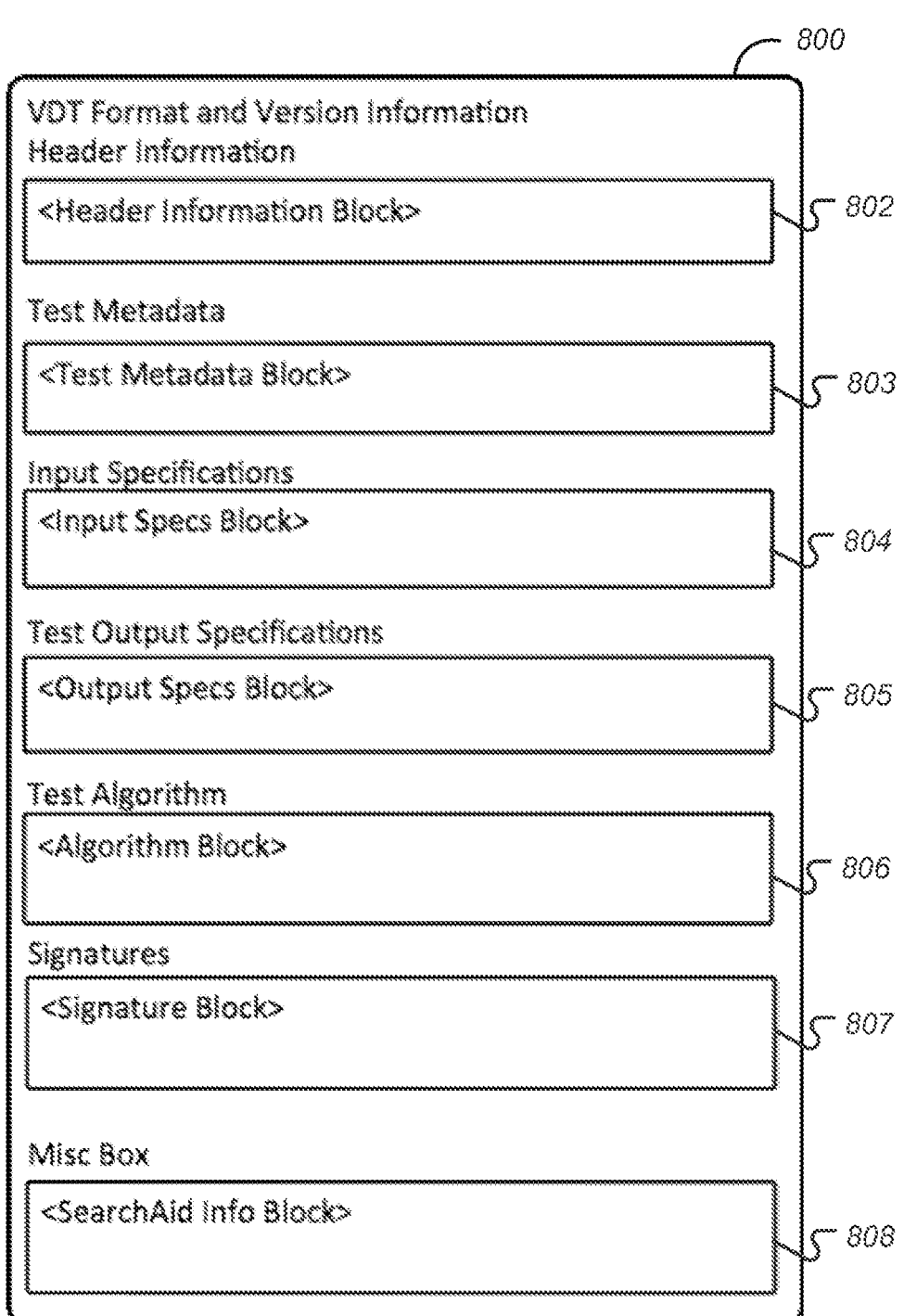
FIG. 17 shows an example of a Virtual Diagnostic Test (VDT) data structure, according to some embodiments.

The examples below illustrate VDT data structures themselves, according to some embodiments. FIG. 17 shows an example of a main Virtual Diagnostic Test (VDT) data structure, according to some embodiments. The example data structure 800 includes several high-level components. A header information block 802, contains information identifying the VDT. Examples of such identifying information includes: (1) UniqueTestID; (2) Test Version; (3) Test Descriptive Name; (4) Publisher Information; (5) Publisher ID; (6) Publisher Name; (7) Author Information; (8) AuthorID; and/or (9) Author Name. Some of this type of information (such as a UniqueTestID, for example) preferably is used for all the tools in the catalog.

Test metadata block 803 includes information that describes what tests the tool is designed to perform, how it is intended to be used, precautions, and/or other such information. This information represents the official, approved description that doctors, researchers, and practitioners will use to determine suitability of the test. It can also include a layperson description for users about what the test reveals, and what cautions to know about before agreeing to the test and/or distribution of the results. Examples of information that might be included in Test Metadata Block 803 in some embodiments include, without limitation: (1) medical description (which can include a short medical description; a long medical description; approved uses; other diagnostic considerations; and/or other disclosures); (2) lay-person description (which can include a short lay description; a long lay description; lay precautions; and/or privacy considerations); and/or (3) use type classifications.

Input specifications block 804 includes information that describes what inputs are needed for the test to yield usable diagnostic results. This may include a textual description for the prescriber of the test, and/or a computer-readable technical description of the expected format and authenticity requirements. In this example, the Gene Cloud will enforce these requirements to ensure that only properly-formatted, authenticated data is fed into the tool. Examples include: (1) input description; (2) input type; (3) expected format and version; and (4) authenticity requirements.

Output specifications block 805 includes information that describes what outputs will be created by the tool. In some embodiments the textual description is important for the prescriber to know, since in some use cases, only a positive/negative result may be appropriate, while in other cases, a detailed report may be appropriate. In some use cases, such as compatibility testing, a couple may only wish to know the risk factors for their offspring, but may not wish to know from whom the undesirable traits originate.

From a technical perspective, this data can be important for "chaining" together various tests to perform a complex "test suite" or "a test bundle". The results of one test may be fed into another test as an input to determine whether further tests should be conducted or may direct which tests should be performed next. Examples include: (1) output description; (2) output type; (3) output format and version; and (4) confidentiality requirements.

In some embodiments, test algorithm block 806 contains the VDT itself. This may be formatted as an executable program, a declarative program, etc.—any format that can be acted upon by the secure execution environment to produce the VDT result. The logic structure shown in the example of FIG. 19 includes a simple function to test for a specific pattern at a specific location in the genome, or to test for a specific base at a specific location. Complex patterns can be stored as a library of pattern variables enumerated separately in a pattern resources block. A variety of tests may be combined using Boolean logic to create composite tests yielding one or more results.

Signature block 807 contains the signatures of the various parties that have created, certified, reviewed, or otherwise attested to the function or quality of this VDT.

A miscellaneous block 808 can be included, which may contain any other data, such as extensions added by particular vendors, etc.

It will be appreciated that FIG. 17 has been provided for purposes of illustration, and not limitation, and that in some embodiments data structures of different formats or types may be used instead, and in other embodiments no such data structure is used at all.

FIG. 18 shows examples of extended metadata, according to some embodiments. Structured data for search aid information 810 and payment information 812 are shown as examples of what may appear in the miscellaneous block 808 of FIG. 17.

FIG. 19 shows an example of a Virtual Diagnostic Test (VDT) algorithm specification, according to some embodiments. The specification 806, is an example of a VDT test algorithm block 806 of FIG. 17. It will be appreciated, however, that FIG. 19 is just one example, and that VDTs can be specified and/or implemented in any suitable form.

Secure Research Requests

In one embodiment, a Secure Research Request (SRR) is a form of a VDTRx (VDT Request) that is tailored for uses related to academic or medical research, genetic search services, etc. In general, the processing and use of an SRR will follow the same procedures as identified for a VDTRx. For most of the use cases for a VDTRx, it is assumed that a doctor, or licensed medical practitioner, is requesting a particular VDT to execute using known inputs associated with one or more patients to which he or she has been permitted access. However, to suit the use cases for research, additional steps may need to be performed to determine which individuals and/or sequences to include in the study, and/or which individuals to invite to participate in a study.

In one embodiment, the process of creating a SRR comprises specifying information about the test to be performed, and identifying selection criteria for identifying inputs. Examples of the types of information that it may be desirable to specify include, without limitation: name of researcher or institution; contact information; identification of affiliated institution(s); purpose of study; duration of study; reason for selection; level of participation required (including, e.g., passive (no additional effort required), active, questionnaire, interview, visit, multi-visit, and testing); use type classification; privacy related considerations (including, e.g., minimum size of study, anonymous participation (Y/N), specific genetic information to be accessed, health record information to be accessed, and personally-identifiable information to be accessed); selection criteria (e.g., genotype selection criteria, phenotype selection criteria, and/or other selection criteria); and VDT set (e.g., a list of VDTs to execute against the sample, or identification of a VDT suite to execute against the sample).

In one embodiment, the gene cloud environment will pre-process the request to determine the number of possible participants and/or the number of possible sequences that exist that meet the selected criteria. In some embodiments, this may involve consulting the database and returning the number of individuals and/or sequences that meet the criteria desired, and for which appropriate permission has been granted (or can be requested) to access the data.

From this high-level data, the researcher can determine the minimum size of the cohort that he or she can include in the study (e.g., those that meet the identified selection criteria, and for which permission has already been granted) and the maximum possible size of the cohort (e.g., also including those that meet the selection criteria, but have identified in their permissions matrix that they would like to be anonymously asked before agreeing to participate). To prevent extremely narrow targeting of individuals that may compromise privacy (e.g., using SRRs for familial searches without properly identifying the use as such), the secure processing environment may optionally impose a minimum number of individuals or sequences that can be targeted as a cohort for a study.

If a researcher wishes to include participants that have indicated in their permissions that they wish to be asked before allowing their data to be accessed for the uses specified in the request, the researcher can request the system to send out invitations to participate on behalf of the researcher. This will ensure that the potential candidates for a study can remain anonymous while they are given the opportunity to participate or decline. Similarly, if the study requires active participation on behalf of the user, the system will provide a facility for researchers to communicate with authorized participants to confirm their consent to participate.

The SRR may be saved by the researcher, and periodically re-evaluated to determine the number of individuals or sequences with confirmed participation and/or permission granted to be included in the study. When the researcher is satisfied with the cohort represented by this subgroup, he or she may submit the SRR for execution and to determine results. In one embodiment, by submitting the SRR the researcher triggers execution of the test with the associated data, which also may trigger a billing event. Billing may be subscription based, or based on a variety of attributes of the search (for example, one or more of: number of individual's records accessed, number of sequences accessed, number of bases searched, compute time, etc.) When a SRR is submitted for execution, it triggers the associated VDT to execute using the processes defined previously, including the permission checking and security related actions that are needed to maintain the privacy and security of the system.

In one embodiment, if a permission to access data is changed by a user between subsequent runs of the SRR, the system will flag this condition and notify the researcher that the size of the data set has changed, and the researcher will independently determine whether to continue to run the test with the revised data set.

In some embodiments, as with other VDT accesses to consumer data, an auditable record of each access is recorded by the system, and is made available to the consumer. In this way, the system is transparent to the owner of the data as to what entities are accessing their data, when, and for what purpose.

Genomic Research Tool

As described above, some embodiments of the gene cloud can provide the capability to execute algorithms of the VDT, however, it can also serve as a cloud-based platform for Genomic Research Tool Providers as well. In some embodiments, a GRT is a tool that may be offered as a plug-in to the gene cloud platform that provides additional capabilities, such as, but not limited to, statistical computation or visualization, machine learning, advanced pattern recognition, etc. Such tools may be offered as default capabilities of the gene cloud platform, or may be offered as a premium subscription, or on a pay-per-use basis. Users such as researchers and VDT authors have the option of selecting these additional tools from the GRT marketplace if additional features are desired, and can agree to any additional fees associated with their use. For example, a researcher may opt for a subscription to use a particular research visualization tool to view VDT results, or a VDT author may agree to a portion of the fee associated with use of the VDT be allocated to a tool provider that is used during the execution of the VDT. To maintain the security and integrity of the gene cloud, VDTs written to utilize such features will still be able to take advantage of the trust management features of the gene cloud, and accesses to data will be made in accordance with the permissions associated with the client data.

Generating and Ingesting Secure Analyzer Data

Figure 20:
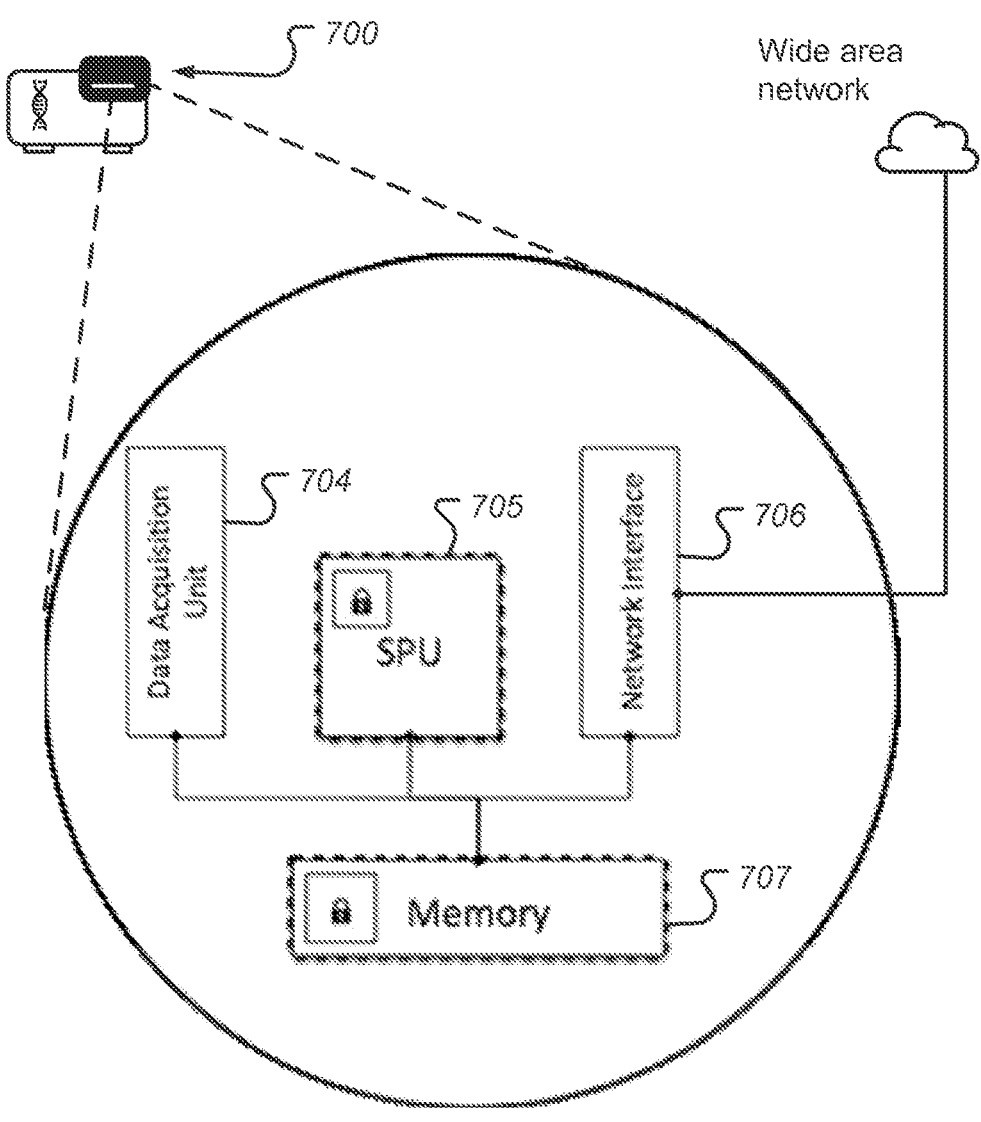
FIG. 20 shows an overview of the components in an illustrative secure analyzer, according to some embodiments.

According to some embodiments the data that is provided to the Gene Cloud comes from a secure environment that protects patient privacy and data integrity from the point of collection. FIG. 20 shows an overview of the components in a secure analyzer, according to some embodiments. Sequencer 700 is an instrument used to automate the DNA sequencing process. Given a sample of genetic material, the sequencer 700 produces information that is used to determine, e.g., sequence of nucleotide bases or amino acids present in the sample. The data acquisition unit 704 can include, for example, known techniques in modern automated DNA sequencing instruments to acquire the sequence data. In addition to the base sequences, sequencer 700 may also supply additional observations of the sample, such as epigenetic data, base call quality scores, etc. The genomic data is processed using a secure processing unit 705 and stored on a secure storage unit 707. A network interface 706 is provided for communication with a wide area network.

Figure 21:
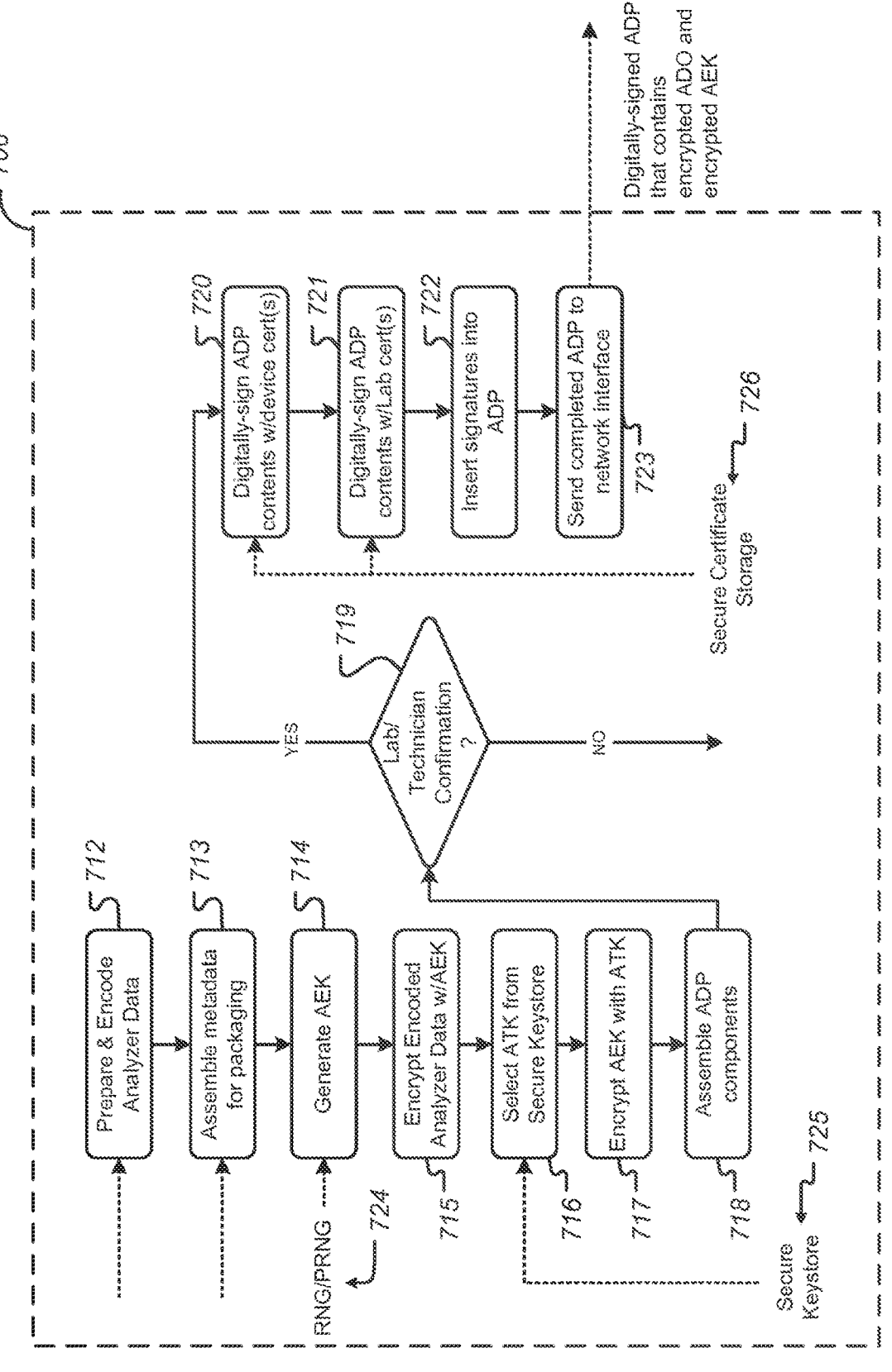
FIG. 21 is a flowchart illustrating a process by which data is captured, protected, and/or provided to the Gene Cloud, according to some embodiments.

FIG. 21 is a flowchart illustrating a process by which this data is captured, protected, and/or provided to the Gene Cloud, according to some embodiments. In some embodiments, the processing actions shown are carried out within the sequencer 700 such as shown in FIG. 20. According to other embodiments, the actions shown are carried out in a system that is in a trusted environment with the sequencing equipment, an example of which is using a dedicated secure processing system located within the same facility as the sequencing equipment. For ease of explanation, in this example, assume that the actions shown in FIG. 21 begin where the work of the genetic sequencing ends and the genomic data is to be protected and uploaded into the Gene Cloud. However, it is also possible, and in some cases desirable, for the data to be encrypted immediately upon generation to minimize the physical and logical "attack surface". According to some embodiments, if sequencing data is to be exposed, e.g. for quality control, it is immediately destroyed if and when it is protected.

Figure 22:
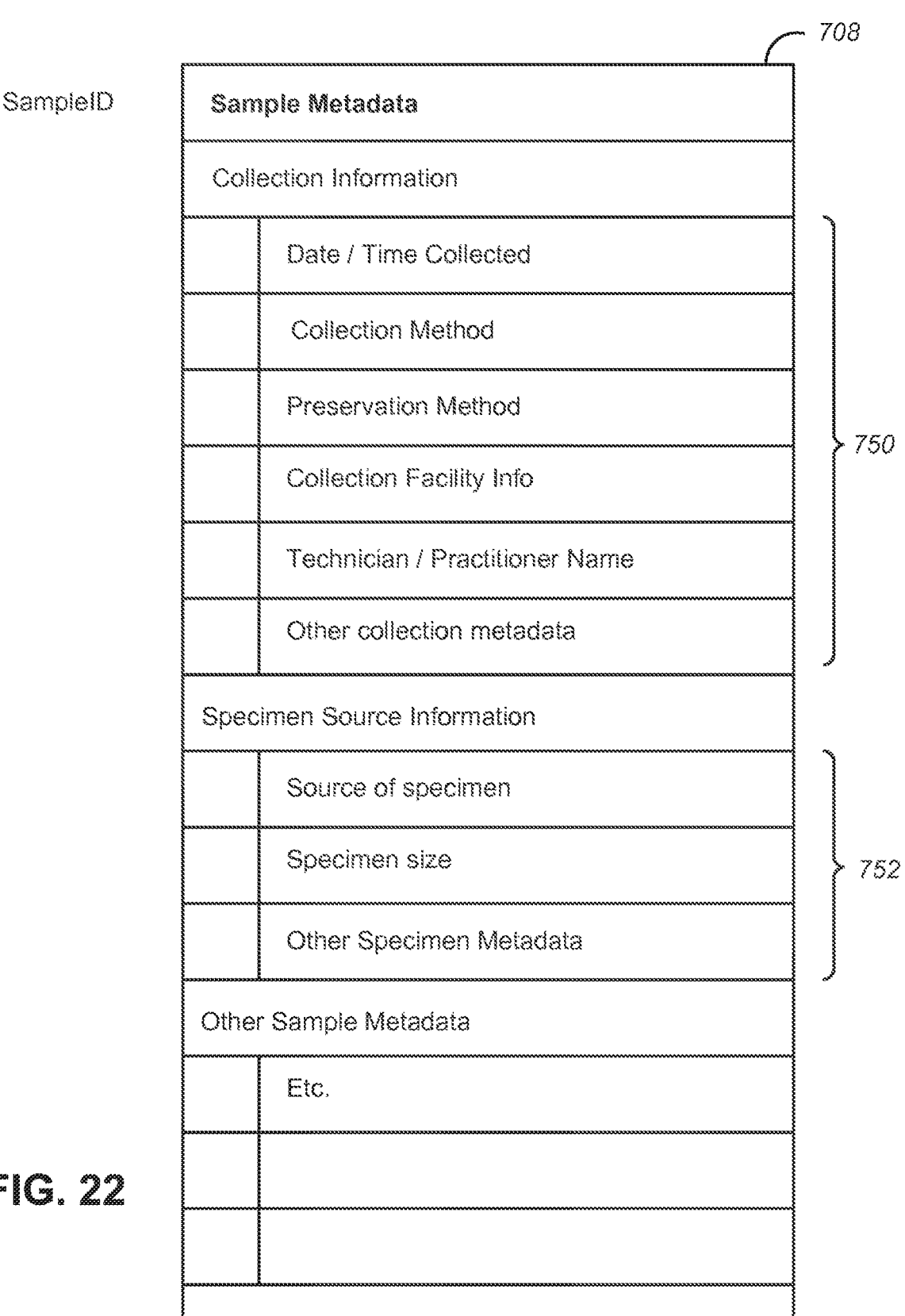
FIG. 22 shows an example of a possible format for an assembled genomic metadata package, according to some embodiments.

At block 712, the gene sequencing information is prepared and formatted for upload. At block 713, the metadata for tagging the sequence data is assembled. For example, the SEQID as described above, timestamps, lab identifying information, and/or the like. FIG. 22 shows an example of possible format for an assembled genomic metadata package, according to some embodiments. A metadata package 708 is shown that includes collection information 750 and specimen source information 752.

Referring again to the example embodiment shown in FIG. 21, at block 714 a random ephemeral encryption key is generated for protecting the data in transit, using a cryptographically secure random or pseudo-random number generator 724. This key is referred to as an Analyzer Encryption Key (AEK). Alternatively, or in addition, this key may be obtained in other ways, e.g. (a) from the Gene Cloud over a secure network connection, (b) from a secure storage module within the device that was provisioned with a set of keys, (c) from a smart card, and/or (d) in any other suitable manner. These techniques may be used to avoid embedding a secure key store in the device, reducing the risk of tampering when the device is not in use.

At block 715, the analyzer data is encrypted with the AEK. At block 716 the public key corresponding to the destination of the data (here called ATK) is determined by consulting a key store 725. This database 725 may, for example, contain keys for multiple ingestion points in various locales, or it may contain a key for a single centralized Gene Cloud ingestion point. In one embodiment, the contents of this key store are not secret, but are protected against tampering to prevent inadvertent upload to an untrusted destination. These public keys may also be obtained from a registry maintained by the Gene Cloud. In an alternative embodiment, a Gene Cloud service may determine the nearest ingestion point to a given sequencing device by geolocation and deliver the public key of the corresponding ingestion point.

At block 717, the ephemeral key AEK is encrypted with the destination public key ATK. At block 718, the components are assembled into a package for shipping to the ingestion point. At block 719, a confirmation is made with the lab technician that the analyzer data is to be uploaded. According to some embodiments, block 719 is not carried out; rather the system is configured such that all data collected is automatically uploaded. However, in some cases it is desirable for a laboratory technician to confirm that the processing of the sample was conducted according to established procedures and to authenticate himself or herself so that the identity of the technician is securely associated with the packaged data. The technician/operator may also associate external information (e.g., annotations regarding the sequencing process or other metadata) with the sample. Preferably, the process by which the technician associates information with the sequence does not require disclosure of any personal information about the sample donor.

In some embodiments, the implementation of the technician authentication may involve signing the data (as at blocks 720 and 721) with a private key that is accessible only to the particular operator upon entry of a PIN code, a password, and/or the like. The storage of such keys may rely on mechanisms similar to those described elsewhere herein, or they may be stored, e.g. in smart cards that are used in authentication to the data collection system. According to some embodiments, the signed data in 719, 720, and 721 will include both the metadata and the encoded, but unencrypted sequence data. This will allow for proper verification of the data prior to downstream processing, and will also permit the sequence data to be transcrypted without compromising the signature.

In the example embodiment shown in FIG. 21, at block 720 the data is signed with the private key of the analyzer/sequencer device, as certified under the Device Manufacturer Trust Root described above. This signature will be verified to indicate that the data was generated by a trusted device. The private key used to apply this signature is stored in a secure storage area 726 that is protected against tampering and exposure of the keys. At block 721, the data is signed, e.g., with a private lab key certified on the Laboratory Trust Root described above. This signature will be checked to verify that the data were collected in a lab with the appropriate certifications. At block 722 the data and signatures are packaged for transport. At block 723 the Analyzer Data Package (ADP) is uploaded to the ingestion point. The workflow shown in FIG. 21 provides an example of how genetic information is protected at the point of origin, according to some embodiments. It will be appreciated that FIG. 21 is provided for purposes of illustration, and that in other embodiments, other work flows could be used, other encryption, key management, and/or other security schemes may be used, and/or the like, all in accordance with the principles of the inventive body of work.

FIG. 23 shows an example of an analyzer data package (ADP) format 760, according to some embodiments.

According to some embodiments, once the sequence data has been protected, e.g., in accordance with a workflow such as that described above with respect to FIG. 21, the data is ingested by the Gene Cloud. The ingestion point may be one of many operating within an ecosystem of interconnected components, or it may be a centralized ingestion point.

FIG. 24 illustrates the relationship between keys in the environment of analyzer 700 and keys at the point of ingestion of the Gene Cloud system 140, according to some example embodiments. It will be appreciated that FIG. 24 is an example, and that in other embodiments, other relationships may be employed, and/or different types of cryptographic and/or other security techniques may be used.

Figure 25:
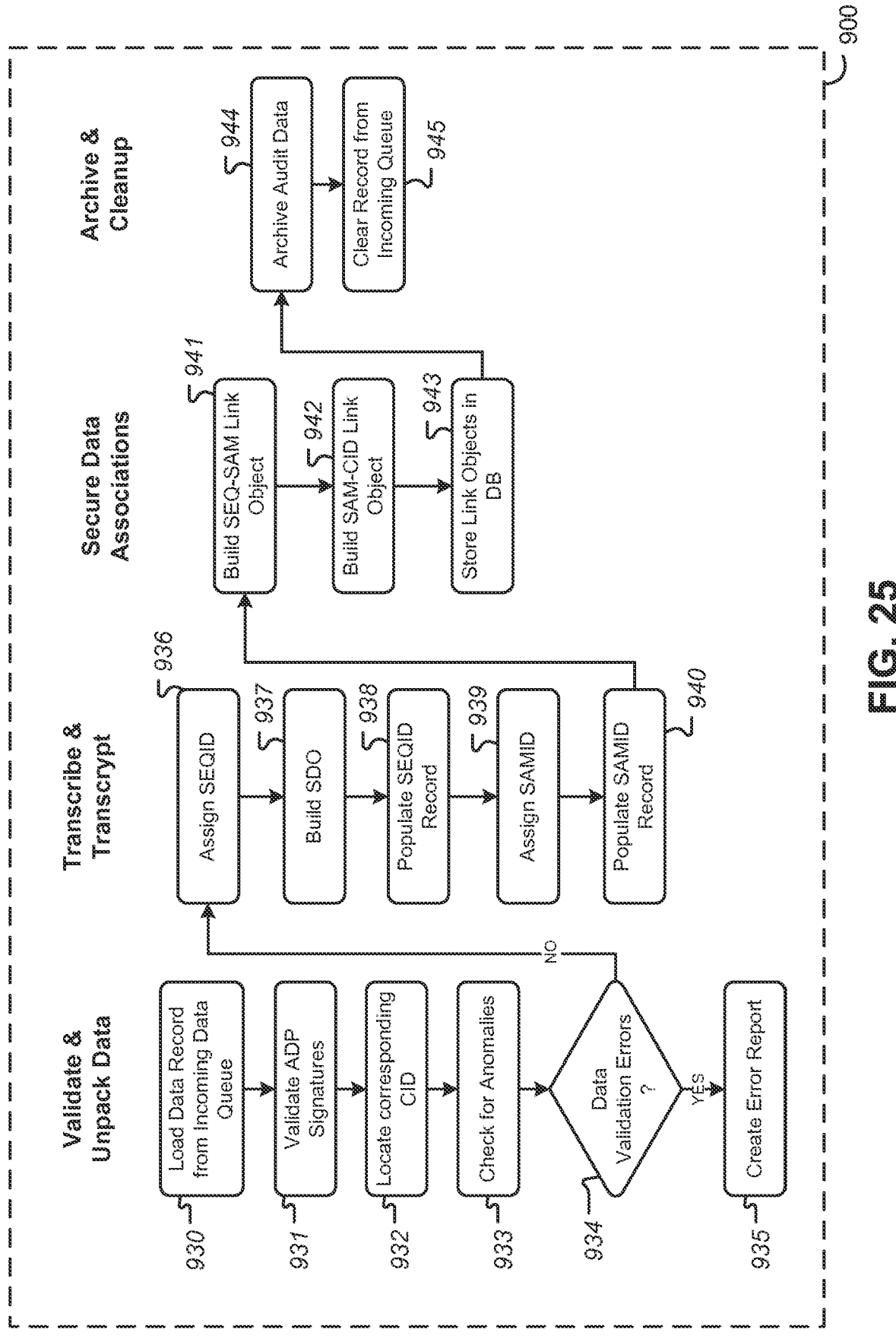
FIG. 25 is a flowchart showing illustrative actions in the ingestion of data produced by an analyzer, according to some embodiments.

FIG. 25 is a flowchart showing actions performed in the ingestion of data produced by the analyzer, according to some embodiments. In the example shown in FIG. 25, the process 900 is carried out through four stages: (1) validation and unpacking—e.g., verifying that the data came from a trusted device, lab, etc. and unpacking and validating the data package; (2) transcryption and transcription—removing ephemeral packaging and formatting data in a Gene Cloud internal format; (3) creating secure associations—recording the associations between the sample data and a consumer; and (4) archiving and cleanup—storing the data for long-term archiving, and removing temporary artifacts.

At block 930, the data is loaded from the queue into which it was received. At block 931 a verification is made that the signatures on the Analyzer Data Package are valid. For example, this could include verifying signatures that were applied at blocks 720 and 721 in the analyzer workflow shown in FIG. 21. At block 932, the temporary SEQID is used to look up the consumer ID (CID or CUID) to whom that ephemeral SEQID was issued.

At block 933, a check is made for anomalies in the data formatting, or if the ADP containing the SEQID was received from an unexpected source that is not typically associated with the entity to which the SEQID was provided for processing, etc. At block 934 a decision is made whether to proceed or not based on the foregoing actions. At block 935, an error report is created if required. At block 936 a new SEQID is assigned to replace the temporary one. At block 937 the Sequence Data Object (SDO) is built. In one embodiment, the SDO is a superset of the information contained in the ADO, which may include, for example, annotations of the data that were automatically generated upon ingestion or other metadata. At block 938 the SEQID record, such as shown in FIG. 14, is populated. At block 939, a sample ID (SAM ID) is assigned. At block 940 the SAM ID object, such as shown in FIG. 14, is populated. At block 941, a SEQ-SAM link object is built, connecting sequence and sample data. At block 942, a SAM-CID link object is built, connecting SEQ and SAM to CID/CUID. At block 943 the link objects are stored in a secure database. At block 944 data is archived for auditing purposes (e.g. ephemeral keys, IDs, etc.) as these may be required for forensic purposes later. In some embodiments, these are preferably protected and isolated from other data used in the standard operation of the Gene Cloud. In cleanup block 945, the ingestion is marked as done and the incoming object is removed from the queue.

Once sequence data is uploaded into the Gene Cloud, and associated with a user/patient identity (block 942), other information associated with that identity, e.g. permissions, may be used to govern access to and use of the data by VDTs. According to some embodiments, the Gene Cloud may store or index health records and other personal information under the same user identity. Thus it is possible for VDTs to operate on the sequence data for a particular person (or a group of people with specific attributes), but the linkage between the user identity and the sequence is only stored indirectly. In one embodiment, the default Gene Cloud policy prohibits VDTs from seeing the link between phenotypical (health record, etc.) data and genotypical data.
Trusted Data Analysis Platform While much of the foregoing description has dealt with examples in the field of genetics, the data protection, processing and analysis systems and methods described herein are suitable for application more generally in other contexts as well, including, without limitation, personalized medicine, energy management, targeted advertising, and smart automotive systems, to name just a few examples.

For example, data mining algorithms must necessarily have access to the data to be analyzed in order to perform their analyses. Too often, however, providing an algorithm with access to a data set also involves providing certain people—such as informaticians, data scientists, researchers, IT personnel—with access to the data as well. To the people whose data are included in such a data set, disclosure may constitute an unacceptable risk. For example, compromised healthcare data may lead to irreparable harm to both the patient whose information is inadvertently disclosed and the institution that disclosed it. In many cases, data breaches are not intentional. Instead, they arise due to careless policies such as allowing personal information to be stored on laptop computers or flash memory drives that can be stolen or misplaced.

In other cases, providing full access to raw data creates liability for the analyst. For example, if a physician wishes to perform a genetic test to scan for Alzheimer's Disease risk factors, and she is given an entire genome sequence as input, her legal and ethical obligations to inform and treat the patient based on other information contained in the genome sequence are unclear. If the patient's genome contained, for example, evidence of a severely elevated risk of an unrelated disorder, the physician may be legally or ethically required to inform and treat the patient, even if the information regarding the second disorder is merely latent in the information she holds.

Finally, it may be impractical or infeasible to move raw data sets due to the size of the data or legal restrictions. For example, whole genome sequencing of human genomes can produce approximately 300 GB of information per person, information that may expand even further when augmented by sequence data from the human microbiome. Centralizing such data so that it may be analyzed by a data mining algorithm may be difficult or impossible. In addition, national and regional laws may explicitly prohibit such data from leaving its country of origin.

The preceding examples point out a deficiency in the way we currently analyze large data sets. Embodiments of the systems and methods described herein can be used to provide a trusted data analysis platform (such as illustrated in the previous discussion of the gene cloud system) that addresses these deficiencies by allowing trusted data analysis programs to operate on trusted data in a secure environment in a manner that respects the policies of data stakeholders and prevents the leakage of personal information.

Allowing the Program, not the Analyst, to Access Raw Data

One problem with the way data analysis works in current practice has to do with the fact that the analysts that run the analysis programs often have access to the raw data that forms the input to the algorithm. Even in cases where these analysts are themselves trusted actors, the data are still at risk of comprise. In some embodiments of the systems and methods described herein, this problem is addressed by allowing the analysis program to operate on the data and generate an answer without requiring that an analyst ever have access to or control of the raw data. This configuration removes the need for the analyst to store and organize the data, and has demonstrable privacy-preserving properties as well. For example, suppose that a genetic counselor wants to know the probability that the offspring of two patients will be born with a specific genetic disorder such as Tay-Sachs Disease. A carrier screening program C takes the genome of one subject as input, determines whether the subject is a carrier for the disease. Program C is run on both subjects, and the results are combined to determine the odds of the offspring having the disease. If both parents are carriers, their offspring have a 25% chance of having the disease and a 50% chance of being a carrier. If it is not true that they are both carriers, their offspring have no chance of having the disease. In this case, running the program C on both patients reveals to the counselor, with 100% certainty, the carrier status of both patients.

On the other hand, if the carrier screening program C could run on the data in a manner that was not visible to the counselor, and those results could be combined by an additional program R that returns true if both patients are carriers and false otherwise, then the individual carrier status is revealed only in the case that both patients are carriers, which is exceedingly rare—the probability is approximately 0.14% even in the most at-risk population for Tay-Sachs Disease. In other words, the probability that extremely private information is revealed is significantly less than 1%, versus a certainty of 100% using existing methods. As this example illustrates, allowing a data analysis program to access data in lieu of a human operator provides additional privacy properties that are not otherwise achievable.

Thus, in preferred embodiments, an execution environment is provided that can run data analysis programs in a way that does not reveal an unacceptable amount of intermediate information to the creator of the data analysis program.

Trusting the Analysis Programs

When, as suggested above, data analysis is performed out of the sight and control of the person or people that will rely upon the answer, it becomes important to ensure that the correct program was actually executed on the data. Suppose for example that a malicious actor claims to have executed a given analysis program, but in fact surreptitiously substituted another program in its place and executed that program instead. Or suppose that an operator inadvertently uploaded the incorrect program to the execution environment due to an innocent clerical error. The relying party may draw incorrect conclusions from the results produced.

For this reason, in preferred embodiments, a mechanism that allows the program to be trusted is used. With a mechanism that allows various parties to assert the trustworthiness of the program (possible implementations are described elsewhere herein), the system can, among other things, do some or all of the following:

Reliably prove that a given program was run against a given set of inputs;

Prove that the program was authored by a specific individual or organization with a access to specific authentication credentials; and/or Provide assurance that a competent third party examined or tested the program and certified attributes such as its effectiveness, accuracy, functionality, or source.

The VDTs described elsewhere herein are an example of such a trusted analysis program.

Trusting the Input Data

Similarly, if a trusted execution environment is to be used to run a trusted analysis program against a certain set of data without the direct intervention of the relying parties, it is equally important to be able to trust that the data being operated upon have not been modified, that the data originated from a known source, that the data were generated before a specific date, etc. With trusted data, a system can, for example:

Protect the privacy of the data;

Prove that the data were collected at a certain time;

Prove that the data have not been modified since they were collected;

Assert that a specific trusted analysis program operated upon the data at a given time; and/or Maintain trusted metadata about the source of the information, such as the systems and people involved in its collection, the time of collection, environmental circumstances attending the data collection, etc.

In some embodiments, a trusted analysis program may express requirements on the types of input data it consumes, including trust requirements. For example, a trusted analysis program may decide to operate on data collected only by a certain type of equipment, or in a certain format, or approved by a particular third-party authority. Likewise, trusted data may carry policies that allow it to be accessed only by trusted analysis programs with specific characteristics.

Governing Access Based on Policy

In cases where a trusted data analysis platform stores trusted data on behalf of the stakeholders of the data, the stakeholders typically cannot manage access to the data through physical custody. In order to provide stakeholders with control over the use of their data, a system may implement a policy management system that governs access to trusted data by a trusted analysis program.

In one embodiment, a trusted data policy is a machine-readable object that encodes rules that govern access to a specific trusted data object. Trusted data policies are created by stakeholders in the trusted data and enforced by the trusted data analysis platform. As was illustrated in the case of a gene cloud system, the policy management system may govern many different aspects of trusted data access. For example, a trusted data policy may:

Allow only trusted analysis programs created by a certain individual or organization to operate upon the trusted data;

Allow access only to trusted analysis programs created by principals in a whitelist created by the stakeholder specifying the policy;

Prevent all access to the trusted data unless each specific access is explicitly approved by the stakeholder specifying the policy;

Decide to grant or prohibit access based on the identity of the principal that requested the execution of the trusted analysis program on the trusted data and/or who will receive the result of the execution (e.g., the requesting principal);

Allow access to only certain parts of the trusted data, depending upon the creator of the trusted analysis program or the requesting principal;

Allow access to the trusted data only for specific types of identified uses (e.g., the intent of the requesting principal); and/or Allow or prohibit access based on historical information stored by the trusted data analysis platform, including, e.g., records about how much information from the trusted data has been revealed in the past, and to whom.

Implementing a Trusted Data Analysis Platform

A trust management system is a system in which various actors/principals involved in the operation of the system may verifiably assert properties about other principals, systems, or data objects. In one embodiment, the trust management system comprises a set of related digital certificates (e.g. X.509v3 certificates) that securely associate public encryption keys with well-defined subject names, plus a set of certificate policies that determine how the certificates are to be used. These certificates, along with the private keys corresponding to the certified public keys may be used as part of a digital signature algorithm to assert that the signer's particular policy has been satisfied. The digital signature and the certificate may be used to verify the assertion.

In addition to making verifiable assertions, digital signatures are used to prove knowledge of the state of the signed object. Because a digital signature involves hashing the object being signed, a relying party can verify that the signer of the object was able to compute this hash over the object in question, a fact that can be verified at a later date for forensic or auditing purposes.

As the previously described examples have illustrated, a trust management system can be used in a trusted data analysis platform in many ways, including, without limitation, some or all of the following:

A certification agency with expertise regarding a certain type of data analysis might use its certificate to digitally sign a trusted analysis program (e.g., a VDT), in effect asserting that they have investigated the program and found it to be consistent with their policies. As a concrete example, the FDA may sign a trusted analysis program that is designed to help with dosing of a particular pharmaceutical. The signature asserts that the trusted analysis program was approved by the FDA.

The creator of a trusted analysis program may sign his own program using his own certified key, thus asserting that he is the actual author of the program.

A device certification agency may certify that a particular model of device performs within an acceptable parameter (as defined by its certification policy) and issue a certificate to the device, signed by its own certificate.

A trusted data analysis platform (e.g., a gene cloud system) may add its own signature to trusted analysis programs as they are uploaded as part of its own auditing processes.

When a trusted analysis program has been executed on a trusted data item, the trusted execution environment may create an audit record that brings together hashes of, e.g., (a) the trusted data objects that were input to the program, (b) any state or environmental inputs to the program, (c) the program itself, (d) the response produced by the program, and/or (e) a timestamp. This trusted audit record may be signed by the trusted execution environment and stored, so that it maintains a verifiable record of the computations performed.

In some embodiments, a trust management system may be a singly-rooted system in which a self-signed root certificate is used to sign all end-entity certificates or intermediate certificates (which are themselves used to sign other intermediate or end-entity certificates), all under the governance of a single set of certificate policies. Alternatively, a trust management system may be distributed, such that a root certificate is used to issue intermediate certificates to distributed trust authorities that control their own certificate policies, consistent with the root policy. A trust management system may also be a fully decentralized system in which various root authorities define their own certificate issuance policies and are relied upon or not according to the trustworthiness or suitability of their certification policies in any given instance. This latter, decentralized model is similar to the way in which certificates are used within the World Wide Web.

Trusted Analysis Program

A trusted analysis program (a specific example of which is a VDT of the type described previously herein) may be implemented in many ways, including as a compiled executable or interpreted program for a given machine (including virtual machines), or as a declarative document that describes the analysis is to be performed. A trusted analysis program may also rely on calls to services or functions provided to it by the trusted data analysis platform.

In some embodiments, a trusted analysis program may carry with it metadata that indicate information about the program, including, for example, information regarding its author, intended function, date of creation, and/or the like. It may also carry one or more digital signatures that assert various properties about the program—for example, that it was tested under a given compliance regime—along with the public information necessary to verify the assertions (e.g., the certificate chains).

In some embodiments, a trusted analysis program may be accompanied by requirements on the types of trusted data that may be accepted as input. These requirements may include the data format as well as requirements on the provenance of the data, e.g., the model of equipment used to generate the data, the device certificate, the certification authority that issued it, and/or the like. In addition, the trusted analysis program may, as part of its operation, contain a function or subroutine that actively evaluates trusted data objects for possible input into its analysis. For example, a trusted analysis program operating in a trusted data analysis platform for healthcare may specify that it would like to include in its analysis data from all persons of Japanese ancestry that are over 85 years of age and have no family history of cancer.

In some embodiments, a trusted analysis program may comprise a workflow specification indicating how various other trusted analysis programs are to function in concert to produce a given result. These trusted analysis programs may in fact be created by different authors.

Trusted Data

In one embodiment, trusted data objects are sets of information with accompanying security assertions. For example, in an electricity metering application, a trusted data package may comprise a set of measurements from a home energy meter and a digital signature created by the device that covers a timestamp and the measurements.

In other applications, a trusted data object may be signed by multiple entities. For example, in a genetic sequencing application, a gene sequence produced by a sequencing machine may be signed with two certificates: one associated with the machine itself, and a second associated with the human operator who ran the machine, authenticating himself, and asserting that the sequencing machine was operating normally at the time of sequencing.

In some embodiments, trusted data may be accompanied by metadata that describe the data, the circumstances of its collection, and/or so forth. These metadata may also be covered by the various digital signatures so that the metadata are securely and verifiably associated with the data themselves.

Data need not be signed immediately upon collection. In some embodiments, a measurement device holds the public key of a trusted ingestion point which will attach the signatures itself. The measurement device that produces the original data can, for example, send data securely to the ingestion point as follows: (a) it generates an ephemeral symmetric key (or obtains such a key over a secure connection or from trusted storage) to encrypt the data, (b) it encrypts this ephemeral key with the public key of the trusted ingestion point, (c) it encrypts the data and any associated metadata with the ephemeral key, and (d) sends the encrypted results from steps (b) and (c) to the trusted ingestion point. The trusted ingestion point decrypts the data, potentially stores the ephemeral key for auditing purposes, then re-encrypts and signs the data to produce a true trusted data object.

In some embodiments, trusted data objects may be identified by temporary identifiers when they are first generated. This may be needed in some cases to protect privacy, such as when the trusted data consist of health measurements, those measurements are being made by a laboratory, and the laboratory should not know the identity of the patient or any of the long-term identifying information that will be used for the trusted data. In such cases, a random, temporary identifier may be created at the point of origin (or obtained from a trusted service) and the trusted ingestion point can archive the identifier for auditing purposes and assign a new, long-term identifier.

Trusted Data Policy

Trusted data policies are used by a trusted data analysis platform to govern the use of trusted data. Trusted data policies may be created and associated with the trusted data by stakeholders in the trusted data. A particular embodiment of a trusted data analysis platform will typically come with its own conventions regarding stakeholder access to and visibility of trusted data.

For example, in a smart automotive application, the owner of a car may have an account in the trusted data analysis platform. The trusted data generated by her car (containing, for example, location data) may be tagged with metadata that allow the secure ingestion point to associate the trusted data objects with her account. By visiting a website front end to the trusted data analysis platform, the driver may opt to share her most accurate location data with her spouse and her daughter, but only her total driving distance with her insurance company. This particular embodiment of a trusted data analysis platform could, for example, use a trusted data policy language that enables such policies to be specified.

As illustrated in the example above, trusted data policies can be application-specific and do not necessarily apply to all possible embodiments. As such, trusted data policies may be encoded in many different ways.

In some embodiments, trusted data policies can be chosen from a menu of policies with pre-defined or standardized semantics. In a healthcare application, for example, a set of such policies may include terms such as HDL cholesterol, peak flow, heart rate, blood oxygen, and so forth, and may allow access to those data based on exact measurements, average measurements over a given period of time, minima and maxima, and/or the like. In cases such as this, it is natural that the policies be expressed in a declarative syntax, such as in an XML-based language. However, it will be appreciated that any suitable policy expression and enforcement mechanism or mechanisms could be used.

In other cases, the trusted data policies could be executable on a given machine (including, e.g., one or more virtual machines) as in the systems described in the '551 patent and '693 patent. Policy management systems that allow executable policy are generally more expandable under new circumstances and do not necessarily require agreement on a pre-determined set of policy semantics. In this example and the previous one, the data policies can, for example, be expressed as pre-conditions conditions that must evaluate to true before allowing access to the trusted data.

As described in commonly assigned U.S. patent application Ser. No. 13/444,624, entitled "Information Processing Systems and Methods" ("the '624 application"), the content of which is hereby incorporated by reference in its entirety, a trusted data policy may also be used to perform a computation on the trusted data before yielding it to the trusted analysis program. This type of policy can allow, for example, a user to specify that a randomization function be applied to the trusted data to obscure the exact measurement when the analysis has been requested by a certain class of principal. As in the automotive example above, a user may be happy to share his raw location data with some requesters, but may require that all data not collected between the hours of 9 am and 5 pm be filtered out when requested by other principals. This may be accomplished by specifying a computation as part of the trusted data policy for this trusted data object.

Stakeholders in the trusted data may also specify default policies that govern trusted data automatically, unless explicitly changed by the stakeholder. A particular embodiment of a trusted data analysis platform may also specify its own default policies, including, for example, failsafe policies that allow no access whatsoever unless approved by the appropriate set of stakeholders.

Depending on the policy languages and schemas implemented in a particular trusted data analysis platform, trusted data policies may apply to subsets of a trusted data object. For example, if the trusted data consists of a human genome, one trusted data policy may govern access to a particular gene, with other genes governed by separate policies.

Trusted Execution Request

In a trusted execution request, an authenticated principal asks to run a given trusted analysis program on one or more trusted data objects. In one embodiment, a trusted execution request may comprise some or all of the following:

A requesting principal—e.g., the identity of the person or entity that is requesting that the analysis be performed. This may, for example, be the user identifier of the person that asked for the analysis to be performed.

An intent—e.g., specifying why the requesting principal is making the analysis request in a way that is able to be evaluated within the policy management system implemented by the particular embodiment of the trusted data analysis platform. For example, in an embodiment that stores and operates on genetic data, the intent may be specified as "clinical diagnostics". The intent may also include information about a specific subset of the trusted data to be accessed, e.g., the BRCA2 gene.

Optionally, one or both of the following: (a) a list of one or more trusted data objects to be analyzed, and/or (b) a predicate that trusted data objects must satisfy to be candidates for the analysis. For example, the predicate might specify that the analysis should include driving data from drivers who are over 55 years of age, or healthcare data from persons of Japanese ancestry over the age of 85 that have no history of cancer. Note that in some embodiments, a trusted analysis program itself may contain a predicate that evaluates trusted data objects for potential input to the analysis, thereby obviating the need for a separate predicate.

A specification of the trusted analysis program to be run.

Trusted Execution Environment

In some embodiments, a trusted execution environment brings together some or all of the following things:

A trusted execution request;

At least one trusted data object, as specified in the trusted execution request;

A trusted analysis program, as specified in the trusted execution request; and/or At least one trusted data policy associated with at least one of the trusted data objects.

In one embodiment, the trusted execution environment performs the following steps to execute a trusted analysis program:

For each trusted data object either explicitly requested in the trusted execution request or matching an input predicate in the trusted execution request:

Verify the integrity of the trusted data (e.g., this operation may simply be a look up of information cached when the trusted data were ingested);

Verify that the trusted data satisfy any applicable requirements concerning the trusted data that are specified as part of the trusted analysis program;

Verify that the trusted data policies associated with the trusted data allow access, given the intent and requesting principal, the author, certification status, and/or other attributes of the trusted analysis program, or other relevant policy variables.

For those trusted data objects that are validated, run the trusted analysis program on the trusted data and produce a result.

During execution of the trusted analysis program, access to various other trusted data may be requested, or to different parts of trusted data already validated before execution. In such cases, verify that the trusted data policies allow the access before releasing the data to the trusted analysis program;

The result may or may not be released, or it may be modified, e.g., based on the history of information revealed about specific trusted data involved in the execution of the trusted analysis program. As described in the '624 application, the result may consist of a protected resource with associated conditions and computations that govern access to the result.

Audit the execution by creating a secure audit record. In one embodiment, this audit record brings together some or all of the cryptographic hashes (or the results of running some other one-way function) of the trusted data that participated, the trusted analysis program, other environmental or state data that was used by the trusted analysis program, a timestamp, and/or the result produced by the trusted analysis program. In one embodiment, the trusted data analysis platform maintains the objects that were hashed such that the system is able to verify that the trusted analysis program was executed forensically.

Some additional, more detailed examples of implementations of systems and methods embodying various aspects of the inventive body of work are provided below.

Example: Anonymous Energy Monitoring

A local utility such as a power company can use a trusted data analysis platform to anonymously monitor energy use to help with load prediction and to anonymously reach out to customers with excessive energy consumption with suggestions as to how their usage may be reduced. Consumers with accounts in the system may sign up to receive discounts for new appliances that focus on their most inefficient uses, again, without revealing their identities to appliance manufacturers or distributors, or to the utility company.

The utility company creates an instance of a trusted data analysis platform in conjunction with their rollout of smart metering systems to consumers. The smart meters are associated with credentials that allow them to package and upload trusted data (e.g., information about electricity usage) to a trusted ingestion point that is part of the energy monitoring platform.

Understandably, some customers are nervous about information concerning their electricity usage being available to malicious actors, who might, for example, mine their data for information regarding when the customer is most likely to be at home. As a result, some customers are very sensitive to how their information is collected and used by the utility.

The smart meter in the customer's home creates trusted data objects by encrypting and signing the metering data, then providing the trusted data to a trusted ingestion point, which unpacks it, re-keys it, re-identifies it, and makes it available for use within the trusted data analysis platform.

The utility company responds to their customers' concerns by designing the trusted data analysis platform in a way that allows customers to completely restrict access to their data, so that the utility receives only the information it requires to bill the customer (e.g. the total number of kilowatt hours used).

The utility also wants the metering data to be protected as trusted data, since a consumer that could manipulate the data could illegally manipulate it to take advantage of the utility.

If the customer is willing to have their data more carefully analyzed, they can opt in to programs that, for example, analyze their specific load demands, estimate the kinds of appliances being used, and suggest a set of energy-saving tips that can save the customer money and reduce the overall electricity demand on the utility. For example, the utility might construct a trusted analysis program that looks for discernible patterns such as current demands caused by air conditioning or heavy appliances like refrigerators.

The trusted analysis programs may place requirements on the trusted data that they take as input—e.g., the trusted data objects may be required to be digitally signed using a certificate that the utility issued for one of its smart meters. Before the trusted analysis programs run on a given customer's metering data, the trusted data analysis platform consults the customer's trusted data policy, which either allows or disallows the access.

The trusted analysis program takes the form of a digitally-signed computer program that analyzes the customer's metering data. Depending on the energy use pattern, the trusted analysis program may automatically send a notification to the customer indicating ways in which they might reduce their electricity bill. This notification is sent anonymously, without the usage patterns being revealed to any system operators.

If the utility so desires, it may open its trusted data analysis platform to allow third parties to anonymously mine its customers' data. For example, an appliance company may wish to identify customers who are in need of a new refrigerator because their old refrigerator is highly energy-inefficient.

The appliance company creates a trusted analysis program that scans the smart metering data for tell-tale patterns of an old, inefficient refrigerator. They sign the trusted analysis program using a certified key issued by the utility company for use in its platform. They may also submit their program for third-party certification, such as by the Better Business Bureau.

The utility, which is profiting by allowing the appliance manufacturer to analyze its customer data, places an announcement of the new program in customers' monthly electricity bills. Customers that log into the utility's service and opt in, now have their data routed to the appliance company's trusted analysis program. Customers are incentivized to opt in because they stand to gain a 10% discount on the purchase of a new refrigerator. Any customer that is flagged as being eligible for upgrade is anonymously mailed a manufacturer's discount coupon.

Example: Trusted Health Data

An increasing amount of healthcare data is being generated by consumers through various technologies. For example, a smartphone with a GPS unit and accelerometer can be used to record raw telemetry data that is useful for monitoring an exercise session. Wireless pedometers and heartrate monitors, wi-fi enabled weight scales, and other emerging technologies are being used to help people manage and improve their health. At present, the data collected through these types of technologies are not widely used in clinical settings, although they may be very useful in the hands of the right medical analyst.

There are several reasons that this increasing amount of information is not being fully utilized: (a) the data are typically collected from unreliable sources that may not be properly calibrated; doctors are hesitant to rely on information of unknown provenance; (b) consumers do not fully trust the services that receive and handle these data to keep their information private and secure; and (c) the raw, undigested information is often overwhelming; physicians and other caregivers would like to be able to specify the information that they receive and have the system deliver the data in a meaningful way, rather than as a massive bundle of raw data.

A trusted data analysis platform created to handle healthcare data from biosensors allows doctors to specify exactly which information they receive and how that information is derived from the raw data. It allows patients to carefully control how their information is released, to whom, and with what level of detail. It allows information sharing without requiring that the raw data be distributed.

Detailed Example

Diana is acting as a caregiver for her elderly mother, who is living alone. Her mother Elizabeth has a history of low blood sodium, which has, in the past, led to epileptic-like seizures and numerous falls that resulted in hospitalization. This condition is usually preceded by several days of lethargic behavior, and would be easy to detect for someone living with Elizabeth but rather difficult to detect remotely. Diana has been thinking about asking her mother to sell her house and move in with Diana and her family, but Elizabeth is absolutely opposed to this plan.

Diana reads about a service that has constructed a trusted data analysis platform to help caregivers care for their elderly parents, while allowing the parents to live autonomously as long as possible. The trusted data analysis platform has partnered with various sensor manufacturers to ensure that they are capable of producing trusted data. Specifically: (a) The service has created a trust management system that issues device certificates that can be used to assert that a particular set of sensor measurements were generated by a specific device, along with environmental information that helps to determine that the device was functioning within normal parameters. The service provider has partnered with a few manufacturers of relatively capable devices (e.g., a wi-fi-enabled weight scale, home motion sensors) to integrate the data management and protection technologies into the devices. (b) For other types of devices that may be less capable, such as an activity monitor that clips onto a belt and has a very strict energy budget, the system has deployed a trusted ingestion point that can receive protected data from the sensor without requiring the sensor to have its own encryption keys.

Diana creates accounts for herself and her mother with the service provider, and registers the fact, with Elizabeth's consent, that she is Elizabeth's designated caregiver and can control Elizabeth's account on Elizabeth's behalf.

The service sends Diana several coupons for devices compatible with the service. Diana purchases several of these for her mother's use and registers them with the service through a simple registration interface. The device registration varies depending on the sophistication of the device's user interface, but typically involves entering a device serial number or matching a PIN code. Among the devices that Diana purchases are the following: (a) A wi-fi-enabled scale that automatically uploads weight and body composition data to the service every time Elizabeth weighs herself, which she typically does every morning. (b) A set of wall-mounted motion sensors, one for each room. These communicate through a low-power radio protocol (such as Zigbee or Bluetooth LE) to a base station in Elizabeth's home. (c) Several activity monitors that use the Bluetooth LE protocol: (i) one smart pedometer laced onto Elizabeth's most comfortable pair of walking shoes, (ii) one clip-on activity monitor that Elizabeth can attach to a belt loop, (iii) a pendant to be worn around the neck, and finally (iv) a fitness watch that incorporates activity monitoring. These devices all store their activity information until they are within range of the Bluetooth base station, at which point their data are uploaded.

The service offers several monitoring templates that Diana can use to help keep tabs on her mother. Through an easy-to-use interface, Diana is able to create her own trusted analysis program, which performs the following computations: (a) If none of Elizabeth's registered devices has produced any data within any 3 hour period, Diana should be notified with an email alert, since something may be misconfigured. (b) Elizabeth's activity level is computed based on input from the sensors. Each wall-mounted motion sensor uploads one sample every ten minutes indicating the level of activity it has observed. This number is normalized to a scale from 0 to 99, with 0 indicating no motion whatsoever. Elizabeth typically rises at 7 am, takes a nap from 1 $\mu$m to 2 $\mu$m, and retires at 10:30 pm. Diana's trusted analysis program requires that at least one of the motion detectors register a motion level above 50 during the morning and afternoon waking hours. If this condition is not met, Diana is to receive an email notification. (c) If any of Elizabeth's activity monitors registers free fall, Diana is to receive an immediate SMS message, and if she does not respond within one minute, a series of phone calls at one minute intervals. If Diana cannot be reached within two minutes, the system is to contact an emergency dispatcher. (d) If Elizabeth does not weigh herself for three days in a row, Diana would like to know about it, as it implies that Elizabeth is not observing her customary habits.

Once she has created this program, she registers it with Elizabeth's account and it begins to run. Diana is initially over-cautious in setting the parameters and calling her mother in a panic when she receives an email, but she is very happy with the service overall because it gives her the peace of mind that she knows what is happening in her mother's home even when Diana is not there.

At her next medical checkup, Doctor Howard, Elizabeth's doctor, indicates that he is worried about Elizabeth's recent weight gain, and would like her to track her weight and make sure that she walks at least 10,000 steps every day. Upon learning that Elizabeth has subscribed to the home health monitoring service, Doctor Howard logs in to his own account and sends a "physician-patient" relationship invitation to Elizabeth, which, if accepted, will register the relationship between the two. Elizabeth's policy settings allow data access to any trusted analysis program that is verified to have been signed by anyone that Elizabeth has agreed is acting as her physician. Diana accepts this invitation on her mother's behalf.

Doctor Howard creates a "data prescription" for Elizabeth—a special form of trusted analysis program that encodes the following rules: (a) If Elizabeth's weight increases by more than 5 pounds from the baseline, send an email to Doctor Howard's nurse. (b) If Elizabeth's average step count in any given week falls below 40,000, send an email to the nurse. (c) If no walking or activity data is collected for more than three days in a row, send an email to the nurse. (d) If an emergency event such as a fall is detected, SMS the doctor.

The data prescription described above was created by a third party that specializes in physical therapy regimens. It is a parameterized trusted analysis program that allows a physician or therapist to enter the parameters such as number of steps, contact addresses, and so forth. This program was signed by the third party using a certificate issued to them for this purpose by the health monitoring service. Doctor Howard has worked with this company in the past, and trusts their products. When he uploads the trusted analysis program, he signs both the templatized trusted analysis program and the parameters he has chosen.

Doctor Howard uploads the trusted analysis program and requests that it be associated with Elizabeth's account. Because of Elizabeth's policy settings, the trusted analysis program begins to execute and access Elizabeth's data.

Diana has been very busy at work, but for the last two days, she has received emails that indicate a reduced level of activity. At first, she thought little of it, since a cold has been going around and her mother may have caught it. But upon receiving the third message, she begins to worry that her mother may be getting lethargic, and decides to call. Her mother claims to be fine, and perhaps to have a little cold, but she is sure that she'll be better tomorrow.

The next day, Diana receives another low-activity notification, makes an appointment with Doctor Howard, and drives to her mother's home to take her to the appointment. Sure enough, Elizabeth's blood sodium has dropped. After a couple of days of treatment, in her own home, Elizabeth is back to normal, and an expensive hospitalization has been avoided.

It will be appreciated that the foregoing examples have been chosen to facilitate an understanding of various embodiments of the inventive body of work, and that the specific details in these examples have been chosen for purposes of illustration and not limitation of the general principles which they demonstrate.

Figure 26:
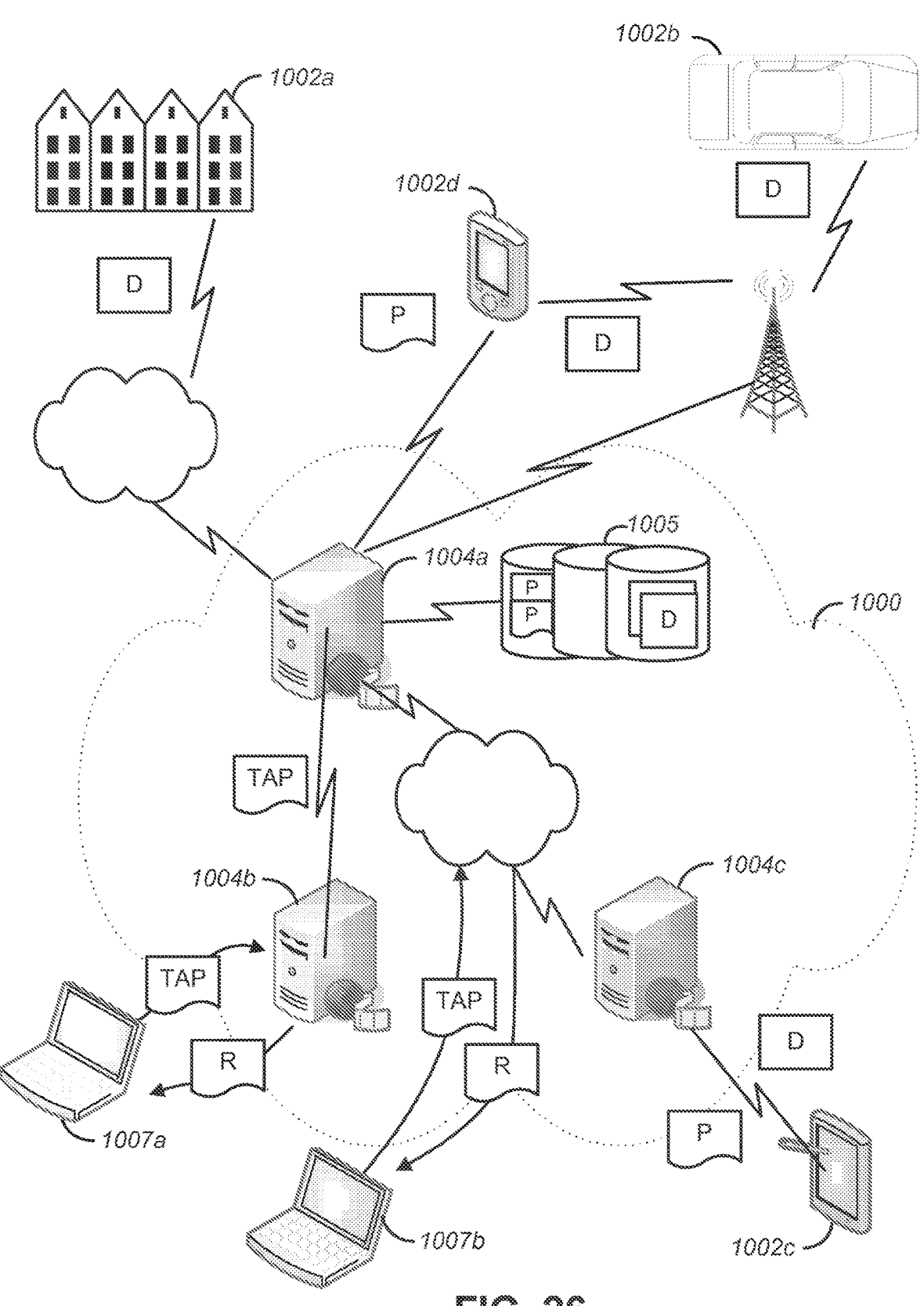
FIG. 26 shows an illustrative system for protecting and governing access to data.

FIG. 26 shows an illustrative system 1000 for protecting and governing access to data in accordance with embodiments of the inventive body of work. System 1000 may, for example, comprise an embodiment of a trusted data analysis platform (e.g., a gene cloud system), the operation of various embodiments of which have been described in detail elsewhere herein. As shown in FIG. 26, entities 1002a-d holding rights in electronic data ("D"), package the data and send it to trusted ingestion points 1004a-c for storage on trusted platform 1000 (rights holders 1002a-d will be referred to collectively as "rights holders 1002," where reference numeral 1002 refers interchangeably to the rights holder or the rights holder's computing system, as will be clear from the context). In some embodiments, the data could be sent to an ingestion point 1004 in unprotected form, and the ingestion point could apply protection to it before storage; in other embodiments, protection is applied, at least in part, by the rights holder's device.

Data could comprise any sort of data, examples of which might include household energy consumption data, automotive location and dynamics data, mobile phone usage and location information, medical information, and/or the like. These data are stored on one or more computer systems 1004, databases 1005, and/or other storage means in the trusted platform 1000, where the data can be used by third parties 1007 for the benefit of rights holders 1002 and third parties 1007. For example, third parties 1007 (which may, for example, comprise medical research labs, utility companies, merchants interested in targeting advertisements, and/or the like) can submit trusted analysis programs ("TAP") to platform 1000, where the programs operate on the protected data in accordance with policies ("P") specified by, e.g., the rights holders 1002 to yield results ("R"). As shown in FIG. 26, policies can be submitted to the trusted platform 1000 in any suitable manner, including, without limitation, directly with the data to which they relate, or separately, at different times and/or using different communication methods. As described elsewhere herein, trusted platform 1000 helps ensure that rights holders' data is protected, while making it available to third parties for useful purposes that are consistent with the rights holders' wishes.

Figure 27:
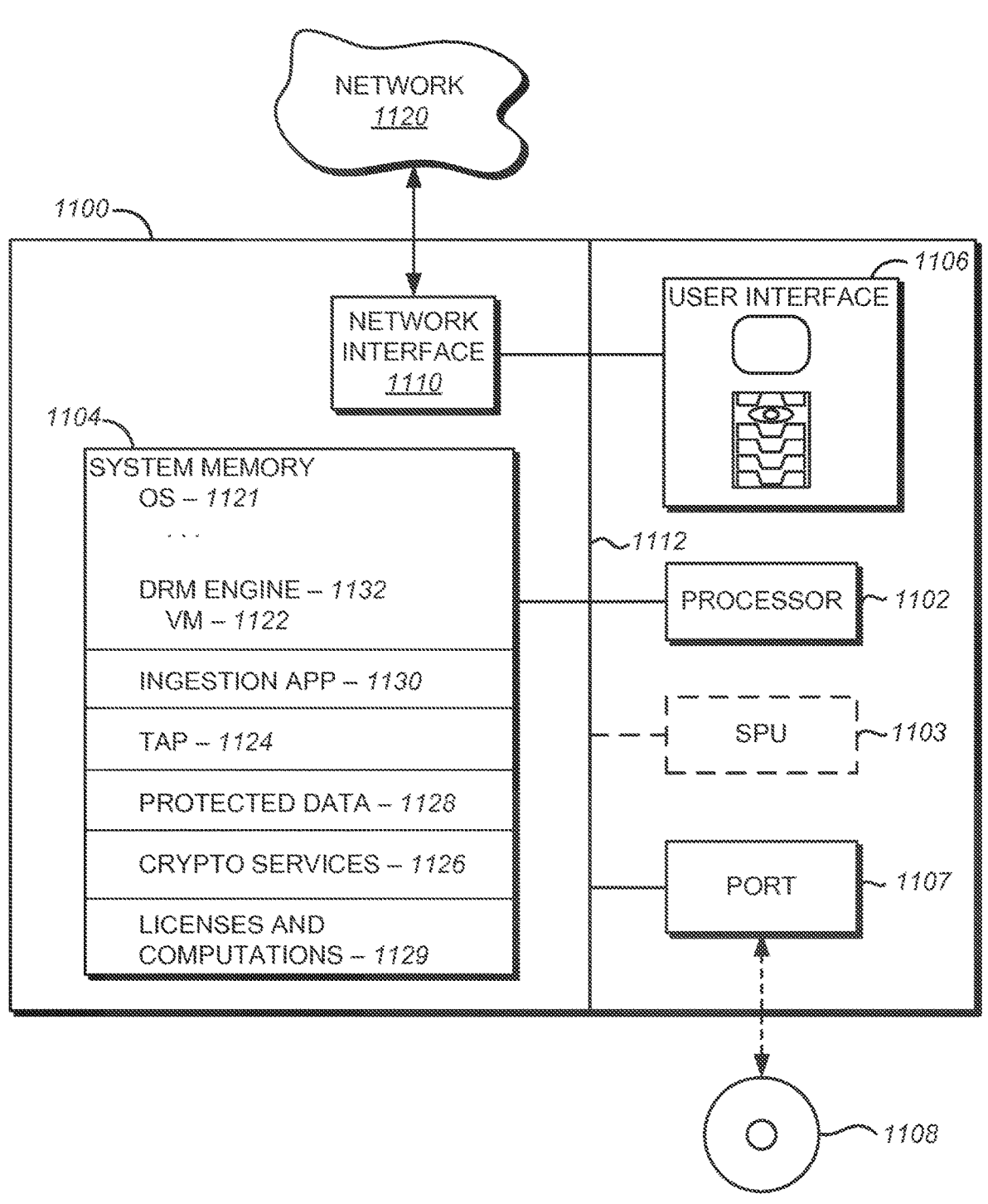
FIG. 27 shows a more detailed example of a system that could be used to practice embodiments of the inventive body of work.

FIG. 27 shows a more detailed example of a system 1100 that could be used to practice embodiments of the inventive body of work. For example, system 1100 might comprise an embodiment of a device in the trusted analysis platform 1000. System 1100 may, for example, comprise a general-purpose computing device such as a personal computer or network server, or the like. System 1100 will typically include a processor 1102, memory 1104, a user interface 1106, a port 1107 for accepting removable memory 1108, a network interface 1110, and one or more buses 1112 for connecting the aforementioned elements. The operation of system 1100 will typically be controlled by processor 1102 operating under the guidance of programs stored in memory 1104. Memory 1104 will generally include both high-speed random-access memory (RAM) and non-volatile memory such as a magnetic disk and/or flash EEPROM. Some portions of memory 1104 may be restricted, such that they cannot be read from or written to by other components of the system 1100. Port 1107 may comprise a disk drive or memory slot for accepting computer-readable media 1108 such as USB drives, CD-ROMs, DVDs, memory cards, SD cards, other magnetic or optical media, and/or the like. Network interface 1110 is typically operable to provide a connection between system 1100 and other computing devices (and/or networks of computing devices) via a network 1120 such as the Internet or an intranet (e.g., a LAN, WAN, VPN, etc.), and may employ one or more communications technologies to physically make such a connection (e.g., wireless, Ethernet, and/or the like). In some embodiments, system 1100 might also include a processing unit 1103 that is protected from tampering by a user of system 1100 or other entities. Such a secure processing unit can help enhance the security of sensitive operations such as key management, signature verification, and other aspects of the systems and methods described elsewhere herein.

As shown in FIG. 27, memory 1104 of computing device 1100 may include data 1128 and a variety of programs or modules for controlling the operation of computing device

1100. For example, memory 1104 will typically include an operating system 1121 for managing the execution of applications, peripherals, and the like. In the example shown in FIG. 27, memory 1104 also includes an application 1130 for ingesting protected data 1128 into the trusted data platform; a DRM engine 1132 or other policy enforcement application for enforcing policy restrictions on the use of data or other aspects of the system; and/or one or more trusted analysis programs 1124 for performing analysis of protected data 1128. As described elsewhere herein, policy enforcement engine 1132 may comprise, interoperate with, and/or control a variety of other modules, such as a virtual machine for executing control programs, a protected database for storing sensitive information, and/or one or more cryptographic modules 1126 for performing cryptographic operations such as encrypting and/or decrypting content, computing hash functions and message authentication codes, evaluating digital signatures, and/or the like. Memory 1104 will also typically include protected content 1128 and associated licenses and computations 1129, as well as cryptographic keys, certificates, and the like (not shown).

One of ordinary skill in the art will appreciate that the systems and methods described herein can be practiced with computing devices similar or identical to that illustrated in FIG. 27, or with virtually any other suitable computing device, including computing devices that do not possess some of the components shown in FIG. 27 and/or computing devices that possess other components that are not shown. Thus it should be appreciated that FIG. 27 is provided for purposes of illustration and not limitation.

Although the foregoing has been described in some detail for purposes of clarity, it will be apparent that certain changes and modifications may be made without departing from the principles thereof. For example, it will be appreciated that while embodiments of the systems and methods described herein can be used in connection with genetic and other medical information, embodiments of the systems and methods disclosed herein can be readily applied to other contexts as well, including, without limitation, contexts involving the handling and processing of data and other information unrelated to the fields of genetics or medicine. Moreover, while a number of complete systems and methods have been presented, it will be appreciated that these systems and methods are novel, as are many of the components, systems, and methods employed therein. It should be noted that there are many alternative ways of implementing both the processes and apparatuses described herein. Accordingly, the present embodiments are to be considered as illustrative and not restrictive, and the inventive body of work is not to be limited to the details given herein, but may be modified within the scope and equivalents of the appended claims.

What is claimed is:

1. A method for performing trusted operations on energy data performed by a trusted data analysis system comprising a processor and a non-transitory computer-readable storage medium storing instructions that, when executed by the processor, cause the trusted data analysis system to perform the method, the method comprising:

receiving at least one energy data object and one or more digital signatures;

authenticating the at least one energy data object using at least one digital signature of the one or more digital signatures;

receiving, from a requesting system, an energy analysis request, the energy analysis request comprising one or more analysis parameters and a reference to the at least one energy data object;

selecting one or more energy analysis programs from a plurality of virtual energy analysis programs based, at least in part, on the one or more analysis parameters included in the energy analysis request;

executing one or more analysis algorithms associated with the one or more selected energy analysis programs using the at least one energy data object to generate one or more energy analysis outputs;

packaging the one or more energy analysis outputs into an energy analysis response; and sending the energy analysis response to the requesting system.

2. The method of claim 1, wherein the one or more digital signatures comprise a signature generated using a private key associated with a device that generated the at least one energy data object.

3. The method of claim 2, wherein the device comprises a connected appliance.

4. The method of claim 2, wherein the private key comprises a private key associated with a manufacturer of the device.

5. The method of claim 1, wherein the one or more digital signatures comprise a signature generated using a private key associated with an entity that generated the at least one energy data object.

6. The method of claim 1, where the one or more analysis parameters comprise at least one parameter relating to one or more specified digital signatures associated with candidate energy analysis programs.

7. The method of claim 6, wherein selecting the one or more energy analysis program from the plurality of virtual energy analysis programs comprises:

verifying that the one or more selected energy analysis programs are associated with at least one of the one or more specified digital signatures.

8. The method of claim 6, wherein the one or more specified digital signatures comprise one or more of a digital signature associated with a creator of an energy analysis program, an organization associated with an energy analysis program, and a certification authority.

9. The method of claim 1, wherein the method further comprises authenticating, prior to executing the one or more analysis algorithms, the one or more selected energy analysis programs.

10. The method of claim 9, wherein authenticating the one or more selected energy analysis programs comprises verifying at least one digital signature associated with the one or more selected energy analysis programs.

11. The method of claim 10, wherein the at least one verified digital signature comprises one or more of a digital signature associated with a creator of an energy analysis program, an organization associated with an energy analysis program, and a certification authority.

12. The method of claim 1, wherein the one or more analysis parameters comprise at least one parameter relating to a cost associated with candidate energy analysis programs.

13. The method of claim 1, wherein the method further comprises decrypting the at least one energy data object.

14. The method of claim 1, wherein the method further comprises verifying one or more permissions associated with the one or more selected energy analysis programs.

15. The method of claim 14, wherein verifying the one or more permissions comprises determining that an identity associated with the one or more digital signatures is permitted to use the one or more selected energy analysis programs.

16. The method of claim 1, where the method further comprises generating an audit record.

17. The method of claim 16, wherein the audit record comprises a cryptographic hash of one or more of the energy data object, the one or more selected energy analysis programs, a timestamp, and the energy analysis response.

18. The method of claim 1, wherein the energy data object comprises energy usage information.

19. The method of claim 1, wherein the energy analysis response comprises one or more of load demand information, load type information, and energy savings recommendation information.

20. The method of claim 1, wherein the at least one energy data object and the one or more digital signatures are received from one or more of a device that generated the at least one energy data object and the requesting system.

* * * * *